(12) United States Patent
Vanden Berghe et al.

(10) Patent No.: US 8,039,501 B2
(45) Date of Patent: Oct. 18, 2011

(54) SYNEPHRINE DERIVATIVES USEFUL AS ANTI-INFLAMMATORY AGENTS

(75) Inventors: Wim Vanden Berghe, Gentbrugge (BE);
Karolien De Bosscher, Brakel (BE);
Serge Van Calenbergh, De Pinte (BE);
Guy Haegeman, Balegem (BE); Carl Jeffrey Lacey, Ghent (BE)

(73) Assignee: Universiteit Gent, Ghent (BE)

( * ) Notice: Subject to any disclaimer, the term of this patent is extended or adjusted under 35 U.S.C. 154(b) by 368 days.

(21) Appl. No.: 12/144,366

(22) Filed: Jun. 23, 2008

(65) Prior Publication Data

US 2009/0029999 A1 Jan. 29, 2009

Related U.S. Application Data

(63) Continuation-in-part of application No. PCT/EP2006/012520, filed on Dec. 22, 2006.

(60) Provisional application No. 61/011,983, filed on Jan. 23, 2008.

(30) Foreign Application Priority Data

Dec. 22, 2005 (GB) .................................. 0526123.5

(51) Int. Cl.
*A61K 31/4164* (2006.01)
*A61K 31/21* (2006.01)
*C07D 233/66* (2006.01)
*C07C 69/035* (2006.01)
*C07C 69/773* (2006.01)

(52) U.S. Cl. ...................... 514/399; 514/548; 548/334.1; 560/130

(58) Field of Classification Search .................. 560/130; 548/334.1; 514/399, 548
See application file for complete search history.

(56) References Cited

U.S. PATENT DOCUMENTS 5,670,546 A 9/1997 Park et al.
2003/0055030 A1 3/2003 De Bosscher et al.

FOREIGN PATENT DOCUMENTS

EP 0 721 939 7/1996
WO WO 01/45693 6/2001

OTHER PUBLICATIONS

Byrn et al., Chapter 11 Hydrates and Solvates in Solid-State Chemistry of Drugs (2nd Ed.), 1999, 233-247, 233.*
Morissette et al. Adv. Drug Delivery Rev. 2004, 56, 275-300.*
A.M. Rouhi, Chem. & Eng. News, Feb. 24, 2003, 81(8), 32-35.*
International Preliminary Report on Patentability for International Patent Application No. PCT/EP2006/012520, mailed Jul. 3, 2008.
Ibrahim et al., "Quantitative Measurement of Octopamines and Synephrines in Urine Using Caprillary Column Gas Chromatography Negative Ion Chemical Ionization Mass Spectrometry," *Analytical Chemistry*, vol. 56: 1695-1699, 1984.
International Search Report and Written opinion of the International Searching Authority (PCT/EP2006/012520) mailed Mar. 29, 2007.
European Patent Office Communication (EP 06841157.8) dated Jun. 23, 2011.

* cited by examiner

*Primary Examiner* — Jason M Nolan
(74) *Attorney, Agent, or Firm* — Clark & Elbing LLP

(57) ABSTRACT

This invention provides compounds having the structural formula:

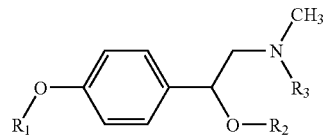

wherein:
$R_1$ is an acyl or sulfonyl group,
$R_2$ is an acyl group selected from the group consisting of acyl groups derived from cycloaliphatic, aromatic or heterocyclic monocarboxylic acids, imidazolylcarbonyl and triazolylcarbonyl, and
$R_3$ is hydrogen or an amino-protecting group,
a stereoisomer thereof, a solvate thereof, or a salt thereof, being useful as anti-inflammatory agents and anti-cancer agents.

23 Claims, 24 Drawing Sheets

US 8,039,501 B2

SYNEPHRINE DERIVATIVES USEFUL AS ANTI-INFLAMMATORY AGENTS

CROSS REFERENCE TO RELATED APPLICATIONS

This application is a continuation-in-part of International Application No. PCT/EP2006/012520, filed Dec. 22, 2006, which was published in English under PCT Article 21(2), and which claims the benefit of British patent application No. 0526123.5, filed Dec. 22, 2005. This application also claims the benefit of U.S. patent application No. 61/011,983 filed Jan. 23, 2008. The disclosures of each of the aforementioned applications are hereby incorporated by reference.

FIELD OF THE INVENTION

The present invention relates to novel synephrine derivatives being useful for treating or preventing inflammatory diseases or disorders. The present invention also relates to a method for preparing such compounds, as well as to pharmaceutical compositions comprising a therapeutically effective amount of such compounds.

BACKGROUND OF THE INVENTION

Synthetic glucocorticoids remain among the most effective agents for the treatment of chronic inflammatory diseases. However, major side effects severely limit their therapeutic use. Physiologic and therapeutic activities of glucocorticoids are mediated by a nuclear receptor belonging to a family of ligand-inducible transcription factors that, in addition to directly regulating their cognate gene programs, can also interfere with other signalling pathways, such as those using NF-κB.

NF-κB is an inducible transcription factor complex which regulates the expression of various genes involved in inflammatory and immune responses. It is activated upon exposure of cells to, among others, pro-inflammatory cytokines (such as TNF or IL-1), oxidants (such as hydrogen peroxide, ozone, superoxide anions), bacterial compounds, viral products, PKC activators (such as phorbol esters and platelet activating factor) and UV- or gamma-irradiation. NF-κB is therefore a promising target for anti-inflammatory and immuno-suppressive therapies. Inhibition of NF-κB activity by glucocorticoids has been well documented, although gene stimulatory effects by glucocorticoids have also been observed. Although glucocorticoids remain among the most potent immuno-suppressive and anti-inflammatory drugs currently available, and are especially effective in the treatment of chronic asthma or rheumatoid arthritis, side effects such as hypothalamic-pituitary-adrenal axis insufficiency, diabetes, altered lipid metabolism, steroid myopathy, osteoporosis, and infectious or neuro-psychiatric complications significantly limit the therapeutic use of classical glucocorticoid agonists in a significant number of patients, especially patients having a predisposition to one or more of the above-stated disorders.

WO01/45693 discloses 2-(4-acetoxyphenyl)-2-chloro-N-methylethyl-ammonium chloride as an anti-inflammatory agent.

Therefore there is a regular need in the art for novel compounds having significant and specific anti-inflammatory properties without having the side-effects of known effective anti-inflammatory agents such as glucocorticoids. There is a regular need in the art for effective anti-inflammatory agents having improved metabolisation and/or pharmacokinetic behaviour and which therefore can be more easily formulated into effective dosage forms. There is also a need in the art for such novel compounds which can be easily produced in good yield and purity from commercially available materials through a limited number of fully reproducible synthetic process steps.

Disorders in which cells are uncontrollably proliferating are generally referred to as cancer. This kind of disorders is commonly considered to result from a deregulation of the process that control cell division, differentiation and apoptosis. A combination of surgery, radiotherapy and chemotherapy is usually used for the treatment of Cancer. Chemotherapy is the treatment of cancer with drugs to kill cancer cells. Cytotoxic drugs usually used in chemotherapy are harming healthy tissue as well, and lead to a large variety of side effects.

Already two decades ago, natural and synthetic glucocorticoids have been identified as potential antitumor molecules in malignant melanoma, as inhibition of melanoma cell growth was observed, coinciding with reduced tumor size and weight. Glucocorticoid treatment of cancer, using Glucocorticoid Receptor (GR) agonists such as dexamethasone, aims at inducing apoptosis of cancerous cells. The GR-induced apoptotic effect has been described to require transactivation activity of that same receptor, therefore requiring a full GR agonist. E.g. systemic or local administration of dexamethasone significantly inhibits volume of brain tumors and reduces brain oedema (the latter remains a substantial cause of mortality). There is also some evidence in literature that glucocorticoids may target cancer by mediating effects in vascular functioning and angiogenesis. Various studies indicate that cytotoxic and cytostatic actions of glucocorticoids depend on GR transactivation activity that depends on GR dimerization (Sharma and Lichtenstein (2008) *Blood*, In Press)

Due to their high proliferation rate, cancer cells are prone to become resistant to chemical drugs. This is the case, for example, of prolonged glucocorticoid therapy, which presents the drawback that glucocorticoids induce down-regulation of their own cognate glucocorticoid receptors, which leads to therapy resistance.

Also, the success of classical glucocorticoid therapy for leukemia is overshadowed by potentially disabling side effects including e.g. hyperglycemia and a vascular necrosis of bone, especially prominent in young and adolescent patients.

As an alternative to dexamethasone treatment of cancer, prednisone, a corticosteroid with improved benefit over side effect ratio, has been used in the treatment of cancer as well. However, in some cases of severe malignancies, the use of dexamethasone in combination with radiotherapy or chemotherapy is preferred and the side effects then have to be considered as 'collateral damage' as the decision lies between survival or death.

There is a regular need in the art for novel compounds acting as anti-cancer agents that can be used, alone or in combination with another form or therapeutic treatment, for treating various forms of cancer.

SUMMARY OF THE INVENTION

The present invention relates to the unexpected finding that certain synephrine derivatives having a specific substitution pattern are able to relieve symptoms of disorders via a Glucocorticoid Receptor (GR) mediated pathway, in particular display specific anti-inflammatory activity and/or specific apoptosis-inducing activity and/or have a beneficial effect in osteochondral disorders such as osteoporosis. In accordance with some embodiments of the present invention this anti-inflammatory activity can be similar in extent as glucocorticoids. An advantage of embodiments of the present invention is that this anti-inflammatory activity can be without having the significant side effects of glucocorticoids and other known anti-inflammatory agents. These derivatives can be easily produced in good yield and purity from synephrine through a limited number of fully reproducible synthetic process steps.

The present invention therefore also relates to pharmaceutical compositions comprising a therapeutic effective amount of such synephrine derivatives, and optionally one or more pharmaceutically acceptable carriers. The present invention also relates to the use of such synephrine derivatives for making a medicament for treating or preventing anti-inflammatory disorders (in particular chronic inflammatory diseases). The present invention also includes a method of reduction or prevention or treatment of anti-inflammatory disorders (in particular chronic inflammatory diseases) by the administration of synephrine derivatives to a patient in need thereof, optionally in combination with one or more other drugs such as, but not limited to, other anti-inflammatory agents. In particular, this invention relates to such combinations having synergistic activity.

As a consequence of their specific apoptosis-inducing activity such synephrine derivatives are useful in the treatment of cancer. An advantage of embodiments of the present invention is to specifically mediate cancer cell apoptosis with limited or no side effects and/or limited or no receptor down-regulation. The present invention also provides synephrine derivatives for use in the treatment of cancer with reduced therapy resistance. Selected synephrine derivatives are useful for use in a therapeutic composition for inducing regression in a cancer cell population, in particular in prolonged cancer therapy. Selected synephrine derivatives act as dissociated GR agonists that lack GR transactivation activity and abolish GR dimerization. As a consequence, cancer therapy or tumor treatment with selected synephrine derivatives can be accompanied with reduced side effects compared to classical GC therapy. Selected synephrine derivatives do not lead to or to a lesser extent to down-regulation of the Glucocorticoid Receptor, and exhibit an improved side effect profile over glucocorticoids with respect to bone cell gene expression markers that are important for the development of osteoporosis. Accordingly embodiments of the invention relates to method of prevention, treatment or relief of osteochondral disorders such as osteoporosis with the synephrine derivatives of the present invention, more particularly with Compound A.

In a particular embodiment, the present invention relates to 2-(4-acetoxyphenyl)-2-chloro-N-methyl-ethylammonium chloride (hereinafter referred to as 'CpdA'), as well as a class of synephrine derivatives including, among others, 1-[4-(benzoyloxy)phenyl]-2-[(tert-butoxycarbonyl) (methyl)amino]ethyl1H-imidazole-1-carboxylate (hereinafter referred to as 'Benz'), 1-[4-(1-naphthoyloxy)phenyl]-2-[(tert-butyloxycarbonyl)(methyl)amino]ethyl 1H-imida-zole-1-carboxylate (hereinafter referred to as 'Naphth') and 1-[4-(isobutyryloxy) phenyl]-2-[(tert-butyloxycarbonyl)(methyl)amino]ethyl1H-imidazole-1-carboxylate (hereinafter referred to as 'Isobut'), for use in cancer therapy or tumor treatment.

According to a specific embodiment the present invention relates to the use of such synephrine derivatives for the manufacture of a medicament for the treatment of cancer, in particular hematological disorders.

According to another embodiment the present invention provides a method for the treatment of cancer such as, for example a hematological disorder or solid tumor cancer, comprising the step of administering to a subject in need of such treatment an effective amount of at least one of the selected synephrine derivatives.

An advantage of the latter embodiments of the present invention is that the apoptosis-inducing anti-cancer activity of the selected synephrine derivatives is accompanied by limited side effects when compared to the use of state of the art glucocorticoids such as dexamethasone and other known anti-cancer agents. Also an advantage of the present invention is a reduced therapy resistance.

The present invention further relates to pharmaceutical compositions comprising a therapeutic effective amount of such synephrine derivatives, and optionally one or more pharmaceutically acceptable carriers, and/or a second anti-cancer agent, for use in the treatment of cancer.

The present invention further relates to pharmaceutical compositions comprising a therapeutic effective amount of such synephrine derivatives, and optionally one or more pharmaceutically acceptable carriers, and/or a second anti-cancer agent, for use in the treatment of osteoporosis.

BRIEF DESCRIPTION OF THE DRAWINGS

FIG. 2A shows the activity of dexamethasone or CpdA on cells in a serum-free medium (SFM). FIG. 2B shows the activity of the same compounds on a medium containing foetal calf serum (FCS).

DEFINITIONS

Figure 1:
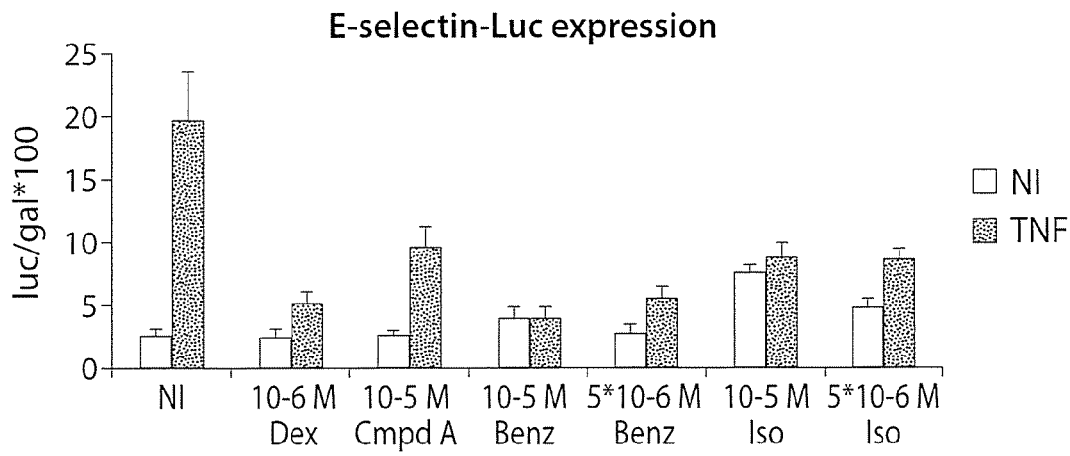
FIG. 1 shows the performance of representative compounds of the present invention in an anti-inflammatory assay, namely 1-[4-(benzoyloxy)phenyl]-2-[(tert-butoxycarbonyl)-methylamino]ethyl-1H-imidazole-1-carboxylate (Benz) and 1-[4-(isobutanoyloxy)phenyl]-2-[(tert-butoxycarbonyl)-methylamino]ethyl-1H-imidazole-1-carboxylate (Iso). References are dexamethasone (Dex) and compound A (cmpdA).

As used herein, and unless otherwise stated, the term "$C_{1\text{-}10}$ alkyl" means straight and branched chain saturated acyclic hydrocarbon monovalent groups having respectively 1, 2, 3, 4, 5, 6, 7, 8, 9 or 10 carbon atoms, such as but not limited to ethyl, propyl, n-butyl, 1-methylethyl(isopropyl), 2-methylpropyl (isobutyl), 1,1-dimethylethyl(tert-butyl), 2-methylbutyl, n-pentyl, dimethylpropyl, n-hexyl, 2-methylpentyl, 3-methylpentyl, n-heptyl, n-octyl, n-nonyl, n-decyl and the like; said $C_{1\text{-}10}$ alkyl group may further optionally include one or more suitable (i.e. non reactive under the reaction conditions wherein a molecule bearing said $C_{1\text{-}10}$ alkyl group is involved) substituents independently selected from the group consisting of amino, halogen, hydroxy, sulfhydryl, trifluoromethyl, methoxy and the like.

As used herein, and unless otherwise stated, the terms "cycloaliphatic" and "$C_{3\text{-}10}$ cycloalkyl" refer to a mono- or polycyclic saturated hydrocarbon monovalent group having from 3 to 10 carbon atoms, such as for instance cyclopropyl, cyclobutyl, cyclopentyl, cyclohexyl, cycloheptyl, cyclooctyl and the like, or a $C_{7\text{-}10}$ polycyclic saturated hydrocarbon monovalent group having from 7 to 10 carbon atoms such as, for instance, norbornyl, fenchyl, trimethyltricycloheptyl or adamantyl.

As used herein, the term "$C_{3\text{-}10}$ cycloalkyl-alkyl" refers to an aliphatic saturated hydrocarbon monovalent group (preferably a $C_{1\text{-}7}$ alkyl such as defined above) to which a $C_{3\text{-}10}$ cycloalkyl (such as defined above) is already linked such as, but not limited to, cyclohexylmethyl, cyclopentylmethyl and the like.

As used herein, and unless otherwise stated, the terms "aromatic" and "aryl" designate any mono- or polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo$C_{4\text{-}8}$ cycloalkyl groups (the latter being as defined above) such as, for instance, indanyl, tetrahydronaphthyl, fluorenyl and the like, all of the said groups being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, and unless otherwise stated, the term "heterocyclic" means a mono- or polycyclic, saturated or mono-unsaturated or poly-unsaturated monovalent hydrocarbon group having from 2 up to 15 carbon atoms and including one or more heteroatoms in one or more rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including groups wherein a heterocyclic ring is fused to one or more aromatic hydrocarbon rings for instance in the form of benzo-fused, dibenzo-fused or naphto-fused heterocyclic groups; within this definition are included heterocyclic groups such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzo-dioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzooxepinyl, dibenzopyranonyl, dibenzoquinoxalinyl, dibenzothiazepinyl, dibenzoiso-quinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphtotriazolyl, naphto-pyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzo-dihydrofuryl, benzothiopyronyl, benzothiopyranyl, benzoxazinyl, benzoxazolyl, benzodioxolyl, benzodioxanyl, benzothiadiazolyl, benzotriazinyl, benzo-thiazolyl, benzoxazolyl, phenothioxinyl, phenothiazolyl, phenothienyl(benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzo-carbazolyl, benzochromonyl, benziso-alloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may be independently substituted with a substituent selected from the group consisting of halogen, nitro, $C_{1-7}$ alkyl (such as above defined, in particular methyl), $C_{3-7}$ alkenyl, trifluoromethyl, $C_{3-10}$ cycloalkyl, aryl, arylalkyl, alkylaryl, hydroxyl, sulfhydryl, $C_{1-7}$ alkoxy (such as above defined, in particular methoxy), aryloxy, arylalkyloxy, thio $C_{1-7}$ alkyl, thio $C_{3-10}$ cycloalkyl, thioaryl, arylalkylthio, cyano, carboxylic acid or esters thereof; depending upon the number of unsaturations in each of said rings, heterocyclic groups may be sub-divided into heteroaromatic (or "heteroaryl") groups and non-aromatic heterocyclic groups; when a heteroatom of the said non-aromatic heterocyclic group is nitrogen, the latter may be substituted with a substituent selected from the group consisting of $C_{1-7}$ alkyl, $C_{3-10}$ cycloalkyl, aryl, arylalkyl and alkylaryl (each of said groups being as defined herein).

As used herein, and unless otherwise stated, the terms "$C_{1-7}$ alkoxy", "$C_{3-10}$ cycloalkoxy", "aryloxy", "arylalkyloxy", "thio $C_{1-7}$ alkyl", "thio $C_{3-10}$ cycloalkyl", "arylthio" and "arylalkylthio" refer to substituents wherein respectively a $C_{1-7}$ alkyl, a $C_{3-10}$ cycloalkyl, aryl, arylalkyl or heterocyclic group (each of them such as defined herein), are attached to an oxygen atom or a divalent sulfur atom through a single bond, such as but not limited to methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy, and the like.

As used herein, and unless otherwise stated, the term "halogen" means any atom selected from the group consisting of fluoro, chloro, bromo and iodo.

As used herein, and unless otherwise stated, the term "$C_{2-7}$ alkenyl" designates a straight or branched acyclic hydrocarbon monovalent group having one or more ethylenic unsaturations and having from 2 to 7 carbon atoms such as, for example, vinyl, 1-propenyl, 2-propenyl(allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like.

As used herein, and unless otherwise stated, the terms "arylalkyl", "arylalkenyl" and "heterocyclic-substituted alkyl" refer to an aliphatic saturated or ethylenically unsaturated hydrocarbon monovalent group (preferably a $C_{1-7}$ alkyl or $C_{2-7}$ alkenyl such as defined above) onto which an aryl or heterocyclic group (such as defined above) is attached, and wherein the said aliphatic, aryl or heterocyclic group may be optionally substituted with one or more substituents independently selected from the group consisting of halogen, amino, hydroxyl, sulfhydryl, $C_{1-7}$ alkyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, 1-amino-2-[indol-2-yl]ethyl, styryl, pyridylmethyl (including all isomers thereof, pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein, and unless otherwise stated, the term "alkylaryl" and alkyl-substituted "heterocyclic" refer to an aryl or heterocyclic radical (such as defined above) onto which are bonded one or more aliphatic saturated or unsaturated hydrocarbon monovalent groups, preferably one or more $C_{1-7}$ alkyl, $C_{2-7}$ alkenyl or $C_{3-10}$ cycloalkyl groups as defined above such as, but not limited to, o-toluoyl, m-toluoyl, p-toluoyl, 2,3-xylyl, 2,4-xylyl, 3,4-xylyl, o-cumenyl, m-cumenyl, p-cumenyl, o-cymenyl, m-cymenyl, p-cymenyl, mesityl, ter-butylphenyl, lutidinyl (i.e. dimethylpyridyl), 2-methylaziridinyl, methyl-benzimidazolyl, methylbenzofuranyl, methylbenzothiazolyl, methylbenzo-triazolyl, methylbenzoxazolyl and methylbenzselenazolyl.

As used herein, and unless otherwise stated, the term "acyl" refers to a substituent derived from an acid such as an organic monocarboxylic acid, a carbonic acid, a carbamic acid (resulting into a carbamoyl substituent) or the thioacid (resulting into a thioacyl substituent) or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl(oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids are designated herein as aliphatic or cycloaliphatic acyl and sulfonyl groups and include, but are not limited to, the following:

- alkanoyl, e.g. derived from a $C_{1-10}$ alkyl group (for example formyl, acetyl, propionyl, butyryl, isobutyryl, valeryl, isovaleryl, pivaloyl (i.e. trimethylacetyl), hexanoyl, octanoyl and the like);
- cycloalkanoyl, e.g. derived from a $C_{3-10}$ cycloalkyl group (for example cyclopropanecarbonyl, cyclobutanecarbonyl, cyclopentanecarbonyl, cyclohexanecarbonyl, 1-adamantanecarbonyl and the like);
- cycloalkyl-alkanoyl (for example cyclohexylacetyl, cyclopentylacetyl, cyclopentylpropionyl and the like);
- alkenoyl (for example acryloyl, methacryloyl, crotonoyl and the like);
- alkylthioalkanoyl (for example methylthioacetyl, ethylthioacetyl and the like);
- alkanesulfonyl (for example mesyl, ethanesulfonyl, propanesulfonyl and the like);
- alkoxycarbonyl (for example methoxycarbonyl, ethoxycarbonyl, propoxycarbonyl, isopropoxycarbonyl, n-butoxycarbonyl, isobutoxycarbonyl, n-pentoxycarbonyl, n-hexyloxycarbonyl, n-octyloxycarbonyl, n-decyloxycarbonyl, n-dodecyloxycarbonyl, and the like);
- cycloalkoxycarbonyl, e.g. cyclohexyloxycarbonyl, cyclopentyloxycarbonyl and cyclobutyloxycarbonyl,
- alkylcarbamoyl (for example methylcarbamoyl, i.e. methylaminoformyl, and the like);
- (N-alkyl)-thiocarbamoyl (for example (N-methyl)-thiocarbamoyl and the like);
- alkylcarbamidoyl (for example methylcarbamidoyl and the like); and
- alkoxalyl (for example methoxalyl, ethoxalyl, propoxalyl and the like);

Acyl and sulfonyl groups may also originate from aromatic monocarboxylic acids and include, but are not limited to, the following:

- aroyl (for example benzoyl, toluoyl, xyloyl, 1-naphthoyl, 2-naphthoyl and the like);
- aralkanoyl (for example phenylacetyl and the like);
- aralkenoyl (for example cinnamoyl and the like);
- aryloxyalkanoyl (for example phenoxyacetyl and the like);
- arylthioalkanoyl (for example phenylthioacetyl and the like);
- arylaminoalkanoyl (for example N-phenylglycyl, and the like);
- arylsulfonyl (for example benzenesulfonyl, toluenesulfonyl, naphthalene sulfonyl and the like);
- aryloxycarbonyl (for example phenoxycarbonyl, naphthyloxycarbonyl and the like);
- aralkoxycarbonyl (for example benzyloxycarbonyl and the like);
- arylcarbamoyl (for example phenylcarbamoyl, naphthylcarbamoyl and the like);
- arylglyoxyloyl (for example phenylglyoxyloyl and the like).
- arylthiocarbamoyl (for example phenylthiocarbamoyl and the like); and
- arylcarbamidoyl (for example phenylcarbamidoyl and the like).

Acyl groups may also originate from an heterocyclic monocarboxylic acids and include, but are not limited to, the following:

- heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like);
- heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolylpropionyl, tetrazolylacetyl, 2-(2-amino-4-thiazolyl)-2-methoxyiminoacetyl and the like).

As used herein and unless otherwise stated, the term "stereoisomer" refers to all possible different isomeric as well as conformational forms which the compounds of this invention may possess, in particular all possible stereochemically and conformationally isomeric forms, all diastereomers, enantiomers and/or conformers of the basic molecular structure.

As used herein and unless otherwise stated, the term "enantiomer" means each individual optically active form of a compound of this invention, having an optical purity or enantiomeric excess (as may be determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols, ketones, esters and the like.

As used herein, the terms "cancer" and "cancerous" refer to or describe the physiological condition in mammals that is typically characterized by unregulated cell growth, i.e., proliferative disorders. "Cancer" is a general term referring to any type of malignant neoplasm. Examples include cancers such as carcinoma, lymphoma, blastoma, sarcoma, and leukemia, as well as other cancers disclosed herein. More particular examples of such cancers include hematological disorders, breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and Central Nervous System (CNS) cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; multiple myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

As used herein, the term "tumor" or "neoplasm" refers to all neoplastic or abnormal cell growth and proliferation, whether malignant or benign, and all pre-cancerous and cancerous cells and tissues. For example, a particular cancer may be characterized by either or both a solid mass tumor and a non-solid tumor. Tumor tissue is abnormal tissue that grows by cellular proliferation more rapidly than normally, and continues to grow after the stimuli that initiated the new growth cease. The term "lesion" as used herein, generally refers to an abnormality involving any tissue or organ due to any disease or any injury, and is also used herein to refer to a neoplasm.

A tumor mass, if present, may be a primary tumor mass. A primary tumor mass refers to a growth of cancer cells in a tissue resulting from the transformation of a normal cell of that tissue. Cancer cells can "break away", "leak", or "spill" from a primary tumor, enter lymphatic and blood vessels, circulate through the bloodstream, and settle down to grow within normal tissues elsewhere in the body. Metastasis is one of three hallmarks of malignancy of tumor growth (contrast benign tumors). Most tumors or neoplasms can metastasize, although in varying degrees, barring a few exceptions (e.g., Glioma and Basal cell carcinoma never metastasize). When tumor cells metastasize, the new tumor is called a secondary or metastatic tumor, and its cells are like those in the original tumor. The selected synephrine derivatives are used for the treatment of both primary and secondary tumor cancers.

In most cases, a solid tumor mass is identified by the presence of a cyst, which can be found through visual or palpation methods, or by irregularity in shape, texture or weight of the tissue. However, some tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

For a non-solid tumor, there is an overgrowth of cells but they never get a chance to clump together because they are dispersed throughout the body and are in continual motion. Non-solid tumor cancers are those that affect the cells of a circulating system. The body's two main systems are the blood system and the lymph system. Examples of non-solid tumors include leukemias, multiple myelomas and lymphomas. Some examples of leukemias include acute myelocytic leukemia (AML), chronic myelocytic leukemia (CML), acute lymphocytic leukemia (ALL), chronic lymphocytic leukemia (CLL), erythrocytic leukemia or monocytic leukemia. Some examples of lymphomas include lymphomas associated with Hodgkin's disease and Non-Hodgkin's disease.

As used herein, the term "apoptosis", or programmed cell death, refers to cell death as a result of activation of an intracellular "suicide" or "cell-self-destructing" process. The process that apoptic cells undergo comprises a series of molecular events leading to some or all of the following morphological changes: DNA fragmentation; chromatin condensation; nuclear envelope breakdown; and cell shrinkage. Apoptosis does not lead to lysis of cells and thus avoids damage to neighboring tissue.

DETAILED DESCRIPTION OF THE INVENTION

In a first aspect, the present invention relates to a family of compounds represented by the structural formula (I):

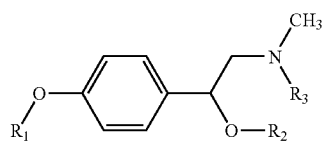

wherein:
$R_1$ is an acyl or sulfonyl group, in particular $R_1$ is —C(=O)—$R_4$ or —S(=O)$_2$—$R_4$,
$R_4$ is selected from the group consisting of $R_5$, —O$R_5$, —NH$R_5$ and —S$R_5$, $R_5$ is selected from the group consisting of hydrogen; straight chain or branched chain, aliphatic or cycloaliphatic or aromatic groups such as $C_{2-10}$ alkyl, $C_{2-10}$ alkenyl, $C_{2-10}$ cycloalkyl, $C_{2-10}$ alkynyl, aryl, arylalkyl, and saturated, partly unsaturated or aromatic heterocyclic groups, $R_2$ is an acyl group selected from the group consisting of acyl groups derived from cycloaliphatic, aromatic or heterocyclic monocarboxylic acids, imidazolylcarbonyl or triazolylcarbonyl, in particular $R_2$ is —C(=O)—$R_6$, $R_6$ is selected from the group consisting of aliphatic or cycloaliphatic or aromatic groups such as $C_{2-10}$ alkyl, $C_{3-10}$ cycloalkyl, $C_{2-10}$ alkenyl, $C_{2-10}$ alkynyl, aryl, arylalkyl and saturated, partly unsaturated or aromatic heterocyclic groups, $R_3$ is hydrogen or an amino-protecting group, in particular $R_3$ is hydrogen, —C(=O)—$R_7$, —C(=O)—O$R_7$ or aryl-$C_{1-7}$alkyl; and $R_7$ is $C_{1-10}$ alkyl, $C_{2-10}$ alkenyl, aryl, or aryl-$C_{1-10}$ alkyl, wherein each of said alkyl, alkenyl or aryl may be substituted with one or more substituents independently selected from the group consisting of halogen, alkyl, alkoxy, nitro, cyano and hydroxy, As well as stereoisomers thereof, solvates thereof, or salts thereof.

Within this broad acceptance of the invention, each generic term such as, but not limited to, "acyl", "sulfonyl", "heterocyclic", "cycloaliphatic" and "aromatic" may, independently from each other, be understood according to any of the particular meanings thereof indicated in the above definitions.

A first embodiment of this aspect of the invention relates to compounds wherein $R_1$ is an acyl group derived from an aliphatic, cycloaliphatic, aromatic or heterocyclic monocarboxylic acid. $R_1$ may be different from $R_2$, especially when $R_1$ is an aliphatic acyl group. Alternatively, according to a second embodiment of this aspect of the invention, when $R_1$ is an acyl group derived from a cycloaliphatic, aromatic or heterocyclic monocarboxylic acid, $R_1$ may be the same as $R_2$.

In view of the commercial availability of the starting materials, a preferred embodiment of this aspect of the invention relates to compounds wherein $R_1$ is selected from the group consisting of benzoyl, p-toluoyl, 1-naphthalenecarbonyl, 2-naphthalenecarbonyl, 4-morpholinocarbonyl, 1-piperidinocarbonyl, 1-imidazolidinocarbonyl, 1-pyrrolidinocarbonyl, 2-thiazole-carbonyl, 1-methyl-1H-pyrrole-2-carbonyl, 2-furanecarbonyl, 3-furanecarbonyl, 3-pyridinecarbonyl, 4-pyridinecarbonyl, 2-thiophenecarbonyl, cyclobutane-carbonyl, cyclopentanecarbonyl, cyclohexanecarbonyl, 1-adamantane-carbonyl, pipecolinyl and 2-norbornanecarbonyl.

Another embodiment of this aspect of the invention relates to compounds wherein $R_1$ is selected from the group consisting of acetyl, formyl, propanoyl, butanoyl and pentanoyl.

Another embodiment of this aspect of the invention relates to compounds wherein $R_3$ is the same as $R_2$.

Suitable amino-protecting groups such as required for $R_3$ are well known in the art and are preferably selected from the group consisting of arylcarbonyl, alkyloxycarbonyl and arylalkyloxycarbonyl. A few non-limiting examples of suitable amino-protecting groups include benzyloxycarbonyl (which may be introduced by reaction with benzylchloroformate under alkaline conditions, e.g. making use of sodium hydroxide or hydrogenocarbonate) and 9-fluorenylmethoxycarbonyl (which may be introduced by reaction with 9-fluorenylmethyl chloroformate). Another example of an amino-protecting group is a tert-butoxycarbonyl group which may be introduced by reaction with di-tert-butyl dicarbonate under alkaline conditions. Other suitable amino-protecting groups for R₃ include, but are not limited to aralkyl type protecting groups comprising benzyl, p-methoxybenzyl, p-nitrobenzyl, p-bromobenzyl and triphenylmethyl(trityl); alternative acyl type protecting groups comprising formyl, acetyl, chloroacetyl, dichloroacetyl, trichloroacetyl, trifluoroacetyl, phenylacetyl, o-nitrophenoxyacetyl, sec-butyryl, pivaloyl—(also known as tert-butyryl), cyclopropanoyl, benzoyl, o-nitrobenzoyl, and alpha-chlorobutyryl; or other urethane type protecting groups comprising benzyloxycarbonyl, p-chlorobenzyloxycarbonyl, p-nitrobenzyloxycarbonyl, p-bromobenzyloxy-carbonyl, p-methoxybenzyloxycarbonyl, o-nitrobenzyloxycarbonyl, tert-butyloxycarbonyl, tert-amyloxycarbonyl, diisopropyl methoxycarbonyl, isopropyloxycarbonyl, allyloxycarbonyl, cyclopentyloxycarbonyl, adamantyl-oxycarbonyl and cyclohexyloxycarbonyl.

Still another embodiment of the present invention relates to compounds represented by the structural formula (I), wherein when R₄ is R₅ and R₁ is —C(=O)—R₄ then a heterocyclic group R₅ (i.e. R₄) may be attached through one of its heteroatoms to the carbon atom of the carbonyl group of R₁.

Still another embodiment of the present invention relates to compounds represented by the structural formula (I), wherein a heterocyclic group R₆ may be attached through one of its heteroatoms to the carbon atom of the carbonyl group of R₂.

For pharmaceutical use, especially for the formulation of suitably bioavailable drug formulations, it may be particularly preferred that the compound of the invention is present in the form of a non-toxic acid addition salt, more preferably a pharmaceutically acceptable acid addition salt, of a compound defined according to the above structural formula and wherein R₃ is hydrogen.

The latter form includes any therapeutically active non-toxic addition salt which the compounds of this invention are able to form with a (preferably pharmaceutically acceptable) salt-forming agent. Such addition salts may conveniently be obtained by treating the compounds of the invention with an effective amount (preferably an at least stoechiometric amount) of an appropriate salt-forming acid, while using reaction conditions (such as, but not limited to, temperature, pressure, time and the like) conventional in the art for such treatment. For instance, compounds having basic properties such as the amino compounds of the present invention, may conveniently be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, but not limited to, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic (Z)-2-butenedioic, (E)2-butenedioic, 2-hydroxybutanedioic, 2,3-dihydroxybutane-dioic, 2-hydroxy-1,2,3-propanetricarboxylic, cyclohexanesulfamic acids and the like.

An advantage of the present invention is that compounds defined according to the above structural formula are easily accessible in good yield and purity through a synthetic scheme (e.g. scheme 1 below) involving a limited number of process steps and starting from commercially available materials. An exemplary but non-limiting method for preparing the compounds of this invention comprises the steps of:
(a) reacting synephrine with an amino-protecting reagent (e.g. of the type specified hereinbefore) to form an amino-protected synephrine,
(b) reacting said amino-protected synephrine with an acyl or sulfonyl halide, preferably an acyl or sulfonyl chloride selected from the group consisting of carboxylic acid chlorides, carbamic acid chlorides, chloroformates, thiocarboxylic acid chlorides, imidic acid chlorides and sulfonic acid chlorides to produce a 4-[2-(N-protected-methylamino)-1-hydroxyethyl]phenyl ester, in particular a 4-[2-(N-protected-methylamino)-1-hydroxyethyl]phenyl benzoate, and
(c) reacting said 4-[2-(N-protected-methylamino)-1-hydroxyethyl]phenyl ester, in particular said 4-[2-(N-protected-methylamino)-1-hydroxyethyl]phenyl benzoate, with an activated carbonyl compound selected from the group consisting of carboxylic acid chlorides, carbamic acid chlorides, chloroformates, thiocarboxylic acid chlorides, imidic acid chlorides, 1,1'-carbonyldiimidazole, 1,1'-thiocarbonyldiimidazole and 1,1'-carbonylditriazole.

Carboxylic acid halides suitable for use in the synthesis (step (b) of the above method) of the compounds of the present invention include aromatic monocarboxylic acid halides, e.g. benzoyl bromide and optionally monosubstituted or polysubstituted (wherein substituents may be the same or different) benzoyl chlorides such as, but not limited to, benzoyl chloride, p-anisoyl-chloride, 2-bromobenzoyl chloride, 4-bromobenzoyl chloride, 3-chlorobenzoyl chloride, pentafluorobenzoyl chloride, 2-chlorobenzoyl chloride, p-toluoyl chloride, 4-chlorobenzoyl chloride, 2,4-dichlorobenzoyl chloride, 3,4-dichlorobenzoyl chloride, 4-nitrobenzoyl chloride, 4-fluorobenzoyl chloride, 2-fluoro-benzoyl chloride, o-toluoyl chloride, m-toluoyl chloride, 4-cyanobenzoyl chloride, 3-nitrobenzoyl chloride, 4-tert-butyl-benzoyl chloride, 4-biphenylcarbonyl chloride, 3,5-dimethoxybenzoyl chloride, 3-fluorobenzoyl chloride, 2,6-dichlorobenzoyl chloride, 4-butylbenzoyl chloride, 4-heptyloxybenzoyl chloride, 4-hexylbenzoyl chloride, 4-hexyloxybenzoyl chloride, 4-pentylbenzoyl chloride, m-anisoyl chloride, 2,6-difluorobenzoyl chloride, 2-nitrobenzoyl chloride, 4-chloro-3-nitrobenzoylchloride, 3,4-difluoro-benzoyl chloride, 2-iodobenzoyl chloride, 1-naphthoyl chloride, o-anisoyl chloride, 2,4-difluorobenzoyl chloride, 4-(trifluoromethyl)benzoyl chloride, 3-(chloro-methyl)-benzoyl chloride, 4-(chloromethyl)-benzoyl chloride, 3-(dichloromethyl)-benzoyl chloride, 2,3,4,5-tetrafluorobenzoyl chloride, 2,4,6-trichlorobenzoyl chloride, 2,3,4-trifluorobenzoyl chloride, 2,4,6-trifluorobenzoyl chloride, 4-bromo-2-fluoro-benzoyl chloride, 2,3,5,6-tetrafluorobenzoyl chloride, 3,5-dinitrobenzoyl chloride, 4-heptylbenzoyl chloride, 4-iodobenzoyl chloride, 4-octylbenzoyl chloride, 4-pentyl-oxybenzoyl chloride, 4-phenylazobenzoyl chloride, 4-propylbenzoyl chloride, methyl 4-chloro-carbonylbenzoate, 3,5-dichlorobenzoyl chloride, 3-fluoro-4-trifluoromethyl-benzoyl chloride, 2,6-dimethoxybenzoyl chloride, piperonyloyl chloride, 2,4-dimethoxybenzoyl chloride, 3,4-dihydro-2H-1,5-benzodioxepine-6-carbonyl chloride, 2,3-dihydro-1,4-benzodioxine-6-carbonyl chloride, 2,3-dihydro-1,4-benzodioxine-5-carbonyl chloride, 1-benzofuran-5-carbonyl chloride, 2,1,3-benzothiadiazole-4-carbonyl chloride, 2,1,3-benzothiadiazole-5-carbonyl chloride, 1,2,3-benzothia-diazole-5-carbonyl chloride, 2,1,3-benzoxadiazole-5-carbonyl chloride, 6-quinoxaline-carbonyl chloride, 4-(2-thienyl)-benzoyl chloride, 4-methyl-3,4-dihydro-2H-1,4-benzoxazine-7-carbonyl chloride, 4-(1,2,3-thiadiazol-4-yl)benzoyl chloride, 4-(1H-pyrazol-1-yl)benzoyl chloride, 1-methyl-1H-1,2,3-benzotriazole-5-carbonyl chloride, 1-benzothiophene-5-carbonyl chloride, 2,2-dimethyl-2,3-dihydro-1-benzofuran-7-carbonyl chloride, 4-[(dipropylamino)sulfonyl]benzene-1-carbonyl chloride, 4-[3-(trifluoromethyl)-1H-pyrazol-1-yl]-benzoyl chloride, 2-bromo-5-methoxybenzene-1-carbonyl chloride, 5-bromo-2,3,4-trimethylbenzoyl chloride, 2-chloro-6-fluorobenzene-1-carbonyl chloride, 2,3-dimethylbenzene-1-carbonyl chloride, 3,4-dimethylbenzene-1-carbonyl chloride, 2-chloro-4-fluorobenzoyl chloride, 5,5,8,8-tetramethyl-5,6,7,8-tetrahydro-2-naphthalene-carbonyl chloride, 2-(4-methoxyphenoxy)-5-nitrobenzene-1-carbonyl chloride, 2,3-difluorobenzoyl chloride, 2-fluoro-5-(trifluoromethyl)benzoyl chloride, 2,3,6-trifluoro-benzoyl chloride, 1-isopropyl-1H-1,2,3-benzotriazole-5-carbonyl chloride, 1-isopropyl-1H-1,2,3-benzotriazole-5-carbonyl chloride, 3-fluoro-4-methylbenzoyl chloride, 3-(cyclo-pentyloxy)-4-methoxybenzoyl chloride, 4-fluoro-3-(trifluoromethyl)benzoyl chloride, 2,3-dihydro-1-benzofuran-7-carbonyl chloride, 3-(2-methylthiazol-4-yl)-benzoyl chloride, 1-isopropyl-2-(trifluoromethyl)-1H-benzimida-zole-5-carbonyl chloride, 5-bromo-2,3-di-hydrobenzo[b]furan-7-carbonyl chloride, 2,4,6-trimethylbenzoyl chloride, 2-(2-thienyl)-benzoyl chloride, 3-cyanobenzoyl chloride, acetylsalicyloyl chloride, 3-(5-methyl-1,2,4-oxadiazol-3-yl)-benzoyl chloride, and 4-(5-methyl-1,2,4-oxadiazol-3-yl)-benzoyl chloride.

Numerous other carboxylic acid chlorides are known to the person skilled in the art and commercially available for use as acylating reagent for use in the above reaction step. Particular carbonyl chlorides for use in the method of the invention include, but are not limited to, cinnamoyl chloride, hydrocinnamoyl chloride, 2-phenylbutyryl chloride, phenylacetyl chloride and 4-fluorophenylacetyl chloride.

Phenylsulfonyl chlorides (represented by the structural formula V—B) suitable for use in the synthesis (step (b) of the above method) of the compounds of the present invention include, but are not limited to, 4-fluorobenzenesulfonyl chloride, 2-mesitylenesulfonyl chloride, 4-methoxybenzene-sulfonyl chloride, p-toluenesulfonyl chloride, pentafluorobenzene-sulfonyl chloride, benzenesulfonyl chloride, 4-bromobenzenesulfonyl chloride, N-acetylsulfanilyl chloride, 2,4,6-triisopropyl-benzenesulfonyl chloride 2-naphthalenesulfonylchloride, 4-chloro-benzenesulfonyl chloride 3,5-dichloro-2-hydroxy-benzenesulfonylchloride, 2,5-dichloro-benzenesulfonyl chloride, pipsyl chloride, 1-naphthalenesulfonylchloride, methyl 2-(chlorosulfonyl)-benzoate, 4-tert-butylbenzene-sulfonyl chloride, 3-(trifluoromethyl)benzenesulfonyl chloride, 2-bromobenzenesulfonyl chloride, 4-acetylbenzene-sulfonylchloride, 2-(trifluoromethyl)-benzenesulfonyl chloride, 3,4-dichlorobenzene-sulfonyl chloride, 3,4-dimethoxybenzenesulfonyl chloride, 3-chlorobenzenesulfonyl chloride, 2-chloro-4-fluorobenzenesulfonyl chloride, 3,5-dichlorobenzenesulfonyl chloride, 3-chloro-4-fluorobenzenesulfonyl chloride, 2,4-dichlorobenzenesulfonyl chloride, 2,5-dimethoxybenzenesulfonyl chloride, 3-bromo-benzenesulfonyl chloride, 2,3-dichlorobenzenesulfonyl chloride, 5-fluoro-2-methylbenzenesulfonyl chloride, 3-fluorobenzenesulfonyl chloride, 2,3,5,6-tetramethyl-benzenesulfonyl chloride, 3-chloro-2-methylbenzenesulfonyl chloride, 2,5-dibromo-3,6-difluoro-benzenesulfonyl chloride, 2,6-difluorobenzene-sulfonyl chloride, 2-chloro-benzenesulfonyl chloride, 5-bromo-2-methoxybenzenesulfonyl chloride, 5-chloro-2-methoxybenzenesulfonyl chloride, 2,4-difluorobenzene-sulfonyl chloride, 2-cyano-benzenesulfonyl chloride, 2-chloro-5-(trifluoromethyl)-benzenesulfonyl chloride, 4-bromomethylbenzenesulfonyl chloride, 2,4-dimethoxybenzenesulfonyl chloride, 4-chloro-3-nitrobenzenesulfonyl chloride, 4-(chlorosulfonyl)-benzoic acid, 3-nitro-benzenesulfonyl chloride, 4-nitrobenzenesulfonyl chloride, 2-(methylsulfonyl)-benzenesulfonyl chloride, 4-(methylsulfonyl)-benzene-sulfonyl chloride, 3-(chloro-sulfonyl)-benzoic acid, 2,4-dichloro-5-methylbenzene-sulfonyl chloride, 4-(trifluoro-methoxy)-benzenesulfonyl chloride, 2-methoxy-4-nitrobenzenesulfonyl chloride, 4-bromo-2-chlorobenzenesulfonyl chloride, 2,3-dihydro-1-benzofuran-5-sulfonyl chloride, 2,3-dihydro-1,4-benzodioxine-6-sulfonyl chloride, 1,3-benzothiazole-6-sulfonyl chloride, 2,1,3-benzothiadiazole 4 sulfonyl chloride, 2,1,3-benzothiadiazole-5-sulfonyl chloride, 2,1,3-benzoxadiazole-4-sulfonyl chloride, 3,4-dihydro-2H-1,5-benzodioxepine-7-sulfonyl chloride, 4-methyl-3,4-dihydro-2H-1,4-benzoxazine-7-sulfonyl chloride, 4-(1,3-oxazol-5-yl)benzenesulfonyl chloride, 4-(1,2,3-thiadiazol-4-yl)benzenesulfonyl chloride, 4-(1H-pyrazol-1-yl)benzenesulfonyl chloride, 4-(3-chloro-2-cyanophenoxy)benzene-1-sulfonyl chloride, 5-chlorosulfonyl-2-hydroxybenzoic acid, 4-bromo-2,5-difluoro-benzene-1-sulfonyl chloride, 4-(acetylamino)-3-chloro-benzene-1-sulfonyl chloride, 3,5-di-(trifluoromethyl)-benzene-1-sulfonyl chloride, 2-fluorobenzenesulfonyl chloride, 4-methyl-3-nitrobenzene-1-sulfonyl chloride, 5-chloro-2,1,3-benzoxadiazole-4-sulfonyl chloride, 3-(5-methyl-1,3,4-oxadiazol-2-yl)benzenesulfonyl chloride, methyl 3-(chlorosulfonyl)-4-methoxybenzoate, 4-bromo-2-(trifluoromethyl)-benzenesulfonyl chloride, 2,2-dimethyl-6-chromanesulfonyl chloride, 4-(morpholine-4-sulfonyl)benzenesulfonyl chloride, 4-(pyrrolidine-1-sulfonyl)-benzene-sulfonyl chloride, 3-(2-methyl-4-pyrimidinyl)benzenesulfonyl chloride, 2-cyano-5-methylbenzenesulfonyl chloride, 2,5-dimethylbenzenesulfonyl chloride, 4-chloro-3-(trifluoromethyl)-benzenesulfonyl chloride, 4-bromo-2-methylbenzene-1-sulfonyl chloride, 2-chloro-4-(trifluoro-methyl)-benzene-1-sulfonyl chloride, 2-chloro-4-cyano-benzene-1-sulfonyl chloride, 2,6-dichloro-4-(trifluoromethyl)-benzene-1-sulfonyl chloride, 3,4-difluorobenzene-1-sulfonyl chloride, 2-iodobenzene-1-sulfonyl chloride, 4-methyl-1-naphthalenesulfonyl chloride, 4-(trifluoromethyl)benzene-1-sulfonyl chloride, 2,6-dichlorobenzene-1-sulfonyl chloride, 2-(trifluoromethoxy)benzene-1-sulfonyl chloride, 4-cyanobenzene-1-sulfonyl chloride, 4-butoxybenzene-1-sulfonyl chloride, 2,3,4-trifluorobenzene-1-sulfonyl chloride, 4-bromo-2-(trifluoromethoxy)benzene-1-sulfonyl chloride, 3-cyanobenzene-1-sulfonyl chloride, 3-chloro-4-methylbenzene-1-sulfonyl chloride, 4-bromo-2-ethyl-benzene-1-sulfonyl chloride, 5,5,8,8-tetramethyl-5,6,7,8-tetrahydro-2-naphthalene-sulfonyl chloride, 4-(2-chloro-6-nitrophenoxy)benzene-1-sulfonyl chloride, 3,5-dichloro-4-(2-chloro-4-nitrophenoxy)benzene-1-sulfonyl chloride, 4-pentylbenzene-1-sulfonyl chloride, 4-ethylbenzene-1-sulfonyl chloride, 4-propylbenzene-1-sulfonyl chloride, 4-butylbenzene-1-sulfonyl chloride, 3-toluenesulfonyl chloride, 4-isopropyl-benzenesulfonyl chloride, 4-(2-oxo-1-pyrrolidinyl)benzene sulfonyl chloride, 4-(2-methoxyphenoxy)benzenesulfonyl chloride, 4-(2-chloro-phenoxy)benzenesulfonyl chloride, 4-(2-methylphenoxy)benzenesulfonyl chloride, 4'-chloro(1,1'-biphenyl)-4-sulfonyl chloride, 4'-fluoro(1,1'-biphenyl)-4-sulfonyl chloride, 4'-methoxy-(1,1'-biphenyl)-4-sulfonyl chloride, 3',4'-dichloro-(1,1'-biphenyl)-4-sulfonyl chloride, 4-phenoxybenzenesulfonyl chloride, 4'-methyl-(1,1'-biphenyl)-4-sulfonyl chloride, 5-bromo-2,3-dihydrobenzo[b]furan-7-sulphonyl chloride, 3,4,5-trifluoro-benzenesulfonyl chloride, 3-(5-methyl-1,2,4-oxadiazol-3-yl)benzenesulfonyl chloride, 4-(2-methyl-1,3-thiazol-4-yl)benzenesulfonyl chloride, 1-acetyl-5-indolinesulfonyl chloride, 3-(2-methyl-1,3-thiazol-4-yl)benzene-sulfonyl chloride and 1,3-benzodioxole-5-sulfonyl chloride.

Arylalkanoyl chlorides also suitable for use in the synthesis (step (b) of the above method) of the compounds of the present invention include, but are not limited to, 2-(2-naphthyl)acetyl chloride, 2-(1-naphthyl)ethanoyl chloride, and optionally substituted phenylalkanoyl chlorides (e.g. phenylacetyl chloride, 4-methoxyphenylacetyl chloride, 2-(3,5-difluorophenyl)ethanoyl chloride, 4-chlorophenylacetyl chloride, 3-methoxyphenylacetyl chloride, 4-fluorophenylacetyl chloride, phenylpropionyl chloride, 4-methoxyphenylpropionyl chloride, 2-fluorophenylpropionyl chloride, and 2-phenylbutyryl chloride, as well as acid chlorides derived from 4-bromophenylacetic acid, 3-bromophenylacetic acid, 2-bromophenylacetic acid, 3-chlorophenylacetic acid, 2-chlorophenylacetic acid, 3-fluorophenylacetic acid, 2-fluorophenylacetic acid, 4-nitrophenylacetic acid, 3-nitrophenylacetic acid, 2-nitrophenylacetic acid, 2,4-dichlorophenylacetic acid, 2,6-dichlorophenylacetic acid, 3,4-dichlorophenylacetic acid, 2-methoxyphenylacetic acid, 4-methylphenylacetic acid (p-tolylacetic acid), 3-methylphenylacetic acid (m-tolylacetic acid), 2-methylphenylacetic acid (o-tolylacetic acid), 2,4,6-trimethylphenylacetic acid (mesitylacetic acid), 4-isopropylphenylacetic acid (cumenylacetic acid), 4-n-propylphenylacetic acid, 3,5-dimethylphenylacetic acid, 2,5-dimethylphenylacetic acid, 3,4-dimethylphenylacetic acid, 2,4-dimethylphenylacetic acid, 4-n-butoxyphenylacetic acid, 4-n-propoxyphenylacetic acid, 4-ethoxyphenylacetic acid, 2-ethoxyphenylacetic acid, 4-n-butylphenylacetic acid, 4-isobutylphenylacetic acid, 4-tert-butylphenylacetic acid, 3,4-dimethoxyphenylacetic acid, 2,5-dimethoxyphenylacetic acid, 2,3-dimethoxyphenylacetic acid, 3,5-dimethoxy-phenylacetic acid, 2,4-dimethoxyphenylacetic acid, 2-(trifluoromethyl)-phenylacetic acid, 3-(trifluoromethyl)-phenylacetic acid, 4-(trifluoromethyl)-phenylacetic acid, 2-(trifluoromethoxy)-phenylacetic acid, 3-(trifluoromethoxy)-phenylacetic acid, 4-(trifluoromethoxy)-phenylacetic acid and 3,4-diethoxyphenylacetic acid.

Chloroformates also suitable for use in the synthesis (step (b) of the above method) of the compounds of the present invention include, but are not limited to, n-$C_{1-12}$ alkylchloroformates (e.g. methyl chloroformate, ethyl chloroformate, n-propyl chloroformate, n-butyl chloroformate, n-pentyl chloroformate, n-hexyl chloroformate, n-octyl chloroformate, n-decyl chloroformate and n-dodecyl chloroformate), $C_{3-8}$ cycloalkylchloroformates (e.g. cyclobutyl chloroformate, cyclopentyl chloroformate, and cyclohexyl chloroformate), arylchloroformates (e.g. phenyl chloroformate, m-tolyl chloroformate, p-tolyl chloroformate), and arylalkylchloroformates (e.g. phenylmethyl chloroformate).

The above method is able to provide compounds defined according to the above structural formula (I) and wherein $R_3$ is an amino-protecting group such as referred herein above or, in the presence of an additional final step, wherein $R_3$ is hydrogen.

Suitable experimental conditions for performing protection step (a) are well known in the art. An exemplary but non-limiting embodiment of the method of the invention includes a step (a) comprising reacting synephrine with an amino-protected thiazolidine-2-thione. Preferably, the amino-protected thiazolidine-2-thione or other amino-protecting reagent may be dissolved in an organic solvent such as an ether for use in said step (a), and is preferably used in a molar ratio of at least 1:1, more preferably from 1:1 to about 2:1, with respect to synephrine. Preferably the reaction of step (a) is performed in a solvent system which may comprise water, a lower alcohol (such as, but not limited to, methanol), and optionally in the presence of a further organic solvent (such as the solvent used for introducing the amino-protected thiazolidine-2-thione or other amino-protecting reagent).

When the amino-protected thiazolidine-2-thione used in step (a) is tert-butoxycarbonyl-thiazolidine-2-thione, step (a) results into a tert-butoxy-carbonyl-protected synephrine as an intermediate readily available, optionally without further purification, for the subsequent step (b).

In step (b), said N-protected synephrine is reacted with a suitable chloride for introducing the relevant substituent $R_1$. Suitable experimental conditions for performing acylation or sulfonation step (b), especially the molar ratio between the selected acylating or sulfonating agent and the N-protected synephrine are well known in the art and, depending upon the selected acylating or sulfonating agent, and the number of hydroxyl groups to be acylated or sulfonated, may be tailored at will without undue experimentation.

In step (c), said N-protected and acylated or sulfonated synephrine is reacted with a suitable activated carbonyl compound for introducing the relevant substituent $R_2$. Suitable experimental conditions for performing said step (c) are well known in the art and, depending upon the selected activated carbonyl compound, may be tailored at will without undue experimentation. It should be realized, however, that when $R_2$ is imidazolylcarbonyl or triazolylcarbonyl, a limited number of activated carbonyl compounds are available for efficiently introducing the substituent $R_2$. In the latter situation, the activated carbonyl compound should preferably be carbonyldiimidazole or, respectively, carbonylditriazole, both being well known for their selective activation capacity.

When compounds defined according to the above structural formula and wherein $R_3$ is hydrogen are desired, the above-referred general synthetic method preferably further comprises a step (d) for selectively deprotecting the amino group of the compound resulting from step (c), without affecting any of groups $R_1$ and $R_2$ being present in said compound. For instance the amino-protecting group may be removed by deprotection methods conventional in the art, such as:
  when the amino-protecting group is a phenylmethoxycarbonyl group, cleavage of the benzylic ether function by hydrogenolysis, e.g. using $H_2$, Pd-C at about 25° C., or under strongly acidic conditions (e.g. making use of bromhydric acid), or
  when the amino-protecting group is a tert-butoxycarbonyl group, by treatment with an acid, e.g. using aqueous hydrochloric acid or trifluoroacetic acid, under conditions mild enough to avoid further cleavage of the molecule, or
  when the amino-protecting group is a 9-fluorenylmethoxycarbonyl group, by treatment with a base such as piperidine.

As is well known in the art, the method of said step (d) may be capable of simultaneously achieving selective deprotection of the amino group and the formation of a non-toxic acid addition salt such as, but not limited to, a hydrochloride, a hydrobromide or a trifluoroacetate, of the compounds of the invention wherein $R_3$ is hydrogen. This particular aspect of the invention may be useful when the said compound is intended for formulation into a medicament since the water-solubility of the said salt is expected to be significantly higher than that of the corresponding free base form of said compound.

In another aspect, based on the fact that the above-defined novel synephrine derivatives exhibit biologically-active properties, the present invention relates to a pharmaceutical composition comprising a therapeutic effective amount of a compound defined by the above structural formula (with any of the available individual meanings for each of $R_1$, $R_2$ and $R_3$), and optionally one or more pharmaceutically acceptable carriers or excipients. Said pharmaceutical composition may comprise a novel synephrine derivative of the invention as the single bio-active ingredient, or as a bio-active ingredient in combination with one or more other drugs in a combined preparation for a so-called combination therapy.

The term "pharmaceutically acceptable carrier or excipient" as used herein in relation to pharmaceutical compositions and combined preparations means any material or substance with which the bio-active principle(s), i.e. the synephrine derivative and the said one or more other drugs, may be formulated in order to facilitate application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used in the form of concentrates, emulsions, solutions, granulates, dusts, sprays, aerosols, pellets or powders, but are not limited thereto.

Suitable pharmaceutical carriers or excipients for use in the said pharmaceutical compositions and their formulation are well known to those skilled in the art. There is no particular restriction to their selection within the present invention although, in case of a low or very low water-solubility of the synephrine derivative of this invention, special attention must be paid to the selection of suitable carrier combinations that can assist in a proper formulation in view of the expected time release profile. Suitable pharmaceutical carriers or excipients include additives such as, but not limited to, wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided that the same are consistent with standard pharmaceutical practice, i.e. carriers and additives which do not create severe and/or permanent damage to the mammal, in particular the human being, to be treated with said medicament. The pharmaceutical compositions of the present invention may be prepared by any method well known in the art, for instance by homogeneously mixing, dissolving, spray-drying, coating and/or grinding the bio-active ingredient(s), in a one-step or a multi-steps procedure, with the selected carrier material(s) and, where appropriate, the other additives such as surface-active agents. The pharmaceutical compositions of the present invention may also be prepared by micronisation, for instance in view to obtain them in the form of microspheres usually having a diameter of about 1 to about 10 μm, namely for the manufacture of microcapsules for controlled or sustained release of the said biologically-active ingredient(s).

Suitable surface-active agents useful as a pharmaceutically acceptable carrier or excipient in the pharmaceutical compositions of the present invention include non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, non-substituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, non-substituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants useful as pharmaceutically acceptable carriers or excipients in the pharmaceutical compositions of the present invention include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxy-polyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants useful as pharmaceutically acceptable carriers or excipients in the pharmaceutical compositions of the present invention include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further sub-stituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional carriers or excipients may be included in order to control the duration of action of the biologically-active ingredient(s) in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers or excipients for this purpose therefore include biocompatible aqueous buffers, ethanol, glycerol, propylene glycol, polyethylene glycol, complexing agents such as, but not limited to, cyclodextrins, maltodextrins and the like, and mixtures thereof.

In another embodiment, this invention provides combinations, preferably synergistic combinations, of one or more synephrine derivatives represented by the above structural formula with one or more biologically-active drugs being preferably selected from the group consisting of anti-inflammatory drugs. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22, 27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein-below, this principle may be applied to a number of desirable effects such as, but not limited to, an activity against inflammation. For instance the present invention relates to a pharmaceutical composition or combined preparation having synergistic effects against inflammation.

In yet another embodiment, this invention provides the use of a synephrine derivative represented by the above structural formula (with any of the available individual meanings for each of $R_1$, $R_2$ and $R_3$) for the manufacture of a medicament for preventing or treating an inflammatory disease or disorder. The compounds of the present invention have anti-inflammatory, analgesic and antipyretic activities comparable with glucocorticoids, but without side effects thereof, and are therefore safely useful in methods of treating or preventing diseases or conditions in which NF-κB and/or its target genes such as but not limited to IL-6, IL-8 and E-selectin are implicated. Such diseases and conditions include, but are not limited to, those in which inflammation or tissue injury is involved such as osteoarthritis, rheumatoid arthritis, ankylosing spondilytis and the like, as well as other rheumatologic or pain indications. Other diseases in which inflammation is involved and for which the novel compounds of the present invention are therapeutically useful include, but are not limited to, asthma, psoriasis, septic shock and inflammatory bowel disease. Other diseases in which inflammation is involved and for which the novel compounds of the present invention are osteoporosis. Since NF-κB may also be involved in apoptosis, the compounds of the present invention are also useful to limit tissue and/or cell damage and for ischaemic disease, neural injury or myocardial infarction. The compounds of the invention are also useful in the treatment or prevention of Alzheimer's disease by delaying the onset or slowing the progression of said disease.

In view of the above methods of treatment or prevention, the aforementioned compounds of the invention (with any of the available individual meanings for each of $R_1$, $R_2$ and $R_3$) or pharmaceutical compositions (formulations) thereof may be administered by any conventional method including oral and parenteral (e.g. subcutaneous, intraperitoneal, intra-vascular or intramuscular) injection. The treatment may consist of a single dose or a plurality of doses of the bio-active ingredient over a predetermined period of time.

Thus, the present invention involves a method of treating a patient having inflammation or an inflammation-related disorder by the administration of a therapeutically effective amount of a novel synephrine compound of the present invention. The invention is therefore useful for, but not limited to, the treatment of inflammation in a patient, and for treatment of other inflammation-associated disorders such as pain, headache or fever. The compounds of the present invention are also useful to treat arthritis, including but not limited to rheumatoid arthritis, spondyloarthritis, gouty arthritis, osteoarthritis, systemic lupus erythematosus, and juvenile arthritis. The compounds of the present invention are also useful to treat osteoporosis. The compounds of the present invention are also useful in the treatment of asthma, bronchitis, menstrual cramps, tendinitis, bursitis, and skin-related conditions such as psoriasis, eczema, acne, burns and dermatitis. Moreover, the compounds of the present invention are useful for the treatment of gastrointestinal inflammatory conditions such as, but not limited to, inflammatory bowel disease, Crohn's disease, gastritis, irritable bowel syndrome and ulcerative colitis. The compounds of the present invention are also useful in the treatment or prevention of inflammatory effects of cancer, such as colorectal cancer, breast cancer, prostate cancer or leukemia. The compounds of the present invention are further useful in treating inflammation in diseases such as vascular diseases, migraine, headache, periarteritis nodosa, thyroiditis, plastic anemia, Hodgkin's disease, chroniclymphocytic leukemia, scleroderma, rheumatic fever, type I diabetes, myasthenia gravis, multiple sclerosis, sarcoidosis, nephrotic syndrome, Bechet's syndrome, polymyositis, gingivitis, myocardial ischemia and the like. In addition, the compounds of the present invention are useful in the treatment of inflammatory effects of ophthalmic diseases such as retinitis, retinopathy, conjunctivitis, uveitis, ocular photophobia, and acute injury to the eye tissue. The compounds of the present invention are also useful in the treatment of pulmonary inflammation, such as one associated with viral infection or cystic fibrosis. The compounds of the present invention are further useful for the treatment of certain central nervous system disorders such as, but not limited to, cortical dementia, Alzheimer's disease, and multiple sclerosis. The compounds of the present invention are also useful in the treatment of allergic rhinitis, respiratory distress syndrome, endotoxin shock syndrome, atherosclerosis and central nervous system damage resulting from stroke, ischemia or trauma. Besides being useful for human treatment, the compounds of the present invention are also useful for the treatment of higher mammals, including pets and cattle such as, but not limited to, horses, dogs, cats, sheep and pigs.

The term "therapeutically-effective" as used herein refers to an amount of the bio-active agent for use in anti-inflammation therapy which achieves improvement in inflammation severity, as may be determined by any practical or reproducible method. For oral administration, the pharmaceutical composition of this invention may be in the form of a dosage unit containing a predetermined amount of the bio-active ingredient. Examples of such dosage units are tablets or capsules.

The therapeutically active amount of compound that can be administered and the dosage regimen for treating an inflammatory disease condition with a compound and/or pharmaceutical composition of this invention depends on a variety of factors, including the age, weight, sex and medical condition of the patient, the severity of the disease, the route and frequency of administration, and the particular compound used, and thus may vary in accordance with said factors.

The pharmaceutical composition may contain the bio-active ingredient of this invention in a range from about 0.1 to about 2000 mg, preferably about 0.5 to 500 mg and more preferably about 1 to 100 mg per dosage unit. A daily dose of about 0.01 to 100 mg/kg body weight, preferably about 0.1 to 20 mg/kg body weight and more preferably about 0.1 to 10 mg/kg body weight, may be appropriate for administration to a human being. The daily dose may suitably be administered in one to four sub-doses per day. In the case of psoriasis and other skin inflammatory conditions, it may be preferred to apply a topical preparation of the compound of this invention to the affected area two to four times per day.

The following examples are provided for illustration of the invention without limiting its scope in any way, and will be explained with reference to the general scheme 1 below.

Scheme 1

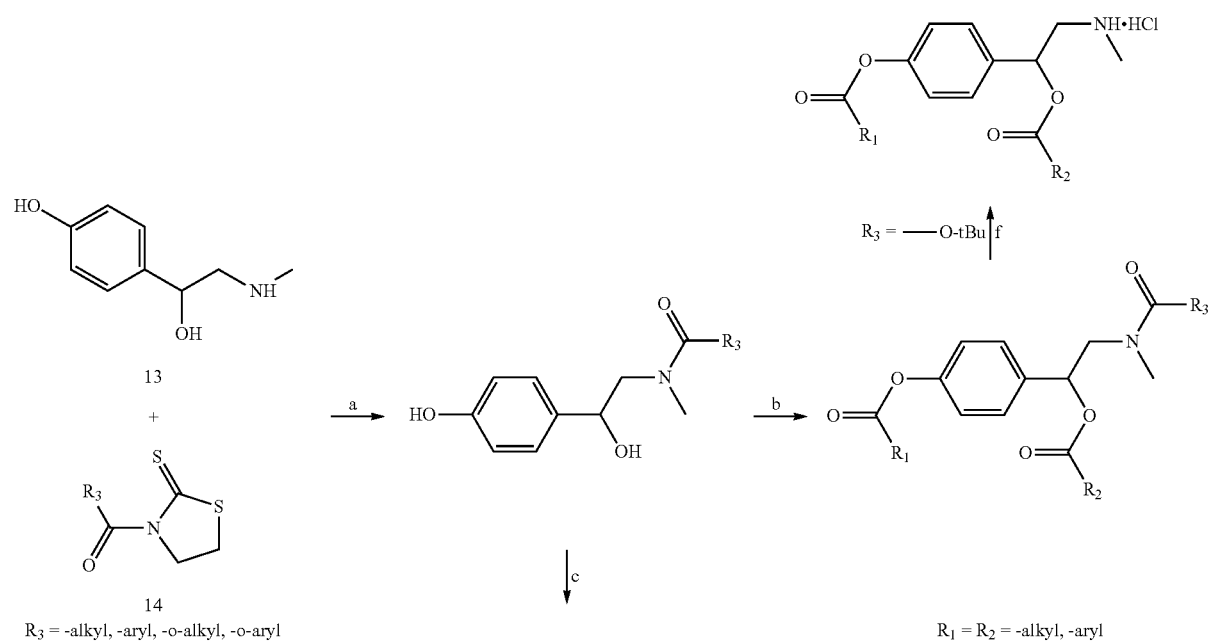

-continued

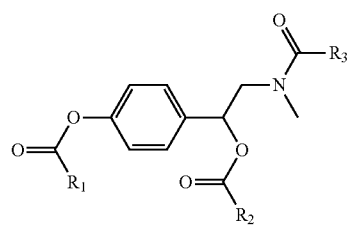
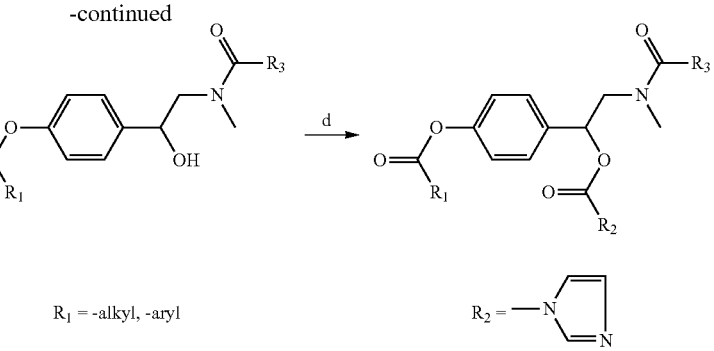

Example 1

Preparation of a N-Protected Synephrine

The following refers to the preparation of N-protected synephrines according to scheme 1, step a.

Synephrine (referred as 13 in the above scheme 1) (1.65 g, 9.87 mmol) was dissolved in a boiling mixture of water (25 ml) and methanol (12 ml). This hot solution was stirred vigorously, and then a yellow solution of a N-acyl thiazolidine-2-thione (referred to as 14 in the above scheme 1; for the purpose of the present example N-acetyl-thiazolidine-2-thione (14a) was used) (1.592 g, 9.87 mmol) in THF (10 ml) was added portion-wise. Disappearance of the yellow color was nearly instantaneous, however in order to ensure complete reaction, triethyl amine (202 mg, 2 mmol) was added, and after 10 minutes the resulting colorless solution was cooled to 40° C. and concentrated under reduced pressure onto a rotary evaporator. The crude product was purified by column chromatography using 200 g of silica gel and eluting with 300 ml of a 98:2 (volume ratio) $CH_2Cl_2$-methanol mixture, followed by a 94:6 (volume ratio) $CH_2Cl_2$-methanol mixture. The desired product (1.40 g, yield 72%) may be re-crystallized from ethyl acetate.

Example 2

Preparation of N-Boc-Synephrine: tert-butyl[2-hydroxy-2-(4-hydroxyphenyl)ethyl]methylcarbamate Synthesis of N-Boc Synephrine was carried out as described in example 1 but using N-tert-butyloxycarbonyl thiazolidine-2-thione (N-Boc-thiazolidine-2-thione) as the N-acyl thiazolidine-2-thione. N-Boc-thiazolidine-2-thione may be easily obtained by reacting di-tert-butyl dicarbonate with 1,3-thiazolidine-2-thione preferably in the presence of an organic base such as triethylamine.

One molar equivalent of N-Boc thiazolidine-2-thione was added to a boiling solution of synephrine in methanol and water followed by one molar equivalent of triethyl amine. The solution was maintained at 70° C. The crude resulting product was purified by column chromatography using a mixture of $CH_2Cl_2$ and MeOH in a volume to volume ratio of 98:2, to yield 85% of the pure crystalline material.

Example 3

Preparation of N-Protected-di-O-acyl-Synephrines

The following refers to the preparation of N-protected-di-O-acyl-synephrines according to scheme 1, step b.

Dry methylene chloride (17 ml) and triethylamine (346 mg, 3.42 mmol) were added to a 50 ml round bottom flask containing the N-protected synephrine obtained in example 1 (1.71 mmol). This mixture was stirred at room temperature until a slightly turbid solution was obtained. The flask was placed under nitrogen pressure and immersed into an ice bath. An acyl chloride (3.42 mmol) was then added drop-wise within four minutes to the chilled solution. The ice bath was removed two minutes after addition was completed, and the reaction solution was stirred at room temperature for 43 hours. The reaction flask was chilled in an ice bath, and addition of 0.25 equivalent of triethylamine followed by drop-wise addition of 0.25 equivalent of the same acyl chloride was carried out. After one hour, thin layer chromatography (TLC) analysis (performed with a 98:2 (volume ratio) $CH_2Cl_2$/methanol mixture indicated that reaction was complete. The reaction solution was diluted with methylene chloride and extracted with a half-saturated $NaHCO_3$ solution. The organic layer was dried over anhydrous $MgSO_4$, filtered and concentrated into an oil. The crude material obtained was purified by column chromatography (100 g silica gel, 98:2 (volume ratio) $CH_2Cl_2$/methanol mixture) to afford the desired product with a yield of about 70%.

Example 4

Preparation of 4-{2-[(tert-butoxycarbonyl)(methyl)amino]-1-hydroxyethyl}phenyl benzoate The following refers in general to the preparation of N-protected synephrine derivatives according to scheme 1, step c.

To a N-protected synephrine, in particular for the purpose of the present example N—BOC synephrine as obtained in example 2 (1.75 mmole) dissolved in 6 ml methanol was added solid potassium hydroxide (85 mg, 1.516 mmole). The mixture was stirred until full KOH dissolution, then methanol was removed under reduced pressure. The resulting residue was dried under vacuum, placed under a nitrogen atmosphere and then stirred in 3 ml of dry DMF. Once dissolution was effected, benzoyl chloride (1.516 mmole) was added drop-wise so that only slight warming was observed. TLC analysis with a 96:4 (volume ratio) $CH_2Cl_2$-methanol mixture showed that reaction was completed within 15 minutes. Eventually, the reaction mixture was diluted with methylene chloride and extracted with water. The organic layer was dried over anhydrous $MgSO_4$, filtered, concentrated and, in order to ensure full DMF removal, dried under high vacuum. The resulting crystalline crude material was purified by column chromatography (90 g silica gel, elution with 200 ml of a $CH_2Cl_2$- methanol mixture (volume ratio progressively ranging from 99:1 to 96:4). The desired product (409 mg) was obtained with a 73% yield.

Examples 5 to 7

Preparation of 4-{2-[(tert-butoxycarbonyl)(methyl)amino]1-hydroxyethyl}phenyl isobutyrate: 4-{2-[(tert-butoxycarbonyl)(methyl)amino]-1-hydroxyethyl}phenyl hexanoate: and 4-{2-[(tert-butoxycarbonyl)(methyl)-amino]-1-hydroxyethyl}phenyl 1-naphthoate A flask containing a stirring bar was purged with nitrogen and charged with N-Boc synephrine (obtained in example 2). The flask was fitted with a rubber septum and placed under nitrogen pressure. Dry methylene chloride (10 ml) and triethyl amine (1.05 molar equivalents) were added. Once dissolution was complete, the flask containing the slightly turbid solution was immersed in an ice bath. After sufficient cooling, the appropriate acyl chloride (1 molar equivalent; for the purpose of the example respectively isobutyryl chloride, hexanoyl chloride and 1-naphthoyl chloride) was added dropwise to the stirred solution. Once addition was complete, the ice bath was removed after several minutes, and the clear solution was stirred at room temperature. The progress of the reaction was monitored by TLC on silica using a mixture of $CH_2Cl_2$ and MeOH at 98/2 (v/v). After completion of the reaction was noted, the reaction solution was diluted with methylene chloride, and the resulting solution was extracted first with water and then saturated NaCl. The organic phase was dried over MgSO4, filtered and concentrated on the rotary evaporator. The crude material was purified by silica gel column chromatography eluting the final compound with 98/2, CH2Cl2/MeOH (v/v). In this way the following compounds were obtained:
- 4-{2-[(tert-butoxycarbonyl)(methyl)amino]-1-hydroxyethyl}phenyl isobutyrate (example 5) in 92% yield;
- 4-{2-[(tert-butoxycarbonyl)(methyl)amino]-1-hydroxyethyl}phenyl hexanoate (example 6) in 82% yield; and
- 4-{2-[(tert-butoxycarbonyl)(methyl)amino]-1-hydroxyethyl}phenyl 1-naphthoate (example 7) in 89% yield.

Example 8

Synthesis of 1-[4-(benzoyloxy)phenyl]-2-[(tert-butoxycarbonyl)-methylamino]ethyl-1H-imidazole-1-carboxylate The following refers in general to the preparation of N-protected synephrine derivatives according to scheme 1, step d. 2-[4-(benzoyloxy)phenyl]-2-hydroxy-1-[N-(tert-butoxycarbonyl)-methylamino]ethane (50 mg, 0.135 mmol) prepared in example 4 was weighed into a flask equipped with a stirring bar, and the system was purged with nitrogen. Dry methylene chloride (1 ml) was added, and the mixture was stirred until a solution was obtained. To this solution, at room temperature, was added 1,1'-carbonyldiimidazole (hereinafter referred as CDI, 23 mg, 0.142 mmol). Reaction progress was monitored by TLC analysis. Additional portions of CDI were introduced after stirring for 3 hours (6.5 mg, 0.04 mmol), 4.5 hours (6 mg, 0.037 mmol) and 6.5 hours (3.5 mg, 0.022 mmol). After 7.5 hours, the reaction solution was diluted with methylene chloride, and the resulting solution was extracted two times with water. The organic layer was dried over anhydrous $MgSO_4$, filtered and concentrated under reduced pressure, and the residue was dried in vacuo. The desired product was obtained quantitatively (yield: 100%).

Examples 9 to 11

Preparation of 1-[4-(isobutanoyloxy)phenyl]-2-[(tert-butoxycarbonyl)-methylamino]ethyl-1H-imidazole-1-carboxylate, 1-[4-(hexanoyloxy)phenyl]-2-[(tert-butoxycarbonyl)-methylamino]ethyl-1H-imidazole-1-carboxylate and 1-[4-(naphthoyloxy)phenyl]-2-[(tert-butoxy-carbonyl)-methylamino]ethyl-1H-imidazole-1-carboxylate The synthesis of 1-[4-(isobutanoyloxy)phenyl]-2-[(tert-butoxycarbonyl)-methylamino]ethyl-1H-imidazole-1-carboxylate (example 9), 1-[4-(hexanoyloxy)phenyl]-2-[(tert-butoxycarbonyl)-methylamino]ethyl-1H-imidazole-1-carboxylate (example 10) and 1-[4-(naphthoyloxy)phenyl]-2-[(tert-butoxycarbonyl)-methylamino]ethyl-1H-imidazole-1-carboxylate (example 11) was carried out as described in example 8, starting from the compounds of examples 5 to 7 respectively. The title products were all obtained in quantitative yield (higher than 98%).

Example 12

Preparation of 4-[1-(acetyloxy)-2-(methylamino)ethyl]phenyl acetate hydrochloride The following refers to the preparation of di-O-acyl-synephrine salts according to scheme 1, step f. A compound obtained according to example 3 (0.246 mmol) was dissolved in 1 ml of 4M HCl in dioxane, and the resulting solution was stirred at room temperature for 1 hour. TLC analysis (performed with a 98:2 (volume ratio) $CH_2Cl_2$/methanol mixture) after one hour indicated complete disappearance of the starting material. The solution was then diluted with ethyl ether, and the resulting cloudy solution was purged with $N_2$ in order to remove HCl. Upon standing 1 hour at room temperature the reaction solution became clear and product white beads deposited. Ether washing was repeated four times. The resulting desired product was dried under vacuum and obtained (60 mg) in a 85% yield.

Example 13

Biological Evaluation of 4-{2-[(tert-butoxycarbonyl)(methyl)-amino]-1-hydroxyethyl}phenyl hexanoate with pE-selectine-Luc transfected cells L929sA cells were cultured in DMEM supplemented with 5% new-born calf serum and 5% fetal calf serum, 100 units/ml penicillin and 0.1 mg/ml streptomycin. L929sA mouse fibroblast cells were stably transfected with pE-selectine-Luc (also referred to as pELAM-luc) by the calcium phosphate precipitation procedure described by De Bosscher et al. in *Proc. Natl. Acad. Sci. USA* (1997) 94, 13504-13509. The co-transfected plasmid pPGKβGeobpA, conferring resistance to G418 and expressing constitutive β-galactosidase enzymatic activity, was used as an internal control. L929sA cells were transiently transfected by the DEAE-dextran transfection method described by De Bosscher et al. (cited supra).

Recombinant murine tumor necrosis factor (TNF) was produced according to a method standard in the art. Dexamethasone (hereinafter abbreviated as DEX) commercially available from Sigma, and 2-(4-acetoxyphenyl)-2-chloro-N-methyl-ethylammonium chloride (hereinafter abbreviated as compound A) was synthesized according to Louw et al. in *Biochemical Pharmacology* (1997) 53, 189-197). A stock solution was prepared in ethanol (for DEX) or DMSO (for both comparative compound A and for the compound of example 6 according to this invention, i.e. 1-[4-(benzoyloxy)phenyl]-2-[(tert-butoxy-carbonyl)-methylamino]ethyl-1H-imidazole-1-carboxylate), aliquoted and stored at −70° C. Control experiments verified that the final concentration of organic solvent did not interfere with any of the assays.

Induction was performed in triplicate for each independent experiment, which was carried out at least twice. Induction with DEX, compound A, and for the compound of example 6 according to this invention at 1 µM, 10 µM or respectively any other indicated concentration were performed at −2 hours for a total of 8 hours, while TNF (2000 IU/ml) was added at time point zero and left on the cells for 6 hours. After induction, cells were lysed with a lysis buffer (commercially available from Tropix, Bedford, Massachussets) and samples were assayed according to the manufacturer's instructions (Promega Biotech).

In order to investigate whether the inhibitory effect of compound A or the compound of example 6 according to this invention is directed at the transcriptional level of NF-κB-driven genes, the NF-κB-dependent physiological promoter construct, pE-selectin-Luc stably integrated into L929sA cells, was tested. Inhibition of TNF-induced gene expression by the mediation of the compound of example 6 according to this invention was observed in a dose-responsive manner, as shown in FIG. 1. DEX-mediated and compound A-mediated inhibition of TNF-induced gene expression were used as controls (FIG. 1). In the appended figures, NI stands for non-induced (either in presence of solvent controls like ethanol or DMSO).

Example 14

Biological Evaluation of 1-[4-(isobutanoyloxy)phenyl]-2-[(tert-butoxycarbonyl)-methyl-amino]-ethyl-1H-imidazole-1-carboxylate and 1-[4-(naphthoyloxy)phenyl]-2-[(tert-butoxycarbonyl)-methylamino]ethyl-1H-imidazole-1-carboxylate with p(IL6-kB)$_3$-50hu.IL6P-luc+transfected cells L929sA mouse fibroblast cells were cultured in DMEM supplemented with 5% newborn calf serum and 5% FCS, 100 units/ml penicillin and 0.1 mg/ml streptomycin. The L929sA mouse fibroblast cells were stably transfected with plasmid p(1L6-kB)$_3$-50hu.IL6P-luc+ by a calcium phosphate precipitation procedure well known in the art. The co-transfected plasmid pPGKβGeobpA, conferring resistance to G418 and expressing constitutive b-galactosidase enzymatic activity, was used as an internal control.

TNF, Dexamethasone, and compound A were obtained and handled as described for example 13.

Inductions were performed in triplicate for each independent experiment, which was carried out at least twice. Inductions with DEX, compound A or synephrine derivatives of the present invention at 1 mM, 10 mM or at the indicated concentrations respectively, were performed at −2 hours for a total of 8 hours, while TNF (2000 IU/ml) was added at time point zero and left on the cells for 6 hours. Synephrine derivatives tested according to this protocol included 1-[4-(isobutanoyloxy)phenyl]-2-[(tert-butoxycarbonyl)-methyl-amino]-ethyl-1H-imidazole-1-carboxylate (compound of example 9), and 1-[4-(naphthoyloxy)phenyl]-2-[(tert-butoxycarbonyl)-methylamino]ethyl-1H-imidazole-1-carboxylate (compound of example 11).

After induction with TNF, cells were lysed with a lysis buffer (commercially available from TROPIX, Bedford, Massachussets) and samples were assayed for their protein or β-galactosidase content and luciferase activity according to the manufacturer's instructions (Promega Biotech).

In order to demonstrate that these synephrine derivatives are anti-inflammatory agents, and that their mechanism of action is directed at the transcriptional level of NF-kB-driven genes (with NF-kB being widely acknowledged as a key regulatory transcription factor driving inflammatory cytokine gene expression), we tested the recombinant NF-kB-driven promoter construct p(IL6-kB)$_3$-50hu.IL6P-luc+, stably integrated into L929sA cells, and observed for specific and selected synephrine derivatives an inhibition of the pro-inflammatory TNF-induced gene expression in a dose-responsive manner. FIG. 1 further illustrates the anti-inflammatory effect of 1-[4-(isobutanoyloxy)phenyl]-2-[(tert-butoxycarbonyl)-methylamino]ethyl-1H-imidazole-1-carboxylate (referred to in FIG. 1 as Isobut). Dexamethasone and compound A (referred to as DEX and CpdA respectively) were used as positive control based on their known anti-inflammatory effect. As a negative control, solvent control (solvent Ctrl) was performed as well.

From the results of the reporter gene assay in FIG. 1 it is observed that, as expected, the cytokine TNF can stimulate the E-selectin promoter (almost a factor 8) and importantly, that DEX (1 microM) and CpdA (10 microM) inhibit the expression of E-selectin, reflecting their anti-inflammatory activity. both Isobut and Benz are able to effectively inhibit TNF-induced E-selectin gene induction.

It was thus observed that the synephrine derivatives of this invention display a marked anti-inflammatory potential. The anti-inflammatory effectiveness of the active compounds are comparable to the effectiveness obtained by using known anti-inflammatory compounds such as dexamethasone or compound A.

Examples 15 to 90

Preparation of 4-{2-[(tert-butoxycarbonyl)(methyl) amino]-1-hydroxyethyl}phenyl substituted benzoates The procedure of example 4 is repeated, except that benzoyl chloride is replaced with a substituted benzoyl chloride. The following 4-{2-[(tert-butoxycarbonyl)(methyl)amino]-1-hydroxyethyl}phenyl substituted benzoates are obtained with similar yields:

4-{2-[(tert-butoxycarbonyl)(methyl)amino]-1-hydroxyethyl}phenyl p-anisoate (example 15) starting from p-anisoyl-chloride, 4-{2-[(tert-butoxycarbonyl)(methyl)amino]-1-hydroxyethyl}phenyl 2-bromo-benzoate (example 16) starting from 2-bromobenzoyl chloride, 4-{2-[(tert-butoxycarbonyl)(methyl)amino]-1-hydroxyethyl}phenyl 4-bromo-benzoate (example 17) starting from 4-bromobenzoyl chloride, 4-{2-[(tert-butoxycarbonyl)(methyl)amino]-1-hydroxyethyl}phenyl 3-chloro-benzoate (example 18) starting from 3-chlorobenzoyl chloride, 4-{2-[(tert-butoxycarbonyl)(methyl)amino]-1-hydroxyethyl}phenyl pentafluoro-benzoate (example 19) starting from pentafluorobenzoyl chloride, 4-{2-[(tert-butoxycarbonyl)(methyl)amino]-1-hydroxyethyl}phenyl 2-chloro-benzoate (example 20) starting from 2-chlorobenzoyl chloride, 4-{2-[(tert-butoxycarbonyl)(methyl)amino]-1-hydroxyethyl}phenyl p-toluate (example 21) starting from p-toluoyl chloride, 4-{2-[(tert-butoxycarbonyl)(methyl)amino]-1-hydroxyethyl}phenyl 4-chloro-benzoate (example 22) starting from 4-chlorobenzoyl chloride, 4-{2-[(tert-butoxycarbonyl)(methyl)amino]-1-hydroxyethyl}phenyl 2,4-dichlorobenzoate (example 23) starting from 2,4-dichlorobenzoyl chloride, 4-{2-[(tert-butoxycarbonyl)(methyl)amino]-1-hydroxyethyl}phenyl 3,4-dichlorobenzoate (example 24) starting from 3,4-dichlorobenzoyl chloride, 4-{2-[(tert-butoxycarbonyl)(methyl)amino]-1-hydroxyethyl}phenyl 4-nitroben-zoate (example 25) starting from 4-nitrobenzoyl chloride, 4-{2-[(tert-butoxycarbonyl)(methyl)amino]-1-hydroxyethyl}phenyl 4-fluoro-benzoate (example 26) starting from 4-fluorobenzoyl chloride, 4-{2-[(tert-butoxycarbonyl)(methyl)amino]-1-hydroxyethyl}phenyl 2-fluoro-benzoate (example 27) starting from 2-fluorobenzoyl chloride, 4-{2-[(tert-butoxycarbonyl)(methyl)amino]-1-hydroxyethyl}phenyl o-toluate (example 28) starting from o-toluoyl chloride, 4-{2-[(tert-butoxycarbonyl)(methyl)amino]-1-hydroxyethyl}phenyl m-toluate (example 29) starting from m-toluoyl chloride, 4-{2-[(tert-butoxycarbonyl)(methyl)amino]-1-hydroxyethyl}phenyl 4-cyano-benzoate (example 30) starting from 4-cyanobenzoyl chloride, 4-{2-[(tert-butoxycarbonyl)(methyl)amino]-1-hydroxyethyl}phenyl 3-nitroben-zoate (example 31) starting from 3-nitrobenzoyl chloride, 4-{2-[(tert-butoxycarbonyl)(methyl)amino]-1-hydroxyethyl}phenyl 4-tert-butylbenzoate (example 32) starting from 4-tert-butyl-benzoyl chloride, 4-{2-[(tert-butoxycarbonyl)(methyl)amino]-1-hydroxyethyl}phenyl 4-phenyl-benzoate (example 33) starting from 4-biphenylcarbonyl chloride, 4-{2-[(tert-butoxycarbonyl)(methyl)amino]-1-hydroxyethyl}phenyl 3,5-dimethoxybenzoate (example 34) starting from 3,5-dimethoxybenzoyl chloride, 4-{2-[(tert-butoxycarbonyl)(methyl)amino]-1-hydroxyethyl}phenyl 3-fluoro-benzoate (example 35) starting from 3-fluorobenzoyl chloride, 4-{2-[(tert-butoxycarbonyl)(methyl)amino]-1-hydroxyethyl}phenyl 2,6-dichlorobenzoate (example 36) starting from 2,6-dichlorobenzoyl chloride, 4-{2-[(tert-butoxycarbonyl)(methyl)amino]-1-hydroxyethyl}phenyl 4-butyl-benzoate (example 37) starting from 4-butylbenzoyl chloride, 4-{2-[(tert-butoxycarbonyl)(methyl)amino]-1-hydroxyethyl}phenyl 4-heptyl-oxybenzoate (example 38) starting from 4-heptyloxybenzoyl chloride, 4-{2-[(tert-butoxycarbonyl)(methyl)amino]-1-hydroxyethyl}phenyl 4-hexyl-benzoate (example 39) starting from 4-hexylbenzoyl chloride, 4-{2-[(tert-butoxycarbonyl)(methyl)amino]-1-hydroxyethyl}phenyl 4-hexyl-oxybenzoate (example 40) starting from 4-hexyloxybenzoyl chloride, 4-{2-[(tert-butoxycarbonyl)(methyl)amino]-1-hydroxyethyl}phenyl 4-pentyl-benzoate (example 41) starting from 4-pentylbenzoyl chloride, 4-{2-[(tert-butoxycarbonyl)(methyl)amino]-1-hydroxyethyl}phenyl m-anisoate (example 42) starting from m-anisoyl chloride, 4-{2-[(tert-butoxycarbonyl)(methyl)amino]-1-hydroxyethyl}phenyl 2,6-difluoro-benzoate (example 43) starting from 2,6-difluorobenzoyl chloride, 4-{2-[(tert-butoxycarbonyl)(methyl)amino]-1-hydroxyethyl}phenyl 2-nitro-benzoate (example 44) starting from 2-nitrobenzoyl chloride, 4-{2-[(tert-butoxycarbonyl)(methyl)amino]-1-hydroxyethyl}phenyl 4-chloro-3-nitrobenzoate (example 45) starting from 4-chloro-3-nitrobenzoylchloride, 4-{2-[(tert-butoxycarbonyl)(methyl)amino]-1-hydroxyethyl}phenyl 3,4-difluoro-benzoate (example 46) starting from 3,4-difluorobenzoyl chloride, 4-{2-[(tert-butoxycarbonyl)(methyl)amino]-1-hydroxyethyl}phenyl 2-iodo-benzoate (example 47) starting from 2-iodobenzoyl chloride, 4-{2-[(tert-butoxycarbonyl)(methyl)amino]-1-hydroxyethyl}phenyl o-anisoate (example 48) starting from o-anisoyl chloride, 4-{2-[(tert-butoxycarbonyl)(methyl)amino]-1-hydroxyethyl}phenyl 2,4-difluoro-benzoate (example 49) starting from 2,4-difluorobenzoyl chloride, 4-{2-[(tert-butoxycarbonyl)(methyl)amino]-1-hydroxyethyl}phenyl benzoate (example 50) starting from 4-(trifluoromethyl)benzoyl chloride, 4-{2-[(tert-butoxycarbonyl)(methyl)amino]-1-hydroxyethyl}phenyl 3-(chloro-methyl)benzoate (example 51) starting from 3-(chloromethyl)-benzoyl chloride, 4-{2-[(tert-butoxycarbonyl)(methyl)amino]-1-hydroxyethyl}phenyl 4-(chloro-methyl)benzoate (example 52) starting from 4-(chloromethyl)-benzoyl chloride, 4-{2-[(tert-butoxycarbonyl)(methyl)amino]-1-hydroxyethyl}phenyl 3-(dichloro-methyl)benzoate (example 53) starting from 3-(dichloromethyl)-benzoyl chloride, 4-{2-[(tert-butoxycarbonyl)(methyl)amino]-1-hydroxyethyl}phenyl 2,3,4,5-tetrafluorobenzoate (example 54) starting from 2,3,4,5-tetrafluorobenzoyl chloride, 4-{2-[(tert-butoxycarbonyl)(methyl)amino]-1-hydroxyethyl}phenyl 2,4,6-trichlorobenzoate (example 55) starting from 2,4,6-trichlorobenzoyl chloride, 4-{2-[(tert-butoxycarbonyl)(methyl)amino]-1-hydroxyethyl}phenyl 2,3,4-trifluorobenzoate (example 56) starting from 2,3,4-trifluorobenzoyl chloride, 4-{2-[(tert-butoxycarbonyl)(methyl)amino]-1-hydroxyethyl}phenyl 2,4,6-trifluorobenzoate (example 57) starting from 2,4,6-trifluorobenzoyl chloride, 4-{2-[(tert-butoxycarbonyl)(methyl)amino]-1-hydroxyethyl}phenyl 4-bromo-2-fluorobenzoate (example 58) starting from 4-bromo-2-fluoro-benzoyl chloride, 4-{2-[(tert-butoxycarbonyl)(methyl)amino]-1-hydroxyethyl}phenyl 2,3,5,6-tetrafluorobenzoate (example 59) starting from 2,3,5,6-tetrafluorobenzoyl chloride, 4-{2-[(tert-butoxycarbonyl)(methyl)amino]-1-hydroxyethyl}phenyl 3,5-dinitrobenzoate (example 60) starting from 3,5-dinitrobenzoyl chloride, 4-{2-[(tert-butoxycarbonyl)(methyl)amino]-1-hydroxyethyl}phenyl 4-heptyl-benzoate (example 61) starting from 4-heptylbenzoyl chloride, 4-{2-[(tert-butoxycarbonyl)(methyl)amino]-1-hydroxyethyl}phenyl 4-iodobenzoate (example 62) starting from 4-iodobenzoyl chloride, 4-{2-[(tert-butoxycarbonyl)(methyl)amino]-1-hydroxyethyl}phenyl 4-octyl-benzoate (example 63) starting from 4-octylbenzoyl chloride, 4-{2-[(tert-butoxycarbonyl)(methyl)amino]-1-hydroxyethyl}phenyl 4-pentyl-oxybenzoate (example 64) starting from 4-pentyloxybenzoyl chloride, 4-{2-[(tert-butoxycarbonyl)(methyl)amino]-1-hydroxyethyl}phenyl 4-phenyl-azobenzoate (example 65) starting from 4-phenylazobenzoyl chloride, 4-{2-[(tert-butoxycarbonyl)(methyl)amino]-1-hydroxyethyl}phenyl 4-propyl-benzoate (example 66) starting from 4-propylbenzoyl chloride, 4-{2-[(tert-butoxycarbonyl)(methyl)amino]-1-hydroxyethyl}phenyl benzoate (example 67) starting from 3,5-dichlorobenzoyl chloride, 4-{2-[(tert-butoxycarbonyl)(methyl)amino]-1-hydroxyethyl}phenyl 3-fluoro-4-(trifluoromethyl)benzoate (example 68) starting from 3-fluoro-4-(trifluoromethyl)benzoyl chloride, 4-{2-[(tert-butoxycarbonyl)(methyl)amino]-1-hydroxyethyl}phenyl 2,6-dimethoxybenzoate (example 69) starting from 2,6-dimethoxybenzoyl chloride, 4-{2-[(tert-butoxycarbonyl)(methyl)amino]-1-hydroxyethyl}phenyl piperonylate (example 70) starting from piperonyloyl chloride, 4-{2-[(tert-butoxycarbonyl)(methyl)amino]-1-hydroxyethyl}phenyl 2,4-dimethoxybenzoate (example 71) starting from 2,4-dimethoxybenzoyl chloride, 4-{2-[(tert-butoxycarbonyl)(methyl)amino]-1-hydroxyethyl}phenyl 4-(thien-2-yl)benzoate (example 72) starting from 4-(thien-2-yl)-benzoyl chloride, 4-{2-[(tert-butoxycarbonyl)(methyl)amino]-1-hydroxyethyl}phenyl 4-(1,2,3-thiadiazol-4-yl)benzoate (example 73) starting from 4-(1,2,3-thiadiazol-4-yl)benzoyl chloride, 4-{2-[(tert-butoxycarbonyl)(methyl)amino]-1-hydroxyethyl}phenyl 4-(1H-pyrazol-1-yl)benzoate (example 74) starting from 4-(1H-pyrazol-1-yl)benzoyl chloride, 4-{2-[(tert-butoxycarbonyl)(methyl)amino]-1-hydroxyethyl}phenyl 4-[3-(trifluoromethyl)-1H-pyrazol-1-yl]-benzoate (example 75) starting from 4-[3-(trifluoromethyl)-1H-pyrazol-1-yl]-benzoyl chloride, 4-{2-[(tert-butoxycarbonyl)(methyl)amino]-1-hydroxyethyl}phenyl 5-bromo-2,3,4-trimethylbenzoate (example 76) starting from 5-bromo-2,3,4-trimethylbenzoyl chloride, 4-{2-[(tert-butoxycarbonyl)(methyl)amino]-1-hydroxyethyl}phenyl 2-chloro-4-fluorobenzoate (example 77) starting from 2-chloro-4-fluorobenzoyl chloride, 4-{2-[(tert-butoxycarbonyl)(methyl)amino]-1-hydroxyethyl}phenyl 5,5,8,8-tetramethyl-5,6,7,8-tetrahydro-2-naphthoate (example 78) starting from 5,5,8,8-tetramethyl-5,6,7,8-tetrahydro-2-naphthalene-carbonyl chloride, 4-{2-[(tert-butoxycarbonyl)(methyl)amino]-1-hydroxyethyl}phenyl 2,3-difluorobenzoate (example 79) starting from 2,3-difluorobenzoyl chloride, 4-{2-[(tert-butoxycarbonyl)(methyl)amino]-1-hydroxyethyl}phenyl 2-fluoro-5-(trifluoromethyl)benzoate (example 80) starting from 2-fluoro-5-(trifluoromethyl)benzoyl chloride, 4-{2-[(tert-butoxycarbonyl)(methyl)amino]-1-hydroxyethyl}phenyl 2,3,6-trifluorobenzoate (example 81) starting from 2,3,6-trifluorobenzoyl chloride, 4-{2-[(tert-butoxycarbonyl)(methyl)amino]-1-hydroxyethyl}phenyl 3-fluoro-4-methylbenzoate (example 82) starting from 3-fluoro-4-methylbenzoyl chloride, 4-{2-[(tert-butoxycarbonyl)(methyl)amino]-1-hydroxyethyl}phenyl 3-cyclopentoxy-4-methoxybenzoate (example 83) starting from 3-cyclopentoxy-4-methoxybenzoyl chloride, 4-{2-[(tert-butoxycarbonyl)(methyl)amino]-1-hydroxyethyl}phenyl 4-fluoro-3-(trifluoromethyl)benzoate (example 84) starting from 4-fluoro-3-(trifluoromethyl)benzoyl chloride, 4-{2-[(tert-butoxycarbonyl)(methyl)amino]-1-hydroxyethyl}phenyl 3-(2-methyl-thiazol-4-yl)-benzoate (example 85) starting from 3-(2-methyl-thiazol-4-yl)-benzoyl chloride, 4-{2-[(tert-butoxycarbonyl)(methyl)amino]-1-hydroxyethyl}phenyl 2,4,6-trimethylbenzoate (example 86) starting from 2,4,6-trimethylbenzoyl chloride, 4-{2-[(tert-butoxycarbonyl)(methyl)amino]-1-hydroxyethyl}phenyl 2-(thien-2-yl)benzoate (example 87) starting from 2-(thien-2-yl)benzoyl chloride, 4-{2-[(tert-butoxycarbonyl)(methyl)amino]-1-hydroxyethyl}phenyl 3-cyano-benzoate (example 88) starting from 3-cyanobenzoyl chloride, 4-{2-[(tert-butoxycarbonyl)(methyl)amino]-1-hydroxyethyl}phenyl 3-(5-methyl-1,2,4-oxadiazol-3-yl)-benzoate (example 89) starting from 3-(5-methyl-1,2,4-oxadiazol-3-yl)-benzoyl chloride, and 4-{2-[(tert-butoxycarbonyl)(methyl)amino]-1-hydroxyethyl}phenyl 4-(5-methyl-1,2,4-oxadiazol-3-yl)-benzoate (example 90) starting from 4-(5-methyl-1,2,4-oxadiazol-3-yl)-benzoyl chloride.

Examples 91 to 103

Preparation of 4-{2-[(tert-butoxy-carbonyl)(methyl)amino]-1-hydroxyethyl}phenyl alkanoates, cycloalkanoates and cycloalkylalkanoates The procedure of examples 5 and 6 is repeated, except that isobutyryl chloride or hexanoyl chloride is replaced with another alkanoyl or cycloalkanoyl or cycloalkylalkanoyl chloride. The following 4-{2-[(tert-butoxycarbonyl)(methyl) amino]-1-hydroxyethyl}phenyl alkanoates, cycloalkanoates and cycloalkylalkanoates are obtained with similar yields:

4-{2-[(tert-butoxycarbonyl)(methyl)amino]-1-hydroxyethyl}phenyl octanoate (example 91) starting from octanoyl chloride;

4-{2-[(tert-butoxycarbonyl)(methyl)amino]-1-hydroxyethyl}phenyl pivaloate (example 92) starting from pivaloyl chloride;

4-{2-[(tert-butoxycarbonyl)(methyl)amino]-1-hydroxyethyl}phenyl isovalerate (example 93) starting from isovaleryl chloride;

4-{2-[(tert-butoxycarbonyl)(methyl)amino]-1-hydroxyethyl}phenyl valerate (example 94) starting from valery chloride;

4-{2-[(tert-butoxycarbonyl)(methyl)amino]-1-hydroxyethyl}phenyl butyrate (example 95) starting from butyryl chloride;

4-{2-[(tert-butoxycarbonyl)(methyl)amino]-1-hydroxyethyl}phenyl propanoate (example 96) starting from propionyl chloride;

4-{2-[(tert-butoxycarbonyl)(methyl)amino]-1-hydroxyethyl}phenyl acetate (example 97) starting from acetyl chloride;

4-{2-[(tert-butoxycarbonyl)(methyl)amino]-1-hydroxyethyl}phenyl trichloroacetate (example 98) starting from trichloroacetyl chloride;

4-{2-[(tert-butoxycarbonyl)(methyl)amino]-1-hydroxyethyl}phenyl cyclopropanoate (example 99) starting from cyclopropanecarbonyl chloride;

4-{2-[(tert-butoxycarbonyl)(methyl)amino]-1-hydroxyethyl}phenyl 3-cyclopentylpropanoate (example 100) starting from 3-cyclopentylpropionyl chloride;

4-{2-[(tert-butoxycarbonyl)(methyl)amino]-1-hydroxyethyl}phenyl cyclobutanoate (example 101) starting from cyclobutanecarbonyl chloride;

4-{2-[(tert-butoxycarbonyl)(methyl)amino]-1-hydroxyethyl}phenyl cyclohexanoate (example 102) starting from cyclohexanecarbonyl chloride; and 4-{2-[(tert-butoxycarbonyl)(methyl)amino]-1-hydroxyethyl}phenyl cyclopentanoate (example 103) starting from cyclopentanecarbonyl chloride.

Examples 104 to 155

Preparation of 2-[4-(phenylacetyloxy)phenyl]-2-hydroxy-1-[N-(tert-butoxycarbonyl)-methylamino]ethane and analogues thereof The procedure of example 4 is repeated, except that benzoyl chloride is replaced with an optionally substituted phenylacetyl chloride. The following 2-[4-(phenylacetyloxy)phenyl]-2-hydroxy-1-[N-(tert-butoxycarbonyl)-methylamino]ethanes are obtained with similar yields:

2-[4-(phenylacetyloxy)phenyl]-2-hydroxy-1-[N-(tert-butoxycarbonyl)-methylamino]ethane (example 104) starting from phenylacetyl chloride, 2-[4-(4-methoxyphenylacetyloxy)phenyl]-2-hydroxy-1-[N-(tert-butoxycarbonyl)-methylamino]ethane (example 105) starting from 4-methoxyphenylacetyl chloride, 2-[4-(4-chlorophenylacetyloxy)phenyl]-2-hydroxy-1-[N-(tert-butoxycarbonyl)-methylamino]ethane (example 106) starting from 4-chlorophenylacetyl chloride, 2-[4-(3-methoxyphenylacetyloxy)phenyl]-2-hydroxy-1-[N-(tert-butoxycarbonyl)-methylamino]ethane (example 107) starting from 3-methoxyphenylacetyl chloride, 2-[4-(4-fluorophenylacetyloxy)phenyl]-2-hydroxy-1-[N-(tert-butoxycarbonyl)-methylamino]ethane (example 108) starting from 4-fluorophenylacetyl chloride, 2-[4-(phenylpropionyloxy)phenyl]-2-hydroxy-1-[N-(tert-butoxycarbonyl)-methylamino]ethane (example 109) starting from phenylpropionyl chloride, 2-[4-(4-methoxyphenyl propionyloxy)phenyl]-2-hydroxy-1-[N-(tert-butoxycarbonyl)-methylamino]ethane (example 110) starting from 4-methoxyphenylpropionyl chloride, 2-[4-(2-fluorophenylpropionyloxy)phenyl]-2-hydroxy-1-[N-(tert-butoxycarbonyl)-methylamino]ethane (example 111) starting from 2-fluorophenylpropionyl chloride, 2-[4-(phenylbutyryloxy)phenyl]-2-hydroxy-1-[N-(tert-butoxycarbonyl)-methylamino]ethane (example 112) starting from 2-phenylbutyryl chloride, 2-[4-(4-bromophenylacetyloxy)phenyl]-2-hydroxy-1-[N-(tert-butoxycarbonyl)-methylamino]ethane (example 113) starting from 4-bromophenylacetic acid chloride, 2-[4-(3-bromophenylacetyloxy)phenyl]-2-hydroxy-1-[N-(tert-butoxycarbonyl)-methylamino]ethane (example 114) starting from 3-bromophenylacetic acid chloride, 2-[4-(2-bromophenylacetyloxy)phenyl]-2-hydroxy-1-[N-(tert-butoxycarbonyl)-methylamino]ethane (example 115) starting from 2-bromophenylacetic acid chloride, 2-[4-(3-chlorophenylacetyloxy)phenyl]-2-hydroxy-1-[N-(tert-butoxycarbonyl)-methylamino]ethane (example 116) starting from 3-chlorophenylacetic acid chloride, 2-[4-(2-chlorophenylacetyloxy)phenyl]-2-hydroxy-1-[N-(tert-butoxycarbonyl)-methylamino]ethane (example 117) starting from 2-chlorophenylacetic acid chloride, 2-[4-(3-fluorophenylacetyloxy)phenyl]-2-hydroxy-1-[N-(tert-butoxycarbonyl)-methylamino]ethane (example 118) starting from 3-fluorophenylacetic acid chloride, 2-[4-(2-fluorophenylacetyloxy)phenyl]-2-hydroxy-1-[N-(tert-butoxycarbonyl)-methylamino]ethane (example 119) starting from 2-fluorophenylacetic acid chloride, 2-[4-(4-nitrophenylacetyloxy)phenyl]-2-hydroxy-1-[N-(tert-butoxycarbonyl)-methylamino]ethane (example 120) starting from 4-nitrophenylacetic acid chloride, 2-[4-(3-nitrophenylacetyloxy)phenyl]-2-hydroxy-1-[N-(tert-butoxycarbonyl)-methylamino]ethane (example 121) starting from 3-nitrophenylacetic acid chloride, 2-[4-(2-nitrophenylacetyloxy)phenyl]-2-hydroxy-1-[N-(tert-butoxycarbonyl)-methylamino]ethane (example 122) starting from 2-nitrophenylacetic acid chloride, 2-[4-(2,4-dichlorophenylacetyloxy)phenyl]-2-hydroxy-1-[N-(tert-butoxycarbonyl)-methylamino]ethane (example 123) starting from 2,4-dichlorophenylacetic acid chloride, 2-[4-(2,6-dichlorophenylacetyloxy)phenyl]-2-hydroxy-1-[N-(tert-butoxycarbonyl)-methylamino]ethane (example 124) starting from 2,6-dichlorophenylacetic acid chloride, 2-[4-(3,4-dichlorophenylacetyloxy)phenyl]-2-hydroxy-1-[N-(tert-butoxycarbonyl)-methylamino]ethane (example 125) starting from 3,4-dichlorophenylacetic acid chloride, 2-[4-(2-methoxyphenylacetyloxy)phenyl]-2-hydroxy-1-[N-(tert-butoxycarbonyl)-methylamino]ethane (example 126) starting from 2-methoxyphenylacetic acid chloride, 2-[4-(4-methylphenylacetyloxy)phenyl]-2-hydroxy-1-[N-(tert-butoxycarbonyl)-methylamino]ethane (example 127) starting from 4-methylphenylacetic acid chloride, 2-[4-(3-methyl phenylacetyloxy)phenyl]-2-hydroxy-1-[N-(tert-butoxycarbonyl)-methylamino]ethane (example 128) starting from 3-methylphenylacetic acid chloride, 2-[4-(2-methyl phenylacetyloxy)phenyl]-2-hydroxy-1-[N-(tert-butoxycarbonyl)-methylamino]ethane (example 129) starting from 2-methylphenylacetic acid chloride, 2-[4-(2,4,6-trimethylphenylacetyloxy)phenyl]-2-hydroxy-1-[N-(tert-butoxycarbonyl)-methylamino]ethane (example 130) starting from 2,4,6-trimethylphenylacetic acid chloride, 2-[4-(4-isopropyl phenylacetyloxy)phenyl]-2-hydroxy-1-[N-(tert-butoxycarbonyl)-methylamino]ethane (example 131) starting from 4-isopropylphenylacetic acid chloride, 2-[4-(4-n-propyl phenylacetyloxy)phenyl]-2-hydroxy-1-[N-(tert-butoxycarbonyl)-methylamino]ethane (example 132) starting from 4-n-propylphenylacetic acid chloride, 2-[4-(phenylacetyloxy)phenyl]-2-hydroxy-1-[N-(tert-butoxycarbonyl)-methylamino]ethane (example 133) starting from 3,5-dimethylphenylacetic acid chloride, 2-[4-(2,5-dimethylphenylacetyloxy)phenyl]-2-hydroxy-1-[N-(tert-butoxycarbonyl)-methylamino]ethane (example 134) starting from 2,5-dimethylphenylacetic acid chloride, 2-[4-(3,4-dimethylphenylacetyloxy)phenyl]-2-hydroxy-1-[N-(tert-butoxycarbonyl)-methylamino]ethane (example 135) starting from 3,4-dimethylphenylacetic acid chloride, 2-[4-(2,4-dimethylphenylacetyloxy)phenyl]-2-hydroxy-1-[N-(tert-butoxycarbonyl)-methylamino]ethane (example 136) starting from 2,4-dimethylphenylacetic acid chloride, 2-[4-(4-n-butoxyphenylacetyloxy)phenyl]-2-hydroxy-1-[N-(tert-butoxycarbonyl)-methylamino]ethane (example 137) starting from 4-n-butoxyphenylacetic acid chloride, 2-[4-(4-n-propoxyphenylacetyloxy)phenyl]-2-hydroxy-1-[N-(tert-butoxycarbonyl)-methylamino]ethane (example 138) starting from 4-n-propoxyphenylacetic acid chloride, 2-[4-(4-ethoxyphenylacetyloxy)phenyl]-2-hydroxy-1-[N-(tert-butoxycarbonyl)-methylamino]ethane (example 139) starting from 4-ethoxyphenylacetic acid chloride, 2-[4-(2-ethoxyphenylacetyloxy)phenyl]-2-hydroxy-1-[N-(tert-butoxycarbonyl)-methylamino]ethane (example 140) starting from 2-ethoxyphenylacetic acid chloride, 2-[4-(4-n-butylphenylacetyloxy)phenyl]-2-hydroxy-1-[N-(tert-butoxycarbonyl)-methylamino]ethane (example 141) starting from 4-n-butylphenylacetic acid chloride, 2-[4-(4-isobutylphenylacetyloxy)phenyl]-2-hydroxy-1-[N-(tert-butoxy-carbonyl)-methylamino]ethane (example 142) starting from 4-isobutylphenylacetic acid chloride, 2-[4-(4-tert-butylphenylacetyloxy)phenyl]-2-hydroxy-1-[N-(tert-butoxy-carbonyl)-methylamino]ethane (example 143) starting from 4-tert-butylphenylacetic acid chloride, 2-[4-(3,4-dimethoxyphenylacetyloxy)phenyl]-2-hydroxy-1-[N-(tert-butoxy-carbonyl)-methylamino]ethane (example 144) starting from 3,4-dimethoxyphenylacetic acid chloride, 2-[4-(2,5-dimethoxyphenylacetyloxy)phenyl]-2-hydroxy-1-[N-(tert-butoxy-carbonyl)-methylamino]ethane (example 145) starting from 2,5-dimethoxyphenylacetic acid chloride, 2-[4-(2,3-dimethoxyphenylacetyloxy)phenyl]-2-hydroxy-1-[N-(tert-butoxy-carbonyl)-methylamino]ethane (example 146) starting from 2,3-dimethoxyphenylacetic acid chloride, 2-[4-(3,5-dimethoxyphenylacetyloxy)phenyl]-2-hydroxy-1-[N-(tert-butoxy-carbonyl)-methylamino]ethane (example 147) starting from 3,5-dimethoxy-phenylacetic acid chloride, 2-[4-(2,4-dimethoxyphenylacetyloxy)phenyl]-2-hydroxy-1-[N-(tert-butoxy-carbonyl)-methylamino]ethane (example 148) starting from 2,4-dimethoxyphenylacetic acid chloride, 2-[4-(2-(trifluoromethyl)-phenylacetyloxy)phenyl]-2-hydroxy-1-[N-(tert-butoxy-carbonyl)-methylamino]ethane (example 149) starting from 2-(trifluoromethyl)-phenylacetic acid chloride, 2-[4-(3-(trifluoromethyl)-phenylacetyloxy)phenyl]-2-hydroxy-1-[N-(tert-butoxy-carbonyl)-methylamino]ethane (example 150) starting from 3-(trifluoromethyl)-phenylacetic acid chloride, 2-[4-(4-(trifluoromethyl)-phenylacetyloxy)phenyl]-2-hydroxy-1-[N-(tert-butoxycarbonyl)-methylamino]ethane (example 151) starting from 4-(trifluoromethyl)-phenyl acetic acid chloride, 2-[4-(2-(trifluoromethoxy)-phenylacetyloxy)phenyl]-2-hydroxy-1-[N-(tert-butoxycarbonyl)-methylamino]ethane (example 152) starting from 2-(trifluoromethoxy)-phenylacetic acid chloride, 2-[4-(3-(trifluoromethoxy)-phenylacetyloxy)phenyl]-2-hydroxy-1-[N-(tert-butoxycarbonyl)-methylamino]ethane (example 153) starting from 3-(trifluoromethoxy)-phenylacetic acid chloride, 2-[4-(4-(trifluoromethoxy)-phenylacetyloxy)phenyl]-2-hydroxy-1-[N-(tert-butoxycarbonyl)-methylamino]ethane (example 154) starting from 4-(trifluoromethoxy)-phenylacetic acid chloride, and 2-[4-(3,4-diethoxyphenylacetyloxy)phenyl]-2-hydroxy-1-[N-(tert-butoxycarbonyl)-methylamino]ethane (example 155) starting from 3,4-diethoxyphenylacetic acid chloride.

Examples 156 to 275

Preparation of 4-{2-[(tert-butoxycarbonyl)(methyl)amino]-1-hydroxyethyl}phenyl benzenesulfonate and analogues thereof The procedure of example 4 is repeated, except that benzoyl chloride is replaced with an optionally substituted phenylsulfonyl chloride. The following 4-{2-[(tert-butoxycarbonyl)(methyl)amino]-1-hydroxyethyl}phenyl benzenesulfonates are obtained with similar yields:

4-{2-[(tert-butoxycarbonyl)(methyl)amino]-1-hydroxyethyl}phenyl 4-fluoro-benzenesulfonate (example 156) starting from 4-fluorobenzenesulfonyl chloride, 4-{2-[(tert-butoxycarbonyl)(methyl)amino]-1-hydroxyethyl}phenyl 2-mesitylenesulfonate (example 157) starting from 2-mesitylenesulfonyl chloride, 4-{2-[(tert-butoxycarbonyl)(methyl)amino]-1-hydroxyethyl}phenyl 4-methoxy-benzenesulfonate (example 158) starting from 4-methoxybenzenesulfonyl chloride, 4-{2-[(tert-butoxycarbonyl)(methyl)amino]-1-hydroxyethyl}phenyl p-toluene-sulfonate (example 159) starting from p-toluenesulfonyl chloride, 4-{2-[(tert-butoxycarbonyl)(methyl)amino]-1-hydroxyethyl}phenyl pentafluoro-benzenesulfonate (example 160) starting from pentafluorobenzenesulfonyl chloride, 4-{2-[(tert-butoxycarbonyl)(methyl)amino]-1-hydroxyethyl}phenyl benzene-sulfonate (example 161) starting from benzenesulfonyl chloride, 4-{2-[(tert-butoxycarbonyl)(methyl)amino]-1-hydroxyethyl}phenyl 4-bromo-benzenesulfonate (example 162) starting from 4-bromobenzenesulfonyl chloride, 4-{2-[(tert-butoxycarbonyl)(methyl)amino]-1-hydroxyethyl}phenyl 2,4,6-triisopropylbenzenesulfonate (example 163) starting from 2,4,6-triisopropylbenzenesulfonyl chloride, 4-{2-[(tert-butoxycarbonyl)(methyl)amino]-1-hydroxyethyl}phenyl 2-naphthalenesulfonate (example 164) starting from 2-naphthalenesulfonylchloride, 4-{2-[(tert-butoxycarbonyl)(methyl)amino]-1-hydroxyethyl}phenyl 4-chlorobenzenesulfonate (example 165) starting from 4-chloro-benzenesulfonyl chloride, 4-{2-[(tert-butoxycarbonyl)(methyl)amino]-1-hydroxyethyl}phenyl 3,5-dichloro-2-hydroxybenzenesulfonate (example 166) starting from 3,5-dichloro-2-hydroxybenzenesulfonyl chloride, 4-{2-[(tert-butoxycarbonyl)(methyl)amino]-1-hydroxyethyl}phenyl 2,5-dichlorobenzenesulfonate (example 167) starting from 2,5-dichloro-benzenesulfonyl chloride, 4-{2-[(tert-butoxycarbonyl)(methyl)amino]-1-hydroxyethyl}phenyl 1-naphthalenesulfonate (example 168) starting from 1-naphthalenesulfonylchloride, 4-{2-[(tert-butoxycarbonyl)(methyl)amino]-1-hydroxyethyl}phenyl 4-tert-butylbenzenesulfonate (example 169) starting from 4-tert-butylbenzenesulfonyl chloride, 4-{2-[(tert-butoxycarbonyl)(methyl)amino]-1-hydroxyethyl}phenyl 3-(trifluoromethyl)-benzenesulfonate (example 170) starting from 3-(trifluoromethyl)-benzenesulfonyl chloride, 4-{2-[(tert-butoxycarbonyl)(methyl)amino]-1-hydroxyethyl}phenyl 2-bromobenzenesulfonate (example 171) starting from 2-bromobenzenesulfonyl chloride, 4-{2-[(tert-butoxycarbonyl)(methyl)amino]-1-hydroxyethyl}phenyl 4-acetylbenzenesulfonate (example 172) starting from 4-acetylbenzene-sulfonylchloride, 4-{2-[(tert-butoxycarbonyl)(methyl)amino]-1-hydroxyethyl}phenyl 2-(trifluoromethyl)-benzenesulfonate (example 173) starting from 2-(trifluoromethyl)-benzenesulfonyl chloride, 4-{2-[(tert-butoxycarbonyl)(methyl)amino]-1-hydroxyethyl}phenyl 3,4-dichlorobenzenesulfonate (example 174) starting from 3,4-dichlorobenzenesulfonyl chloride, 4-{2-[(tert-butoxycarbonyl)(methyl)amino]-1-hydroxyethyl}phenyl 3,4-dimethoxybenzenesulfonate (example 175) starting from 3,4-dimethoxybenzenesulfonyl chloride, 4-{2-[(tert-butoxycarbonyl)(methyl)amino]-1-hydroxyethyl}phenyl 3-chlorobenzenesulfonate (example 176) starting from 3-chlorobenzenesulfonyl chloride, 4-{2-[(tert-butoxycarbonyl)(methyl)amino]-1-hydroxyethyl}phenyl 2-chloro-4-fluorobenzenesulfonate (example 177) starting from 2-chloro-4-fluorobenzenesulfonyl chloride, 4-{2-[(tert-butoxycarbonyl)(methyl)amino]-1-hydroxyethyl}phenyl 3,5-dichlorobenzenesulfonate (example 178) starting from 3,5-dichlorobenzenesulfonyl chloride, 4-{2-[(tert-butoxycarbonyl)(methyl)amino]-1-hydroxyethyl}phenyl 3-chloro-4-fluorobenzenesulfonate (example 179) starting from 3-chloro-4-fluorobenzenesulfonyl chloride, 4-{2-[(tert-butoxycarbonyl)(methyl)amino]-1-hydroxyethyl}phenyl 2,4-dichlorobenzenesulfonate (example 180) starting from 2,4-dichlorobenzenesulfonyl chloride, 4-{2-[(tert-butoxycarbonyl)(methyl)amino]-1-hydroxyethyl}phenyl 2,5-dimethoxybenzenesulfonate (example 181) starting from 2,5-dimethoxybenzenesulfonyl chloride, 4-{2-[(tert-butoxycarbonyl)(methyl)amino]-1-hydroxyethyl}phenyl 3-bromobenzenesulfonate (example 182) starting from 3-bromo-benzenesulfonyl chloride, 4-{2-[(tert-butoxycarbonyl)(methyl)amino]-1-hydroxyethyl}phenyl 2,3-dichlorobenzenesulfonate (example 183) starting from 2,3-dichlorobenzenesulfonyl chloride, 4-{2-[(tert-butoxycarbonyl)(methyl)amino]-1-hydroxyethyl}phenyl 5-fluoro-2-methylbenzenesulfonate (example 184) starting from 5-fluoro-2-methylbenzenesulfonyl chloride, 4-{2-[(tert-butoxycarbonyl)(methyl)amino]-1-hydroxyethyl}phenyl 3-fluorobenzenesulfonate (example 185) starting from 3-fluorobenzenesulfonyl chloride, 4-{2-[(tert-butoxycarbonyl)(methyl)amino]-1-hydroxyethyl}phenyl 2,3,5,6-tetramethylbenzenesulfonate (example 186) starting from 2,3,5,6-tetramethylbenzenesulfonyl chloride, 4-{2-[(tert-butoxycarbonyl)(methyl)amino]-1-hydroxyethyl}phenyl 3-chloro-2-methylbenzenesulfonate (example 187) starting from 3-chloro-2-methylbenzenesulfonyl chloride, 4-{2-[(tert-butoxycarbonyl)(methyl)amino]-1-hydroxyethyl}phenyl 2,5-dibromo-3,6-difluorobenzenesulfonate (example 188) starting from 2,5-dibromo-3,6-difluoro-benzenesulfonyl chloride, 4-{2-[(tert-butoxycarbonyl)(methyl)amino]-1-hydroxyethyl}phenyl 2,6-difluorobenzenesulfonate (example 189) starting from 2,6-difluorobenzenesulfonyl chloride, 4-{2-[(tert-butoxycarbonyl)(methyl)amino]-1-hydroxyethyl}phenyl 2-chlorobenzenesulfonate (example 190) starting from 2-chloro-benzenesulfonyl chloride, 4-{2-[(tert-butoxycarbonyl)(methyl)amino]-1-hydroxyethyl}phenyl 5-bromo-2-methoxybenzenesulfonate (example 191) starting from 5-bromo-2-methoxybenzenesulfonyl chloride, 4-{2-[(tert-butoxycarbonyl)(methyl)amino]-1-hydroxyethyl}phenyl 5-chloro-2-methoxybenzenesulfonate (example 192) starting from 5-chloro-2-methoxybenzenesulfonyl chloride, 4-{2-[(tert-butoxycarbonyl)(methyl)amino]-1-hydroxyethyl}phenyl 2,4-difluorobenzenesulfonate (example 193) starting from 2,4-difluorobenzenesulfonyl chloride, 4-{2-[(tert-butoxycarbonyl)(methyl)amino]-1-hydroxyethyl}phenyl 2-cyanobenzenesulfonate (example 194) starting from 2-cyano-benzenesulfonyl chloride, 4-{2-[(tert-butoxycarbonyl)(methyl)amino]-1-hydroxyethyl}phenyl 2-chloro-5-(trifluoromethyl)- benzenesulfonate (example 195) starting from 2-chloro-5-(trifluoromethyl)-benzenesulfonyl chloride, 4-{2-[(tert-butoxycarbonyl)(methyl)amino]-1-hydroxyethyl}phenyl 4-bromobenzenesulfonate (example 196) starting from 4-bromomethylbenzenesulfonyl chloride, 4-{2-[(tert-butoxycarbonyl)(methyl)amino]-1-hydroxyethyl}phenyl 2,4-dimethoxybenzenesulfonate (example 197) starting from 2,4-dimethoxybenzenesulfonyl chloride, 4-{2-[(tert-butoxycarbonyl)(methyl)amino]-1-hydroxyethyl}phenyl 4-chloro-3-nitrobenzenesulfonate (example 198) starting from 4-chloro-3-nitrobenzenesulfonyl chloride, 4-{2-[(tert-butoxycarbonyl)(methyl)amino]-1-hydroxyethyl}phenyl 3-nitrobenzenesulfonate (example 199) starting from 3-nitro-benzenesulfonyl chloride, 4-{2-[(tert-butoxycarbonyl)(methyl)amino]-1-hydroxyethyl}phenyl 4-nitro-benzenesulfonate (example 200) starting from 4-nitrobenzenesulfonyl chloride, 4-{2-[(tert-butoxycarbonyl)(methyl)amino]-1-hydroxyethyl}phenyl 2-(methyl-sulfonyl)-benzenesulfonate (example 201) starting from 2-(methylsulfonyl)-benzenesulfonyl chloride, 4-{2-[(tert-butoxycarbonyl)(methyl)amino]-1-hydroxyethyl}phenyl 4-(methyl-sulfonyl)-benzenesulfonate (example 202) starting from 4-(methylsulfonyl)-benzenesulfonyl chloride, 4-{2-[(tert-butoxycarbonyl)(methyl)amino]-1-hydroxyethyl}phenyl 2,4-dichloro-5-methylbenzenesulfonate (example 203) starting from 2,4-dichloro-5-methylbenzenesulfonyl chloride, 4-{2-[(tert-butoxycarbonyl)(methyl)amino]-1-hydroxyethyl}phenyl 4-(trifluoro-methoxy)-benzenesulfonate (example 204) starting from 4-(trifluoromethoxy)-benzenesulfonyl chloride, 4-{2-[(tert-butoxycarbonyl)(methyl)amino]-1-hydroxyethyl}phenyl 2-methoxy-4-nitrobenzenesulfonate (example 205) starting from 2-methoxy-4-nitrobenzenesulfonyl chloride, 4-{2-[(tert-butoxycarbonyl)(methyl)amino]-1-hydroxyethyl}phenyl 4-bromo-2-chlorobenzenesulfonate (example 206) starting from 4-bromo-2-chlorobenzenesulfonyl chloride, 4-{2-[(tert-butoxycarbonyl)(methyl)amino]-1-hydroxyethyl}phenyl 2,3-dihydro-1-benzofuran-5-sulfonate (example 207) starting from 2,3-dihydro-1-benzofuran-5-sulfonyl chloride, 4-{2-[(tert-butoxycarbonyl)(methyl)amino]-1-hydroxyethyl}phenyl 2,3-dihydro-1,4-benzodioxine-6-sulfonate (example 208) starting from 2,3-dihydro-1,4-benzodioxine-6-sulfonyl chloride, 4-{2-[(tert-butoxycarbonyl)(methyl)amino]-1-hydroxyethyl}phenyl 1,3-benzo-thiazole-6-sulfonyl (example 209) starting from 1,3-benzothiazole-6-sulfonyl chloride, 4-{2-[(tert-butoxycarbonyl)(methyl)amino]-1-hydroxyethyl}phenyl 2,1,3-benzothiadiazole 4 sulfonate (example 210) starting from 2,1,3-benzothiadiazole 4 sulfonyl chloride, 4-{2-[(tert-butoxycarbonyl)(methyl)amino]-1-hydroxyethyl}phenyl 2,1,3-benzothiadiazole-5-sulfonate (example 211) starting from 2,1,3-benzothiadiazole-5-sulfonyl chloride, 4-{2-[(tert-butoxycarbonyl)(methyl)amino]-1-hydroxyethyl}phenyl 2,1,3-benzoxadiazole-4-sulfonate (example 212) starting from 2,1,3-benzoxadiazole-4-sulfonyl chloride, 4-{2-[(tert-butoxycarbonyl)(methyl)amino]-1-hydroxyethyl}phenyl 3,4-dihydro-2H-1,5-benzodioxepine-7-sulfonate (example 213) starting from 3,4-dihydro-2H-1,5-benzodioxepine-7-sulfonyl chloride, 4-{2-[(tert-butoxycarbonyl)(methyl)amino]-1-hydroxyethyl}phenyl 4-methyl-3,4-dihydro-2H-1,4-benzoxazine-7-sulfonate (example 214) starting from 4-methyl-3,4-dihydro-2H-1,4-benzoxazine-7-sulfonyl chloride, 4-{2-[(tert-butoxycarbonyl)(methyl)amino]-1-hydroxyethyl}phenyl 4-(1,3-oxazol-5-yl)benzenesulfonate (example 215) starting from 4-(1,3-oxazol-5-yl)benzenesulfonyl chloride, 4-{2-[(tert-butoxycarbonyl)(methyl)amino]-1-hydroxyethyl}phenyl 4-(1,2,3-thiadiazol-4-yl)benzenesulfonate (example 216) starting from 4-(1,2,3-thiadiazol-4-yl)benzenesulfonyl chloride, 4-{2-[(tert-butoxycarbonyl)(methyl)amino]-1-hydroxyethyl}phenyl 4-(1H-pyrazol-1-yl)benzenesulfonate (example 217) starting from 4-(1H-pyrazol-1-yl)benzenesulfonyl chloride, 4-{2-[(tert-butoxycarbonyl)(methyl)amino]-1-hydroxyethyl}phenyl 4-(3-chloro-2-cyanophenoxy)benzene-1-sulfonate (example 218) starting from 4-(3-chloro-2-cyanophenoxy)benzene-1-sulfonyl chloride, 4-{2-[(tert-butoxycarbonyl)(methyl)amino]-1-hydroxyethyl}phenyl 4-bromo-2,5-difluoro-benzene-1-sulfonate (example 219) starting from 4-bromo-2,5-difluoro-benzene-1-sulfonyl chloride, 4-{2-[(tert-butoxycarbonyl)(methyl)amino]-1-hydroxyethyl}phenyl 4-(acetylamino)-3-chloro-benzene-1-sulfonate (example 220) starting from 4-(acetylamino)-3-chloro-benzene-1-sulfonyl chloride, 4-{2-[(tert-butoxycarbonyl)(methyl)amino]-1-hydroxyethyl}phenyl 3,5-di-(trifluoromethyl)-benzenesulfonate (example 221) starting from 3,5-di-(trifluoromethyl)-benzenesulfonyl chloride, 4-{2-[(tert-butoxycarbonyl)(methyl)amino]-1-hydroxyethyl}phenyl 2-fluorobenzenesulfonate (example 222) starting from 2-fluorobenzenesulfonyl chloride, 4-{2-[(tert-butoxycarbonyl)(methyl)amino]-1-hydroxyethyl}phenyl 4-methyl-3-nitrobenzene-1-sulfonate (example 223) starting from 4-methyl-3-nitrobenzene-1-sulfonyl chloride, 4-{2-[(tert-butoxycarbonyl)(methyl)amino]-1-hydroxyethyl}phenyl 5-chloro-2,1,3-benzoxadiazole-4-sulfonate (example 224) starting from 5-chloro-2,1,3-benzoxadiazole-4-sulfonyl chloride, 4-{2-[(tert-butoxycarbonyl)(methyl)amino]-1-hydroxyethyl}phenyl 3-(5-methyl-1,3,4-oxadiazol-2-yl)benzenesulfonate (example 225) starting from 3-(5-methyl-1,3,4-oxadiazol-2-yl)benzenesulfonyl chloride, 4-{2-[(tert-butoxycarbonyl)(methyl)amino]-1-hydroxyethyl}phenyl 4-bromo-2-(trifluoromethyl)-benzenesulfonate (example 226) starting from 4-bromo-2-(trifluoromethyl)-benzenesulfonyl chloride, 4-{2-[(tert-butoxycarbonyl)(methyl)amino]-1-hydroxyethyl}phenyl 2,2-dimethyl-6-chromanesulfonate (example 227) starting from 2,2-dimethyl-6-chromanesulfonyl chloride, 4-{2-[(tert-butoxycarbonyl)(methyl)amino]-1-hydroxyethyl}phenyl 4-(morpholino-4-sulfonyl)benzenesulfonate (example 228) starting from 4-(morpholino-4-sulfonyl)benzenesulfonyl chloride,
4-(pyrrolidine-1-sulfonyl)-benzenesulfonyl chloride, 4-{2-[(tert-butoxycarbonyl)(methyl)amino]-1-hydroxyethyl}phenyl 3-(2-methyl-4-pyrimidinyl)benzenesulfonate (example 229) starting from 3-(2-methyl-4-pyrimidinyl)benzenesulfonyl chloride, 4-{2-[(tert-butoxycarbonyl)(methyl)amino]-1-hydroxyethyl}phenyl 2-cyano-5-methylbenzenesulfonate (example 230) starting from 2-cyano-5-methylbenzenesulfonyl chloride, 4-{2-[(tert-butoxycarbonyl)(methyl)amino]-1-hydroxyethyl}phenyl 2,5-dimethylbenzenesulfonate (example 231) starting from 2,5-dimethylbenzenesulfonyl chloride, 4-{2-[(tert-butoxycarbonyl)(methyl)amino]-1-hydroxyethyl}phenyl 4-chloro-3-(trifluoromethyl)-benzenesulfonate (example 232) starting from 4-chloro-3-(trifluoromethyl)-benzenesulfonyl chloride, 4-{2-[(tert-butoxycarbonyl)(methyl)amino]-1-hydroxyethyl}phenyl 4-bromo-2-methyl-benzenesulfonate (example 233) starting from 4-bromo-2-methyl-benzenesulfonyl chloride, 4-{2-[(tert-butoxycarbonyl)(methyl)amino]-1-hydroxyethyl}phenyl 2-chloro-4-(trifluoro-methyl)-benzenesulfonate (example 234) starting from 2-chloro-4-(trifluoro-methyl)-benzenesulfonyl chloride, 4-{2-[(tert-butoxycarbonyl)(methyl)amino]-1-hydroxyethyl}phenyl 2-chloro-4-cyano-benzenesulfonate (example 235) starting from 2-chloro-4-cyano-benzenesulfonyl chloride, 4-{2-[(tert-butoxycarbonyl)(methyl)amino]-1-hydroxyethyl}phenyl 2,6-dichloro-4-(trifluoromethyl)-benzenesulfonate (example 236) starting from 2,6-dichloro-4-(trifluoromethyl)-benzenesulfonyl chloride, 4-{2-[(tert-butoxycarbonyl)(methyl)amino]-1-hydroxyethyl}phenyl 3,4-difluoro-benzenesulfonate (example 237) starting from 3,4-difluoro-benzene-1-sulfonyl chloride, 4-{2-[(tert-butoxycarbonyl)(methyl)amino]-1-hydroxyethyl}phenyl 2-iodobenzenesulfonate (example 238) starting from 2-iodobenzenesulfonyl chloride, 4-{2-[(tert-butoxycarbonyl)(methyl)amino]-1-hydroxyethyl}phenyl 4-methyl-1-naphthalenesulfonate (example 239) starting from 4-methyl-1-naphthalenesulfonyl chloride, 4-{2-[(tert-butoxycarbonyl)(methyl)amino]-1-hydroxyethyl}phenyl 4-(trifluoromethyl)-benzenesulfonate (example 240) starting from 4-(trifluoromethyl)-benzenesulfonyl chloride, 4-{2-[(tert-butoxycarbonyl)(methyl)amino]-1-hydroxyethyl}phenyl 2,6-dichloro-benzenesulfonate (example 241) starting from 2,6-dichloro-benzenesulfonyl chloride, 4-{2-[(tert-butoxycarbonyl)(methyl)amino]-1-hydroxyethyl}phenyl 2-(trifluoromethoxy)-benzenesulfonate (example 242) starting from 2-(trifluoromethoxy)-benzenesulfonyl chloride, 4-{2-[(tert-butoxycarbonyl)(methyl)amino]-1-hydroxyethyl}phenyl 4-cyano-benzenesulfonate (example 243) starting from 4-cyano-benzene-1-sulfonyl chloride, 4-{2-[(tert-butoxycarbonyl)(methyl)amino]-1-hydroxyethyl}phenyl 4-butoxybenzenesulfonate (example 244) starting from 4-butoxybenzene-1-sulfonyl chloride, 4-{2-[(tert-butoxycarbonyl)(methyl)amino]-1-hydroxyethyl}phenyl 2,3,4-trifluoro-benzenesulfonate (example 245) starting from 2,3,4-trifluoro-benzene-1-sulfonyl chloride, 4-{2-[(tert-butoxycarbonyl)(methyl)amino]-hydroxyethyl}phenyl 4-bromo-2-(trifluoromethoxy)-benzenesulfonate (example 246) starting from 4-bromo-2-(trifluoromethoxy)-benzene-1-sulfonyl chloride, 4-{2-[(tert-butoxycarbonyl)(methyl)amino]-1-hydroxyethyl}phenyl 3-cyano-benzenesulfonate (example 247) starting from 3-cyanobenzene-1-sulfonyl chloride, 4-{2-[(tert-butoxycarbonyl)(methyl)amino]-1-hydroxyethyl}phenyl 3-chloro-4-methyl-benzenesulfonate (example 248) starting from 3-chloro-4-methyl-benzene-1-sulfonyl chloride, 4-{2-[(tert-butoxycarbonyl)(methyl)amino]-1-hydroxyethyl}phenyl 4-bromo-2-ethyl-benzenesulfonate (example 249) starting from 4-bromo-2-ethyl-benzene-1-sulfonyl chloride, 4-{2-[(tert-butoxycarbonyl)(methyl)amino]-1-hydroxyethyl}phenyl 5,5,8,8-tetramethyl-5,6,7,8-tetrahydro-2-naphthalene-sulfonate (example 250) starting from 5,5,8,8-tetramethyl-5,6,7,8-tetrahydro-2-naphthalene-sulfonyl chloride, 4-{2-[(tert-butoxycarbonyl)(methyl)amino]-1-hydroxyethyl}phenyl 4-(2-chloro-6-nitrophenoxy)-benzenesulfonate (example 251) starting from 4-(2-chloro-6-nitrophenoxy)-benzene-1-sulfonyl chloride, 4-{2-[(tert-butoxycarbonyl)(methyl)amino]-1-hydroxyethyl}phenyl 3,5-dichloro-4-(2-chloro-4-nitrophenoxy)-benzenesulfonate (example 252) starting from 3,5-dichloro-4-(2-chloro-4-nitrophenoxy)-benzene-1-sulfonyl chloride, 4-{2-[(tert-butoxycarbonyl)(methyl)amino]-1-hydroxyethyl}phenyl 4-pentyl-benzenesulfonate (example 253) starting from 4-pentylbenzene-1-sulfonyl chloride, 4-{2-[(tert-butoxycarbonyl)(methyl)amino]-1-hydroxyethyl}phenyl 4-ethyl-benzenesulfonate (example 254) starting from 4-ethylbenzene-1-sulfonyl chloride, 4-{2-[(tert-butoxycarbonyl)(methyl)amino]-1-hydroxyethyl}phenyl 4-propyl-benzenesulfonate (example 255) starting from 4-propylbenzene-1-sulfonyl chloride, 4-{2-[(tert-butoxycarbonyl)(methyl)amino]-1-hydroxyethyl}phenyl 4-butyl-benzenesulfonate (example 256) starting from 4-butylbenzene-1-sulfonyl chloride, 4-{2-[(tert-butoxycarbonyl)(methyl)amino]-1-hydroxyethyl}phenyl 3-toluene-sulfonate (example 257) starting from 3-toluenesulfonyl chloride, 4-{2-[(tert-butoxycarbonyl)(methyl)amino]-1-hydroxyethyl}phenyl 4-isopropyl-benzenesulfonate (example 258) starting from 4-isopropyl-benzenesulfonyl chloride, 4-{2-[(tert-butoxycarbonyl)(methyl)amino]-1-hydroxyethyl}phenyl 4-(2-oxo-1-pyrrolidinyl)-benzenesulfonate (example 259) starting from 4-(2-oxo-1-pyrrolidinyl)-benzenesulfonyl chloride, 4-{2-[(tert-butoxycarbonyl)(methyl)amino]-1-hydroxyethyl}phenyl 4-(2-methoxyphenoxy)-benzenesulfonate (example 260) starting from 4-(2-methoxyphenoxy)-benzenesulfonyl chloride, 4-{2-[(tert-butoxycarbonyl)(methyl)amino]-1-hydroxyethyl}phenyl 4-(2-chloro-phenoxy)-benzenesulfonate (example 261) starting from 4-(2-chloro-phenoxy)-benzenesulfonyl chloride, 4-{2-[(tert-butoxycarbonyl)(methyl)amino]-1-hydroxyethyl}phenyl 4-(2-methylphenoxy)benzenesulfonate (example 262) starting from 4-(2-methylphenoxy)benzenesulfonyl chloride, 4-{2-[(tert-butoxycarbonyl)(methyl)amino]-1-hydroxyethyl}phenyl 4'-chloro (1,1'-biphenyl)-4-sulfonate (example 263) starting from 4'-chloro(1,1'-biphenyl)-4-sulfonyl chloride, 4-{2-[(tert-butoxycarbonyl)(methyl)amino]-1-hydroxyethyl}phenyl 4'-fluoro(1,1'-biphenyl)-4-sulfonate (example 264) starting from 4'-fluoro(1,1'-biphenyl)-4-sulfonyl chloride, 4-{2-[(tert-butoxycarbonyl)(methyl)amino]-1-hydroxyethyl}phenyl 4'-methoxy-(1,1'-biphenyl)-4-sulfonate (example 265) starting from 4'-methoxy-(1,1'-biphenyl)-4-sulfonyl chloride, 4-{2-[(tert-butoxycarbonyl)(methyl)amino]-1-hydroxyethyl}phenyl 3',4'-dichloro-(1,1'-biphenyl)-4-sulfonate (example 266) starting from 3',4'-dichloro-(1,1'-biphenyl)-4-sulfonyl chloride, 4-{2-[(tert-butoxycarbonyl)(methyl)amino]-1-hydroxyethyl}phenyl 4-phenoxy-benzenesulfonate (example 267) starting from 4-phenoxybenzenesulfonyl chloride, 4-{2-[(tert-butoxycarbonyl)(methyl)amino]-1-hydroxyethyl}phenyl 4'-methyl-(1,1'-biphenyl)-4-sulfon (example 268) starting from 4'-methyl-(1,1'-biphenyl)-4-sulfonyl chloride, 4-{2-[(tert-butoxycarbonyl)(methyl)amino]-1-hydroxyethyl}phenyl 5-bromo-2,3-dihydrobenzo[b]furan-7-sulfonate (example 269) starting from 5-bromo-2,3-dihydrobenzo[b]furan-7-sulfonyl chloride, 4-{2-[(tert-butoxycarbonyl)(methyl)amino]-1-hydroxyethyl}phenyl 3,4,5-trifluoro-benzenesulfonate (example 270) starting from 3,4,5-trifluoro-benzenesulfonyl chloride, 4-{2-[(tert-butoxycarbonyl)(methyl)amino]-1-hydroxyethyl}phenyl 3-(5-methyl-1,2,4-oxadiazol-3-yl)-benzenesulfonate (example 271) starting from 3-(5-methyl-1,2,4-oxadiazol-3-yl)-benzenesulfonyl chloride, 4-{2-[(tert-butoxycarbonyl)(methyl)amino]-1-hydroxyethyl}phenyl 4-(2-methyl-1,3-thiazol-4-yl)-benzenesulfonate (example 272) starting from 4-(2-methyl-1,3-thiazol-4-yl)-benzenesulfonyl chloride, 4-{2-[(tert-butoxycarbonyl)(methyl)amino]-1-hydroxyethyl}phenyl 1-acetyl-5-indolinesulfonate (example 273) starting from 1-acetyl-5-indolinesulfonyl chloride, 4-{2-[(tert-butoxycarbonyl)(methyl)amino]-1-hydroxyethyl}phenyl 3-(2-methyl-1,3-thiazol-4-yl)-benzenesulfonate (example 274) starting from 3-(2-methyl-1,3-thiazol-4-yl)-benzenesulfonyl chloride, and 4-{2-[(tert-butoxycarbonyl)(methyl)amino]-hydroxyethyl}phenyl 1,3-benzo-dioxole-5-sulfonate (example 275) starting from 1,3-benzodioxole-5-sulfonyl chloride.

Examples 276 AND 277

Synthesis of 1-[4-(benzoyloxy)phenyl]-2-[(tert-butoxycarbonyl)-methylamino]ethyl-1H-imidazole-1-thiocarboxylate and 1-[4-(benzoyloxy)phenyl]-2-[(tert-butoxycarbonyl)-methylamino]ethyl-1H-triazole-1-carboxylate The procedure of example 8 is repeated, except that 1,1'-carbonyldiimidazole is replaced with 1,1'-thiocarbonyldiimidazole or 1,1'-carbonylditriazole. In this way are obtained with similar yields:

1-[4-(benzoyloxy)phenyl]-2-[(tert-butoxycarbonyl)-methylamino]ethyl-1H-imidazole-1-thiocarboxylate (example 276), and 1-[4-(benzoyloxy)phenyl]-2-[(tert-butoxycarbonyl)-methylamino]ethyl-1H-triazole-1-carboxylate (example 277).

Examples 278 TO 350

Synthesis of 1-[4-(benzoyloxy)phenyl]-2-[(tert-butoxycarbonyl)-methylamino]ethyl-1H-imidazole-1-carboxylate analogues The procedure of example 8 is repeated, except that the derivative of example 4 is replaced with a 4-{2-[(tert-butoxycarbonyl)(methyl)amino]-1-hydroxyethyl}phenyl substituted benzoate from examples 15 to 90. The following 1-[4-(benzoyloxy)phenyl]-2-[(tert-butoxycarbonyl)-methylamino]ethyl-1H-imidazole-1-carboxylate analogues are obtained in similar yields:

1-[4-(4-methoxybenzoyloxy)phenyl]-2-[(tert-butoxycarbonyl)-methylamino]ethyl-1H-imidazole-1-carboxylate (example 278) from the substituted benzoate of example 15, 1-[4-(2-bromobenzoyloxy)phenyl]-2-[(tert-butoxycarbonyl)-methylamino]ethyl-1H-imidazole-1-carboxylate (example 279) from the substituted benzoate of example 16, 1-[4-(4-bromobenzoyloxy)phenyl]-2-[(tert-butoxycarbonyl)-methylamino]ethyl-1H-imidazole-1-carboxylate (example 280) from the substituted benzoate of example 17, 1-[4-(3-chlorobenzoyloxy)phenyl]-2-[(tert-butoxycarbonyl)-methylamino]ethyl-1H-imidazole-1-carboxylate (example 281) from the substituted benzoate of example 18, 1-[4-(pentafluorobenzoyloxy)phenyl]-2-[(tert-butoxycarbonyl)-methylamino]ethyl-1H-imidazole-1-carboxylate (example 282) from the substituted benzoate of example 19, 1-[4-(2-chlorobenzoyloxy)phenyl]-2-[(tert-butoxycarbonyl)-methylamino]ethyl-1H-imidazole-1-carboxylate (example 283) from the substituted benzoate of example 20, 1-[4-(p-toluoyloxy)phenyl]-2-[(tert-butoxycarbonyl)-methylamino]ethyl-1H-imidazole-1-carboxylate (example 284) from the substituted benzoate of example 21, 1-[4-(4-chlorobenzoyloxy)phenyl]-2-[(tert-butoxycarbonyl)-methylamino]ethyl-1H-imidazole-1-carboxylate (example 285) from the substituted benzoate of example 22, 1-[4-(2,4-dichlorobenzoyloxy)phenyl]-2-[(tert-butoxycarbonyl)-methylamino]ethyl-1H-imidazole-1-carboxylate (example 286) from the substituted benzoate of example 23, 1-[4-(3,4-dichlorobenzoyloxy)phenyl]-2-[(tert-butoxycarbonyl)-methylamino]ethyl-1H-imidazole-1-carboxylate (example 287) from the substituted benzoate of example 24, 1-[4-(4-nitrobenzoyloxy)phenyl]-2-[(tert-butoxycarbonyl)-methylamino]ethyl-1H-imidazole-1-carboxylate (example 288) from the substituted benzoate of example 25, 1-[4-(4-fluorobenzoyloxy)phenyl]-2-[(tert-butoxycarbonyl)-methylamino]ethyl-1H-imidazole-1-carboxylate (example 289) from the substituted benzoate of example 26, 1-[4-(2-fluorobenzoyloxy)phenyl]-2-[(tert-butoxycarbonyl)-methylamino]ethyl-1H-imidazole-1-carboxylate (example 290) from the substituted benzoate of example 27, 1-[4-(o-toluoyloxy)phenyl]-2-[(tert-butoxycarbonyl)-methylamino]ethyl-1H-imidazole-1-carboxylate (example 291) from the substituted benzoate of example 28, 1-[4-(m-toluoyloxy)phenyl]-2-[(tert-butoxycarbonyl)-methylamino]ethyl-1H-imidazole-1-carboxylate (example 292) from the substituted benzoate of example 29, 1-[4-(4-cyanobenzoyloxy)phenyl]-2-[(tert-butoxycarbonyl)-methylamino]ethyl-1H-imidazole-1-carboxylate (example 293) from the substituted benzoate of example 30, 1-[4-(3-nitrobenzoyloxy)phenyl]-2-[(tert-butoxycarbonyl)-methylamino]ethyl-1H-imidazole-1-carboxylate (example 294) from the substituted benzoate of example 31, 1-[4-(4-tert-butylbenzoyloxy)phenyl]-2-[(tert-butoxycarbonyl)-methylamino]ethyl-1H-imidazole-1-carboxylate (example 295) from the substituted benzoate of example 32, 1-[4-(4-phenyl benzoyloxy)phenyl]-2-[(tert-butoxycarbonyl)-methylamino]ethyl-1H-imidazole-1-carboxylate (example 296) from the substituted benzoate of example 33, 1-[4-(3,5-dimethoxybenzoyloxy)phenyl]-2-[(tert-butoxycarbonyl)-methylamino]ethyl-1H-imidazole-1-carboxylate (example 297) from the substituted benzoate of example 34, 1-[4-(3-fluorobenzoyloxy)phenyl]-2-[(tert-butoxycarbonyl)-methylamino]ethyl-1H-imidazole-1-carboxylate (example 298) from the substituted benzoate of example 35, 1-[4-(2,6-dichlorobenzoyloxy)phenyl]-2-[(tert-butoxycarbonyl)-methylamino]ethyl-1H-imidazole-1-carboxylate (example 299) from the substituted benzoate of example 36, 1-[4-(4-butyl benzoyloxy)phenyl]-2-[(tert-butoxycarbonyl)-methylamino]ethyl-1H-imidazole-1-carboxylate (example 300) from the substituted benzoate of example 37, 1-[4-(4-heptoxybenzoyloxy)phenyl]-2-[(tert-butoxycarbonyl)-methylamino]ethyl-1H-imidazole-1-carboxylate (example 301) from the substituted benzoate of example 38, 1-[4-(4-hexylbenzoyloxy)phenyl]-2-[(tert-butoxycarbonyl)-methylamino]ethyl-1H-imidazole-1-carboxylate (example 302) from the substituted benzoate of example 39, 1-[4-(4-hexyloxybenzoyloxy)phenyl]-2-[(tert-butoxycarbonyl)-methyl amino]ethyl-1H-imidazole-1-carboxylate (example 303) from the substituted benzoate of example 40, 1-[4-(4-pentylbenzoyloxy)phenyl]-2-[(tert-butoxycarbonyl)-methylamino]ethyl-1H-imidazole-1-carboxylate (example 304) from the substituted benzoate of example 41, 1-[4-(m-anisoyloxy)phenyl]-2-[(tert-butoxycarbonyl)-methylamino]ethyl-1H-imidazole-1-carboxylate (example 305) from the substituted benzoate of example 42, 1-[4-(2,6-difluorobenzoyloxy)phenyl]-2-[(tert-butoxycarbonyl)-methylamino]ethyl-1H-imidazole-1-carboxylate (example 306) from the substituted benzoate of example 43, 1-[4-(2-nitrobenzoyloxy)phenyl]-2-[(tert-butoxycarbonyl)-methylamino]ethyl-1H-imidazole-1-carboxylate (example 307) from the substituted benzoate of example 44, 1-[4-(4-chloro-3-nitrobenzoyloxy)phenyl]-2-[(tert-butoxycarbonyl)-methylamino]ethyl-1H-imidazole-1-carboxylate (example 308) from the substituted benzoate of example 45, 1-[4-(3,4-difluorobenzoyloxy)phenyl]-2-[tert-butoxycarbonyl)-methylamino]ethyl-1H-imidazole-1-carboxylate (example 309) from the substituted benzoate of example 46, 1-[4-(2-iodobenzoyloxy)phenyl]-2-[(tert-butoxycarbonyl)-methylamino]ethyl-1H-imidazole-1-carboxylate (example 310) from the substituted benzoate of example 47, 1-[4-(o-anisoyloxy)phenyl]-2-[(tert-butoxycarbonyl)-methylamino]ethyl-1H-imidazole-1-carboxylate (example 311) from the substituted benzoate of example 48, 1-[4-(2,4-difluorobenzoyloxy)phenyl]-2-[(tert-butoxycarbonyl)-methylamino]ethyl-1H-imidazole-1-carboxylate (example 312) from the substituted benzoate of example 49, 1-[4-(4-(trifluoromethyl)-benzoyloxy)phenyl]-2-[(tert-butoxycarbonyl)-methylamino]ethyl-1H-imidazole-1-carboxylate (example 313) from the substituted benzoate of example 50, 1-[4-(3-(chloromethyl)-benzoyloxy)phenyl]-2-[(tert-butoxycarbonyl)-methylamino]ethyl-1H-imidazole-1-carboxylate (example 314) from the substituted benzoate of example 51, 1-[4-(4-(chloromethyl)-benzoyloxy)phenyl]-2-[(tert-butoxycarbonyl)-methylamino]ethyl-1H-imidazole-1-carboxylate (example 315) from the substituted benzoate of example 52, 1-[4-(3-(dichloromethyl)-benzoyloxy)phenyl]-2-[(tert-butoxycarbonyl)-methylamino]ethyl-1H-imidazole-1-carboxylate (example 316) from the substituted benzoate of example 53, 1-[4-(2,3,4,5-tetrafluorobenzoyloxy)phenyl]-2-[(tert-butoxycarbonyl)-methylamino]ethyl-1H-imidazole-1-carboxylate (example 317) from the substituted benzoate of example 54, 1-[4-(2,4,6-trichlorobenzoyloxy)phenyl]-2-[(tert-butoxycarbonyl)-methylamino]ethyl-1H-imidazole-1-carboxylate (example 318) from the substituted benzoate of example 55, 1-[4-(2,3,4-trifluorobenzoyloxy)phenyl]-2-[(tert-butoxycarbonyl)-methylamino]ethyl-1H-imidazole-1-carboxylate (example 319) from the substituted benzoate of example 56, 1-[4-(2,4,6-trifluorobenzoyloxy)phenyl]-2-[(tert-butoxycarbonyl)-methylamino]ethyl-1H-imidazole-1-carboxylate (example 320) from the substituted benzoate of example 57, 1-[4-(4-bromo-2-fluorobenzoyloxy)phenyl]-2-[(tert-butoxycarbonyl)-methylamino]ethyl-1H-imidazole-1-carboxylate (example 321) from the substituted benzoate of example 58, 1-[4-(2,3,5,6-tetrafluorobenzoyloxy)phenyl]-2-[(tert-butoxycarbonyl)-methylamino]ethyl-1H-imidazole-1-carboxylate (example 322) from the substituted benzoate of example 59, 1-[4-(3,5-dinitrobenzoyloxy)phenyl]-2-[(tert-butoxycarbonyl)-methylamino]ethyl-1H-imidazole-1-carboxylate (example 323) from the substituted benzoate of example 60, 1-[4-(4-heptylbenzoyloxy)phenyl]-2-[(tert-butoxycarbonyl)-methylamino]ethyl-1H-imidazole-1-carboxylate (example 324) from the substituted benzoate of example 61, 1-[4-(4-iodobenzoyloxy)phenyl]-2-[(tert-butoxycarbonyl)-methylamino]ethyl-1H-imidazole-1-carboxylate (example 325) from the substituted benzoate of example 62, 1-[4-(4-octylbenzoyloxy)phenyl]-2-[(tert-butoxycarbonyl)-methylamino]ethyl-1H-imidazole-1-carboxylate (example 326) from the substituted benzoate of example 63, 1-[4-(4-pentoxybenzoyloxy)phenyl]-2-[(tert-butoxycarbonyl)-methylamino]ethyl-1H-imidazole-1-carboxylate (example 327) from the substituted benzoate of example 64, 1-[4-(4-phenylazobenzoyloxy)phenyl]-2-[(tert-butoxycarbonyl)-methylamino]ethyl-1H-imidazole-1-carboxylate (example 328) from the substituted benzoate of example 65, 1-[4-(4-propylbenzoyloxy)phenyl]-2-[(tert-butoxycarbonyl)-methylamino]ethyl-1H-imidazole-1-carboxylate (example 329) from the substituted benzoate of example 66, 1-[4-(3,5-dichlorobenzoyloxy)phenyl]-2-[(tert-butoxycarbonyl)-methylamino]ethyl-1H-imidazole-1-carboxylate (example 330) from the substituted benzoate of example 67, 1-[4-(3-fluoro-4-(trifluoromethyl)-benzoyloxy)phenyl]-2-[(tert-butoxycarbonyl)-methylamino]ethyl-1H-imidazole-1-carboxylate (example 331) from the substituted benzoate of example 68, 1-[4-(2,6-dimethoxybenzoyloxy)phenyl]-2-[(tert-butoxycarbonyl)-methylamino]ethyl-1H-imidazole-1-carboxylate (example 332) from the substituted benzoate of example 69, 1-[4-(2,4-dimethoxybenzoyloxy)phenyl]-2-[(tert-butoxycarbonyl)-methylamino]ethyl-1H-imidazole-1-carboxylate (example 333) from the substituted benzoate of example 71, 1-[4-(4-(thien-2-yl)-benzoyloxy)phenyl]-2-[(tert-butoxycarbonyl)-methylamino]ethyl-1H-imidazole-1-carboxylate (example 334) from the substituted benzoate of example 72, 1-[4-(4-(1,2,3-thiadiazol-4-yl)-benzoyloxy)phenyl]-2-[(tert-butoxycarbonyl)-methylamino]ethyl-1H-imidazole-1-carboxylate (example 335) from the substituted benzoate of example 73, 1-[4-(4-(1H-pyrazol-1-yl)-benzoyloxy)phenyl]-2-[(tert-butoxycarbonyl)-methylamino]ethyl-1H-imidazole-1-carboxylate (example 336) from the substituted benzoate of example 74, 1-[4-(5-bromo-2,3,4-trimethylbenzoyloxy)phenyl]-2-[(tert-butoxycarbonyl)-methylamino]ethyl-1H-imidazole-1-carboxylate (example 337) from the substituted benzoate of example 76, 1-[4-(2-chloro-4-fluorobenzoyloxy)phenyl]-2-[(tert-butoxycarbonyl)-methylamino]ethyl-1H-imidazole-1-carboxylate (example 338) from the substituted benzoate of example 77, 1-[4-(2,3-difluorobenzoyloxy)phenyl]-2-[(tert-butoxycarbonyl)-methylamino]ethyl-1H-imidazole-1-carboxylate (example 339) from the substituted benzoate of example 79, 1-[4-(2-fluoro-5-(trifluoromethyl)-benzoyloxy)phenyl]-2-[(tert-butoxycarbonyl)-methylamino]ethyl-1H-imidazole-1-carboxylate (example 340) from the substituted benzoate of example 80, 1-[4-(2,3,6-trifluorobenzoyloxy)phenyl]-2-[(tert-butoxycarbonyl)-methylamino]ethyl-1H-imidazole-1-carboxylate (example 341) from the substituted benzoate of example 81, 1-[4-(3-fluoro-4-methylbenzoyloxy)phenyl]-2-[(tert-butoxycarbonyl)-methylamino]ethyl-1H-imidazole-1-carboxylate (example 342) from the substituted benzoate of example 82, 1-[4-(3-cyclopentoxy-4-methoxybenzoyloxy)phenyl]-2-[(tert-butoxycarbonyl)-methylamino]ethyl-1H-imidazole-1-carboxylate (example 343) from the substituted benzoate of example 83, 1-[4-(4-fluoro-3-(trifluoromethyl)-benzoyloxy)phenyl]-2-[(tert-butoxycarbonyl)-methylamino]ethyl-1H-imidazole-1-carboxylate (example 344) from the substituted benzoate of example 84, 1-[4-(3-(2-methylthiazol-4-yl)-benzoyloxy)phenyl]-2-[(tert-butoxycarbonyl)-methylamino]ethyl-1H-imidazole-1-carboxylate (example 345) from the substituted benzoate of example 85, 1-[4-(2,4,6-trimethylbenzoyloxy)phenyl]-2-[(tert-butoxycarbonyl)-methylamino]ethyl-1H-imidazole-1-carboxylate (example 346) from the substituted benzoate of example 86, 1-[4-(2-(thien-2-yl)-benzoyloxy)phenyl]-2-[(tert-butoxycarbonyl)-methylamino]ethyl-1H-imidazole-1-carboxylate (example 347) from the substituted benzoate of example 87, 1-[4-(3-cyanobenzoyloxy)phenyl]-2-[(tert-butoxycarbonyl)-methylamino]ethyl-1H-imidazole-1-carboxylate (example 348) from the substituted benzoate of example 88, 1-[4-(3-(5-methyl-1,2,4-oxadiazol-3-yl)-benzoyloxy)phenyl]-2-[(tert-butoxycarbonyl)-methylamino]ethyl-1H-imidazole-1-carboxylate (example 349) from the substituted benzoate of example 89, and 1-[4-(4-(5-methyl-1,2,4-oxadiazol-3-yl)-benzoyloxy)phenyl]-2-[(tert-butoxycarbonyl)-methylamino]ethyl-1H-imidazole-1-carboxylate (example 350) from the substituted benzoate of example 90.

Example 351

MTT Test: The Effect of the Synephrine Derivatives of Cell Viability

The MTT test is a standard assay addressing cell toxicity of a compound. It is based on the principle that after 3-4 hours of cell incubation with MTT (3-(4,5-dimethylthiazole-2-yl)-2,5-diphenyl tetrazolium bromide) so-called purple formazan crystals develop in living and early apoptotic cells. Dead cells don't produce formazan crystals.

Different cell lines were tested. Unless indicated differently, A549 human lung epithelial cells (derived from lung carcinoma) and L929sA murine fibroblast cells were cultured in DMEM with 10% FCS, 100 U/ml penicillin and 100 μg/ml streptomycin. Unless indicated differently, the human multiple myeloma cell lines L363, U266 and MM1.S were cultured in RPMI 1640 with Glutamax-I, supplemented with 10% FCS, 100 U/ml penicillin and 100 μg/ml streptomycin. Cells were seeded at 5000 cells/well (for adherent A549 and L929sA cells) or at 10000 cells/well (for the multiple myeloma lines in suspension) in 96 well plates. Cells were incubated in the presence of the respective synephrine compounds or vehicle (EtOH; for control test) in a final volume of 0.2 ml for 24 or 48 hours at 37° C. Subsequently, 20 μl of MTT solution (5 mg/ml in phosphate-buffered saline) was added to each well. After 4 hours incubation at 37° C., 80 μl of the extraction buffer (10% SDS, 0.01 M HCl) was added. After overnight incubation at room temperature, the optical densities at 590 nm were measured. Results are illustrated in FIGS. 2 to 6 and are expressed as percentage of viable cells as compared to vehicle-treated controls.

Figure 2A:
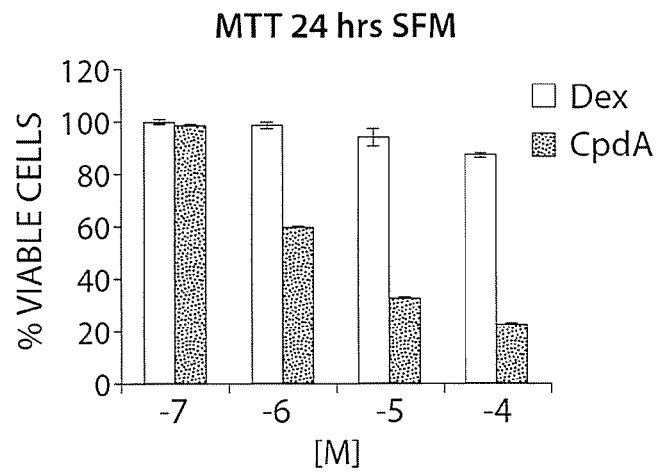
FIGS. 2A and 2B show the viability of multiple myeloma cells U266 after treatment with 2-(4-acetoxyphenyl)-2-chloro-N-methyl-ethylammonium chloride (CpdA) or dexamethasone using the so-called MTT test.
Figure 2B:
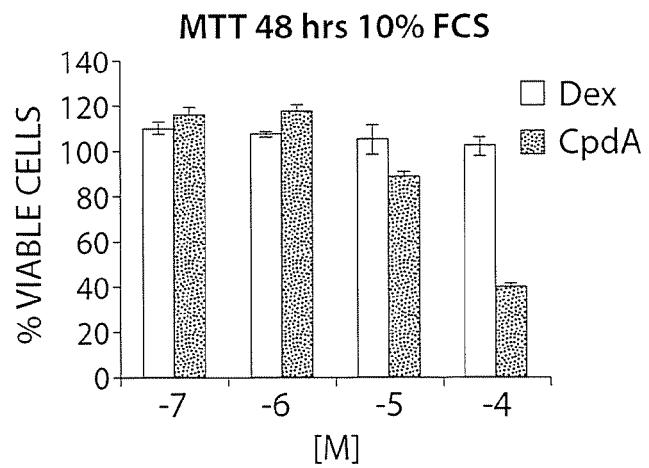

The inhibition of the viability of multiple myeloma cells U266 by CpdA in a dose-responsive manner is illustrated by FIG. 2 for both Serum Free Medium (SFM, FIG. 2A) and in growth medium containing 10% Fetal Calf Serum (FCS, FIG. 2B). The activity of Dexamethasone (DEX) was also measured for comparison. FIG. 2A illustrates that at $10^{-6}$ M CpdA is able to inhibit viability of U266 cells for 40%, when cultured in serum-free growth medium within 24 hours. FIG. 2A also shows that at $10^{-5}$ M CpdA is able to mediate 60% cell killing in serum-free growth medium within 24 hours, whereas, as illustrated by FIG. 2B, the same concentration elicits 10% of cell killing in normal growth medium containing 10% fetal calf serum within 48 hours. Treatment of the cells with $10^{-4}$ M of CpdA in serum-free or serum-containing medium, led to 80% and 60% of cell killing, respectively (FIGS. 2A and 2B). Upon comparison to DEX as a reference compound, a substantial difference was observed: it was found that DEX only slightly affected cell viability at $10^{-4}$ M (10% reduction) even when cells were cultured in serum-free medium.

Figure 3A:
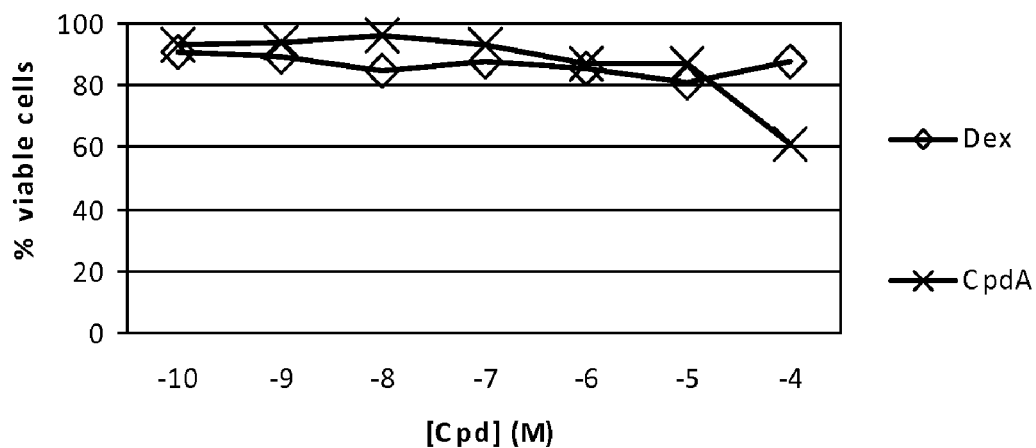
FIGS. 3A and B show the activity on inhibiting cell viability of synephrine derivatives according to certain embodiments of the invention compared to the activity of dexamethasone. The top panels (3Aa and 3Ba) show the effect of Compound A (CpdA) versus the control Dexamethasone (Dex). The bottom panels (3Ab and 3Bb) show the effect of the compounds Napht, Benz and Isobut versus the control Dexamethasone (Dex).
Figure 3A:
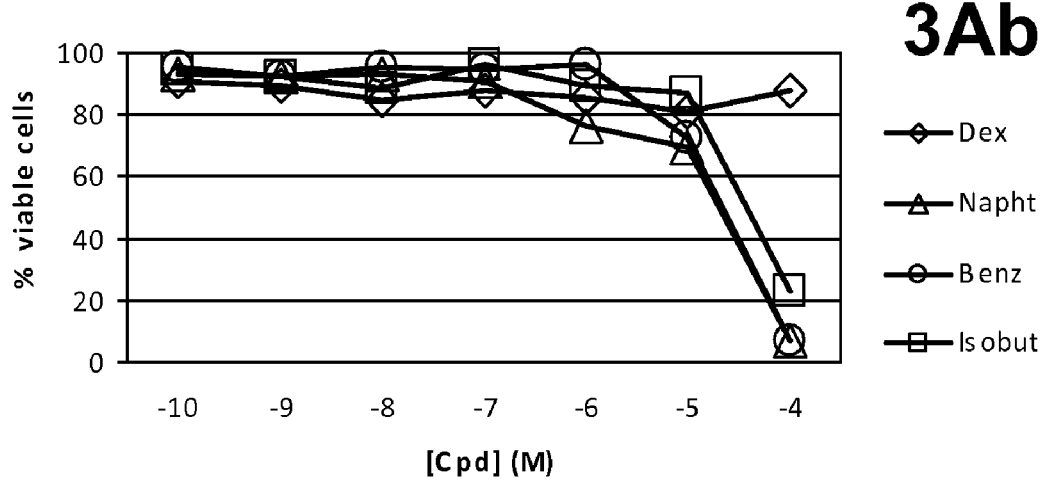
Figure 3:
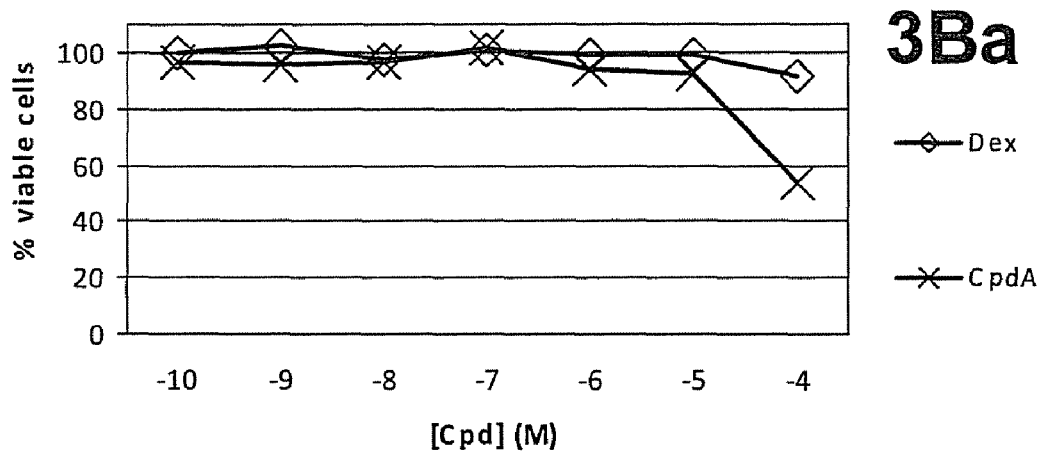
Figure 3:
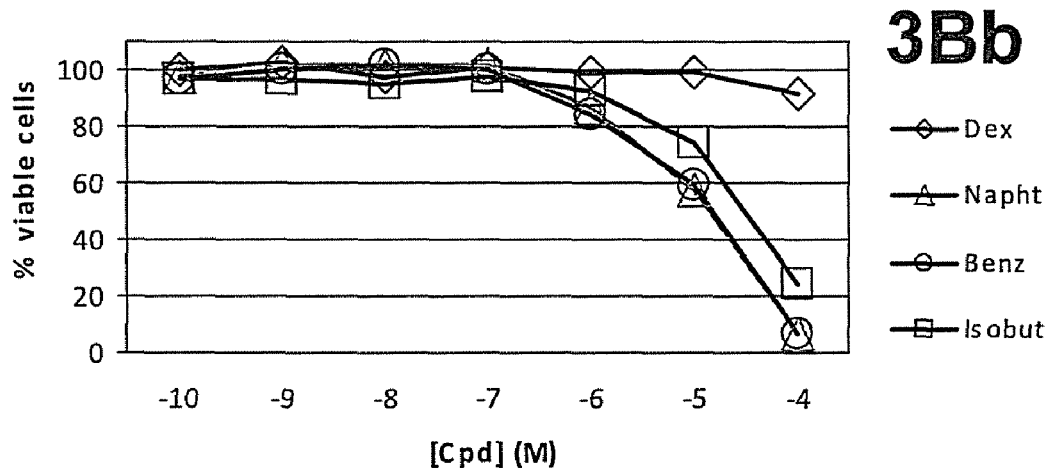
Figure 4A:
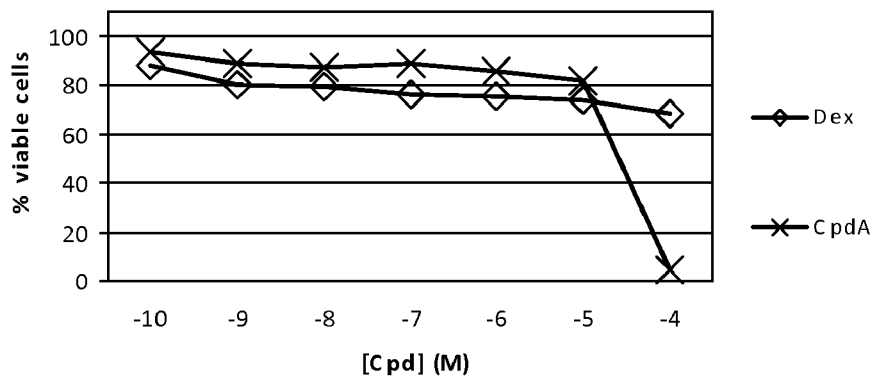
FIG. 4A shows the activity on inhibiting cell viability of synephrine derivatives according to certain embodiments of the invention compared to the activity of dexamethasone. The top panel (4Aa) shows the effect of Compound A (CpdA) versus the control Dexamethasone (Dex). The bottom panel (4Ab) shows the effect of the compounds Napht, Benz and Isobut versus the control Dexamethasone (Dex).
Figure 4A:
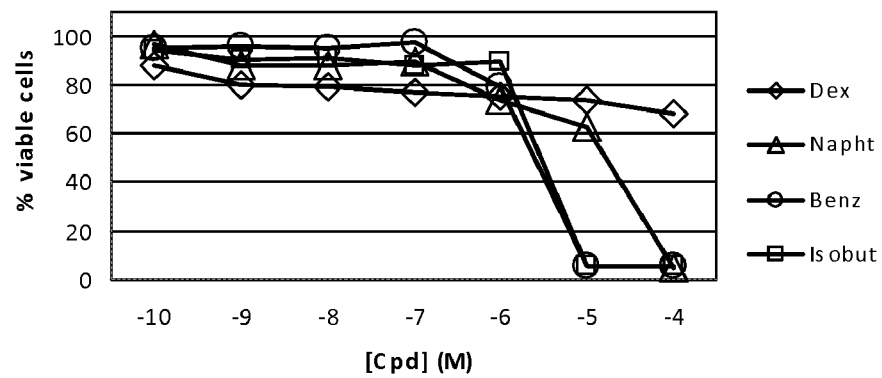

The MTT test was further extended to include alternative synephrine derivatives and a range of multiple myeloma cell lines for which the results are illustrated by FIGS. 3A, 3B and 4A. Human multiple myeloma cell lines L363, U266 and MM1.S were cultured in RPMI 1640 with Glutamax-I, supplemented with 10% FCS, 100 U/ml penicillin and 100 μg/ml streptomycin. Cells were seeded at 10000 cells/well in 96 well plates. Cells were incubated in the presence of test compounds or vehicle in a final volume of 0.2 ml for 24 or 48 hours at 37° C. The test compounds included in the test were the synephrine derivatives CpdA, Naphth, Benz and Isobut, and DEX as a comparative example. Subsequently, 20 μl of MTT solution (5 mg/ml in phosphate-buffered saline) was added to each well. After 4 hours incubation at 37° C., 80 μl of the extraction buffer (10% SDS, 0.01 M HCl) was added. After 48 hours incubation at room temperature, the optical densities at 590 nm were measured. Results are expressed as percentage of viable cells as compared to vehicle-treated controls.

FIG. 3A shows that $10^{-6}$ to $10^{-5}$ M CpdA affect cell viability for about 15-20%. A ten times higher concentration of CpdA ($10^{-4}$ M) is able to block U266 cell viability for 40%. For $10^{-4}$ M of Benz, Isobut and Naphth, a percentage of cell killing was observed of 90%, 80% and 70%, respectively. The results obtained for the synephrine derivatives were substantially different compared to the reference compound DEX, which did not affect cell viability of U266 cells in serum-containing growth medium, at the concentrations tested.

FIG. 3B illustrates the results obtained with the L363 cell line, which was tested under the same conditions. It was observed that CpdA at $10^{-4}$ M blocks cell viability for 50%, and Benz, Isobut and Naphth demonstrated to block cell viability to a great extent, 90%, 80% and 90%, respectively. Moreover, the L363 cell line was more susceptible to the synephrine derivative-mediated inhibition of cell viability compared to the U266 cell line, as $10^{-5}$ M of both Benz and Naphth resulted in a 40% cell killing. Similarly, $10^{-5}$ M Isobut resulted in 25% of cell killing.

The MM1.S cell line, which has been described to be more sensitive to DEX-mediated cell killing, was also tested under the same conditions and results are illustrated in FIG. 4A. DEX, the reference compound, was now able to inhibit cell viability for 30% at $10^{-4}$ M. Naphth at $10^{-5}$ M inhibited for about 35% whereas Naphth at $10^{-4}$ M efficiently blocked cell viability almost completely. The greater sensitivity of this cell line was also reflected in a bigger effect of Benz and Isobut at lower doses. Indeed, $10^{-5}$ M of both compounds was able to block cell viability completely. The latter result is an important finding with regard to possible therapeutic applicability.

Figure 4B:
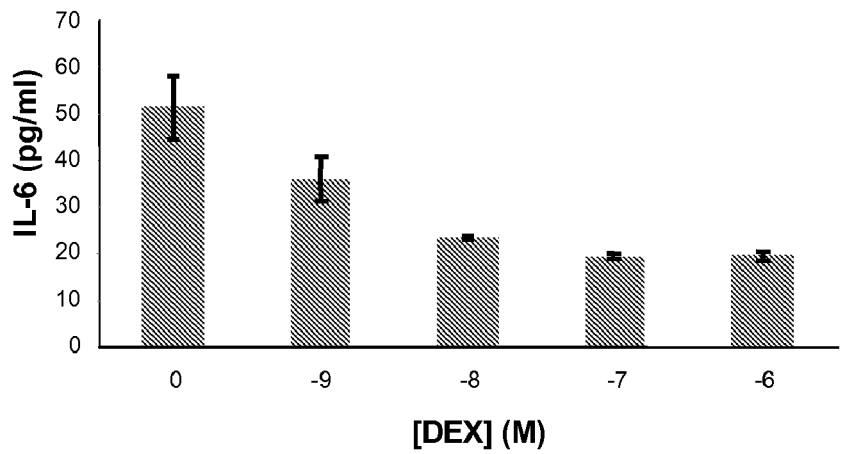
FIG. 4B shows a control test of the dexamethasone-induced inhibition of autocrine IL-6 secretion in U266 cells.

As a control, FIG. 4B illustrates the activity of DEX on the inhibition of autocrine IL-6 secretion in U266 cells. Even at a dose of $10^{-9}$ M, DEX significantly inhibited IL-6 expression thereby illustrating that, although DEX is not substantially affecting cell viability, the cell line is still sensitive to DEX as an anti-inflammatory agent.

Figure 5A:
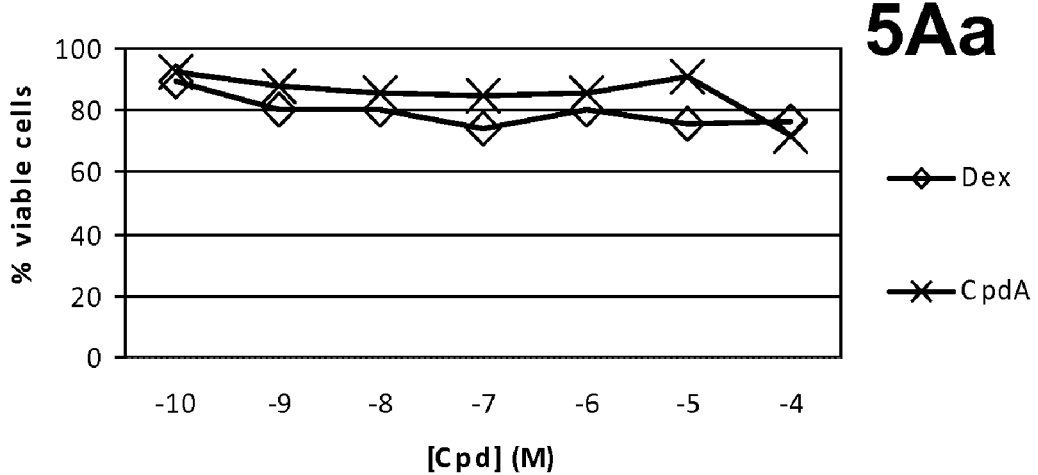
FIGS. 5 and 6 show the activity of synephrine derivatives according to certain embodiments of the invention on the cell viability of non-immune cells. The top panels (5Aa, 5Ba, 6Aa and 6Ba) show the effect of Compound A (CpdA) versus the control Dexamethasone (Dex). The bottom panels (5Ab, 5Bb, 6Ab and 6Bb) show the effect of the compounds Napht, Benz and Isobut versus the control Dexamethasone (Dex).
Figure 5A:
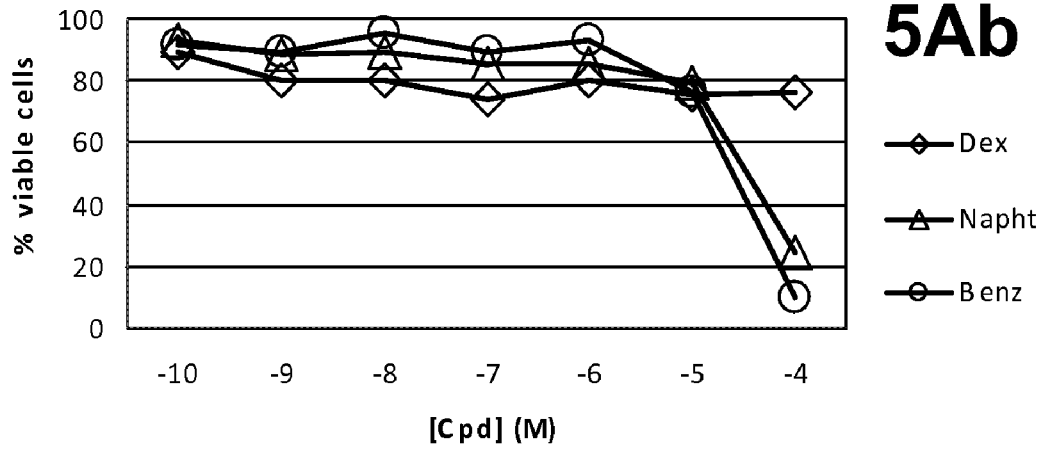
Figure 5B:
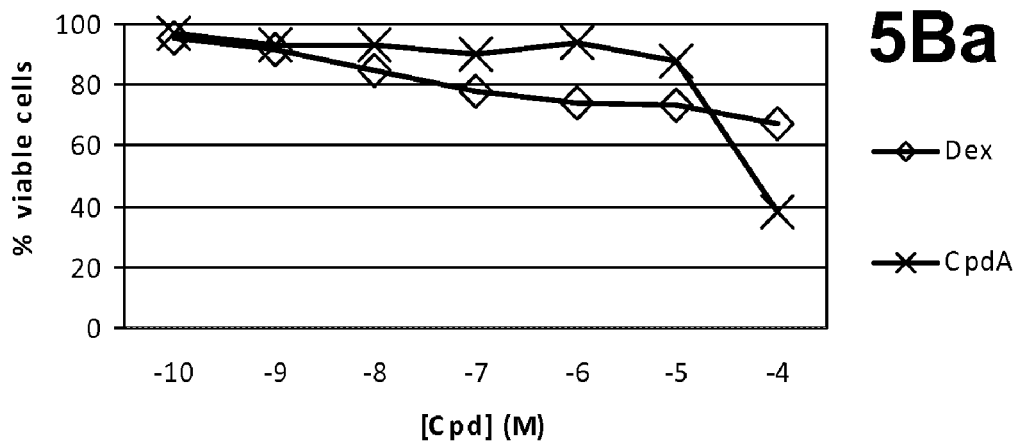
Figure 5B:
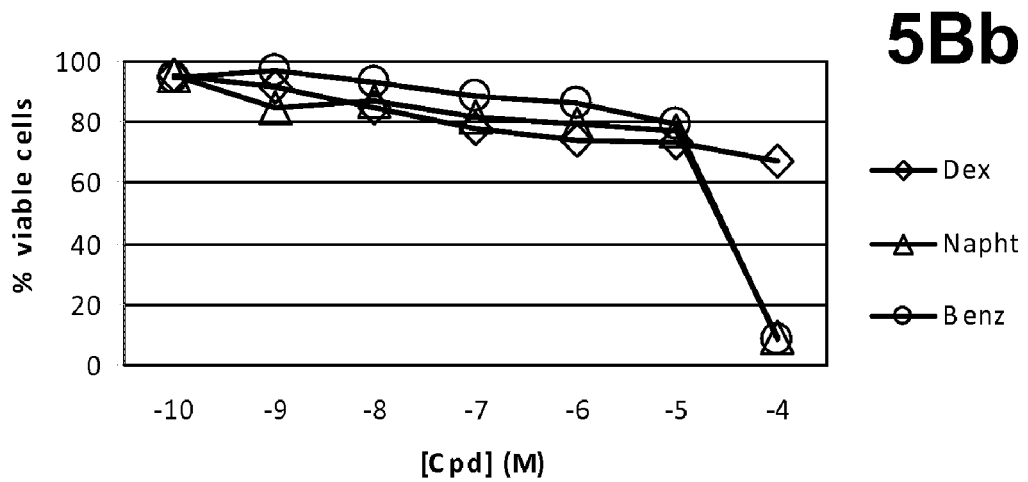

In a further MTT test, the activity of the synephrine derivatives on the inhibition of cell viability of non-immune cells was measured. In order to determine to what extent the observed effects on the multiple myeloma cells displayed some degree of specificity, we tested the effect of the synephrine compounds on cell viability of L929sA fibroblasts and A549 human lung epithelial cells (derived from human lung carcinoma). Tests were performed for 24 hours and for 48 hours. The results are illustrated by FIGS. 5A and 5B for L929 cells, and by FIGS. 6A and 6B for A549 cells. It was observed that CpdA at $10^{-5}$ M blocked cell viability of L929sA and A549 for not more than 10%.

For L929sA cells, at $10^{-5}$ M Benz and Naphth blocked cell viability for not more than 20% within 48 hours (FIG. 5B). For A549 cells, Benz at $10^{-5}$ M is not able to block cell viability at 24 hours (FIG. 6A) and blocks 10% at 48 hours (FIG. 6B), whereas Naphth at $10^{-5}$ M blocks cell viability for about 10% at 24 hours (FIG. 8A) and up to 20% at 48 hours (FIG. 6B).

Figure 6A:
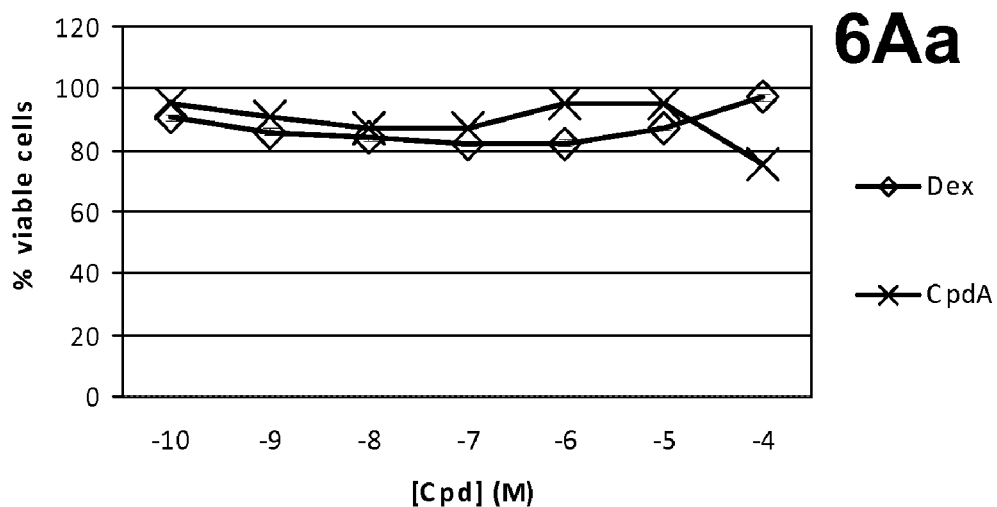
Figure 6A:
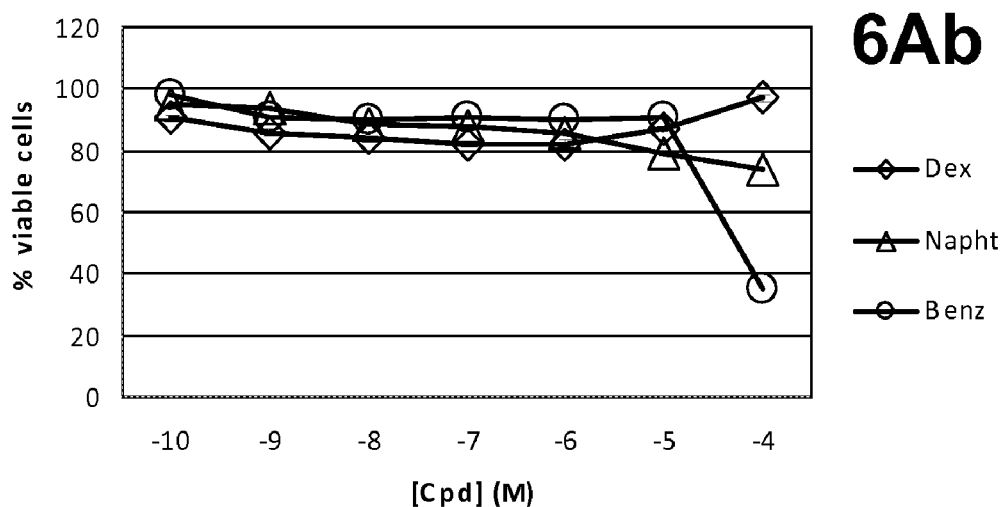
Figure 6B:
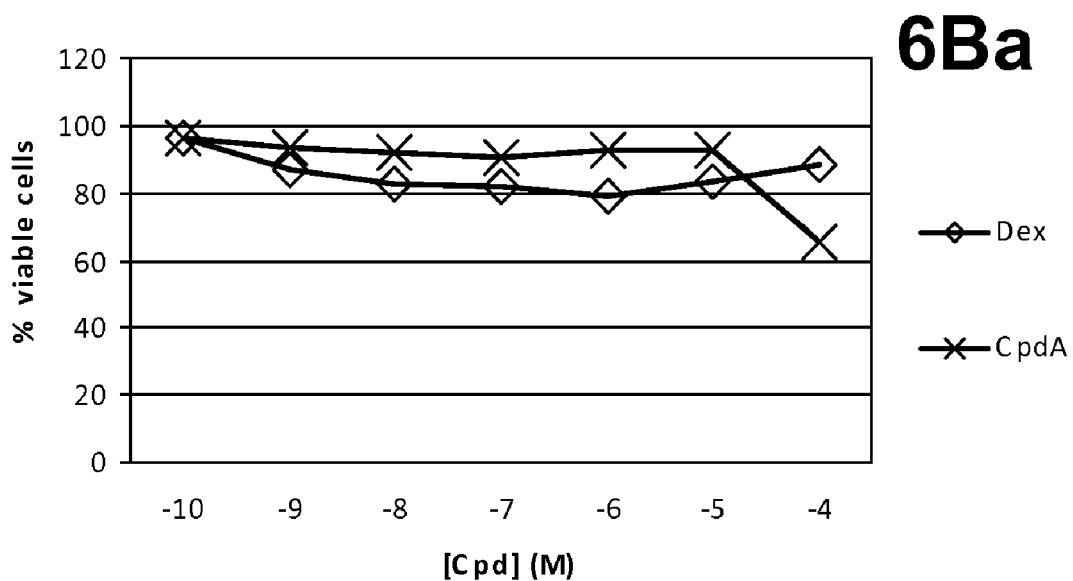
Figure 6B:
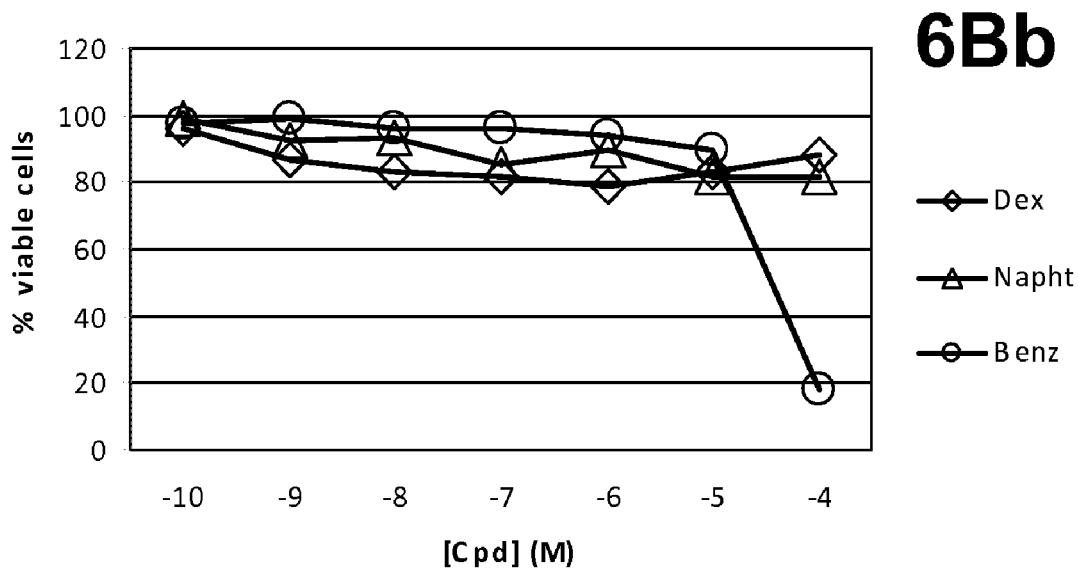

When tested at $10^{-4}$ M, CpdA blocks cell viability for 20% up to 60% in L929sA cells (FIGS. 5A and 5B) and for 20% up to 40% (24 hours compared to 48 hours) in A549 cells (FIGS. 6A and 6B). Remarkably, in A549 cells Naphth had the least effect on cell viability at $10^{-4}$ M when treated for 48 hours of only 20% (FIG. 6B). This is of particular interest, especially with regard to its potential to mediate cell killing of the immune cells, already at $10^{-5}$ M. As a reference, in L929sA cells, treatment with DEX at $10^{-4}$ M for 48 hours leads to a blockade of cell viability for 30% (FIG. 5B).

Example 352

Evaluation of the Synephrine Derivatives on Ex-Vivo Cultured Cells of Patients Suffering from Chronic Lymphocytic Leukemia (CLL)

By contrast with most other hematological malignant disorders, in which increased cell division overrides clinical presentation, B-CLL accumulation may result from deficient apoptosis rather than acute proliferation. The impaired apoptosis that occurs in B-CLL is attributed to several mechanisms, including overexpression of B-cell CLL lymphoma 2 (Bcl-2) family members, impaired activity of cell death receptors, and/or overexpression of cytokines and angiogenic factors that support the survival of B-CLL cells. Chronic lymphocytic leukemia (CLL) is at present an incurable disease. Although the mechanism of action of GC-induced apoptosis in CLL remains unknown, all of the drugs currently used in the treatment of CLL induce apoptosis in the cells, and in vitro responses to glucocorticoid or analogs correlate with in vivo sensitivity to these agents.

Blood samples were obtained from B-CLL patients after informed consent according to institutional guidelines. CLL lymphocytes were isolated using Lymphoprep (Nycomed Pharma, Denmark) and re-suspended at a final concentration of $10-30 \times 10^6$ cells/ml in RPMI 1640 medium, supplemented with 10% heat-inactivated fetal bovine serum (FBS) (Greiner Bio-one, Wemmel, Belgium), 100 IU/ml penicillin, 100 µg/ml streptomycin, and 0.56 µg/mL fungizone (Gibco BRL, Merelbeke, Belgium). B-CLL cells were cultured in Dulbecco's Modified Eagle Medium (DMEM) (Gibco, Invitrogen Inc.) containing 10% FBS (Gibco, Invitrogen Inc.). For flow cytometric analysis of apoptosis, B-CLL cells were treated with the different compounds for 24 hours, $3 \times 10^5$ cells were removed from the culture medium, washed twice with cold PBS, and double stained with annexin V-fluorescein isothiocyanate (FITC) and propidium iodide (PI; Beckman Coulter, Miami, Fla.) in Annexin binding buffer, followed by analysis on a FC500PTM (Beckman Coulter, Nyon, Switzerland) flow cytometer. Flow cytometric data were analyzed using Cytomixs RXP software (Beckman Coulter, Nyon, Switzerland). To avoid non-specific fluorescence from dead cells, live cells were gated using forward and side scatter.

One of the early signs of apoptosis is the translocation of the membrane phospholipid phosphatidylserine from the cytoplasmic interface to the extracellular surface. Annexin V has a high affinity for the phospatidylserine-containing phospholipid bilayers. Hence, fluorochrome (i.e. FITC) conjugates of AnnV can be used for detection of apoptotic cells. As the plasma membrane becomes increasingly permeable during the later stages of apoptosis, the DNA-binding dye PI can readily move across the cell membrane and bind to cellular DNA, providing a means to detect the loss of membrane integrity through mechanisms including necrosis. Three different cell populations can be observed in cells double-stained with AnnV-FITC and PI. Cells that do not stain with either AnnV or PI are live cells. Cells that stain with Ann V only are early apoptotic cells. And cells that stain with both AnnV and PI are late apoptotic/necrotic cells. The percentage of AnnV-positive B-CLL cells in the lymphocyte gate were measured by FACS and results were expressed as % apoptotic cells, i.e. sum of early apoptotic (AnnV+, PI−), and late apoptotic/dead cells (AnnV+, PI+). The percent of living cells was normalized to 100% living cells incubated in control medium with 0.1% EtOH. All measurements were made in duplicate and averaged.

As can be read from the results listed in Table 1, CpdA treatment at a concentration of $10^{-7}$ M elicits 40% and 55% apoptosis in cells from 2 different CLL patients. Solumedrol, a glucocorticoid, was also administered at $10^{-7}$ M. As CpdA treatment, in contrast to classic cortisone treatment, does not suffer from GR down-regulation, the risk of develop GR resistance is considerably less, as can be observed in CLL patient 2.

TABLE 1

|  | CLL patient 1 | CLL patient 2 |
|---|---|---|
| Untreated | 21 | 27 |
| Radiation (2Gy) | 46 | 37 |
| Chlorambucil ($25 \cdot 10^{-7}$M) | 51 | 46 |
| Fludarabine ($5 \cdot 10^{-6}$M) | 56 | 63 |
| Solumedrol ($10^{-7}$M) | 60 | 34 |
| CpdA ($10^{-6}$M) | 43 | 54 |

Example 353

Inhibition of NFκB/DNA Binding in Tumor Cell

Various tumor cells are characterized by aberrant NFκB activity as a consequence of genetic defects (i.e. allowing uncontrolled growth factor and stress signaling) or in response to DNA damage (upon exposure to chemotherapeutic drugs), which in both cases triggers NFκB-dependent anti-apoptotic gene expression and therapy resistance. In contrast, dissociated glucocorticoids with impaired transactivation function, but intact transrepression function show a potent ability to inhibit NFκB activity, sensitize tumor cells for apoptosis and prevent therapy resistance.

Inhibition of NFκB activity by CpdA and analogues in MCF7 human breast cancer cells was demonstrated by the Electrophoretic Mobility Shift Assay (hereinafter referred to as EMSA). MCF7 cells were grown in DMEM supplemented with 5% fetal calf serum, 100 units/ml penicillin, and 0.1 mg/ml streptomycin, glutamine (100× stock), Na-pyruvate (1000×), non-essential amino acids (100×) (from Gibco), 0.1 ml insulin (100 mg/ml=10000×); Namalwa B cells in RPMI supplemented with 10% fetal calf serum, 100 units/ml penicillin, and 0.1 mg/ml streptomycin; all cell lines were growth at 37° C. under 5% $CO_2$.

For the EMSA, the MCF7 cells were pre-treated with varying concentrations of CpdA (10, 1, 0.1, 0.01, and 0.001 µM) and DEX (0.1 µM) for two hours and subsequently TNF-induced or non-TNF-induced during 30 min at 2000 IU/ml. After the induction period, nuclear extracts were examined in EMSA assays. Cells were washed with ice-cold PBS, scraped off, and pelleted in 15 ml of PBS by centrifugation for 5 min at 2600 rpm at 4° C. and lysed for 30 minutes at 4° C. in Totex buffer (20 mM HEPES (pH 7.9), 350 mM NaCl, 1 mM MgCl, 0.5 mM EDTA, 0.1 mM EGTA, 5 mM DTT, 20% glycerol, 1% NP-40, 0.1% PMSF, 1% aprotinin (4 mg/ml leupeptin). Supernatants from a 4000-rpm 10-min centrifugation were collected, aliquoted and stored at −20° C. until further use. Radiolabelled oligonucleotides that correspond to a consensus κB DNA-binding element of the IL-6 promoter, and of activating protein 1 (AP-1) DNA target-were used for appropriate EMSA's. These oligonucleotides of about 25 nucleotides comprise centrally the transcription factor binding motif. Approximately 5 to 10 µg of cell extract were used in a total volume of 20 µl in a binding buffer consisting of 10 mM Tris —HCl (pH 7.5), 50 mM potassium chloride, 0.1 mM EDTA, 1 mM dithio-threitol, 5% glycerol, 0.1% NP40, 1 mM Pefabloc (Roche Molecular Biochemicals), 1 mg/ml BSA and 1 µg/ml poly (dI-dC) (Roche Molecular Biochemicals). Approximately 0.5 ng of [$\gamma^{32}$P] ATP-labeled oligonucleotides were added. The binding reactions were performed at room temperature for 30 minutes and initiated by the addition of cell extract. The samples were analyzed by electrophoresis on 6% native polyacrylamide gels. Electrophoresis was carried out at 150 V in 0.5×TBE at room temperature. Visualization and quantitation of radioactive signals was carried out by a PhosphorImager and scanned using a bioimaging analyzer (Personal Molecular Imager® FX Bio-Rad).

Figure 7A:
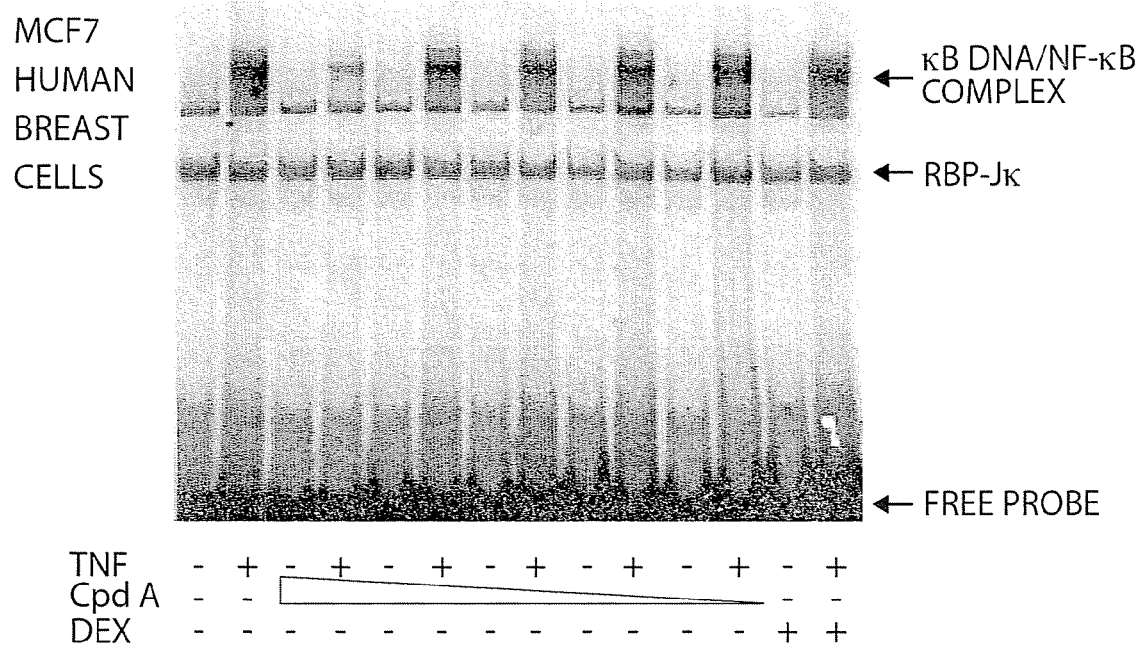
FIG. 7A shows the inhibition of NFkB DNA binding in MCF7 Human Breast cancer cells by a synephrine derivative according to certain embodiments of the invention.
Figure 7B:
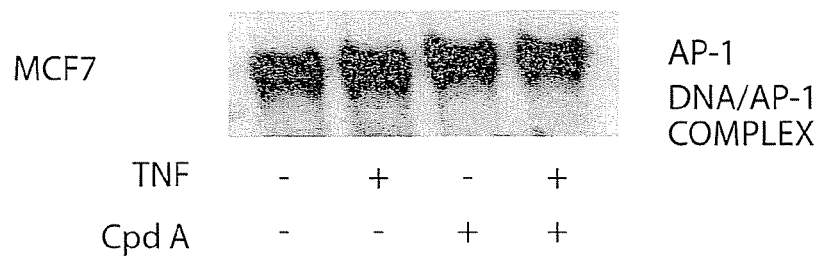
FIG. 7B shows that the DNA binding of transcription factor AP1 is not affected by CpdA.

Cell extracts of MCF7 breast cancer cells left untreated or treated as indicated in the bottom part of FIG. 7A, were incubated with radiolabelled NFkB-DNA binding sequence. As illustrated by FIG. 7A, MCF7 cells exposed to CpdA show a significant impairment of NFkB available for DNA binding. In contrast to NFkB, DNA-binding of another transcription factor, i.e. AP1, was not affected by CpdA treatment as is illustrated in FIG. 7B.

Figure 8A:
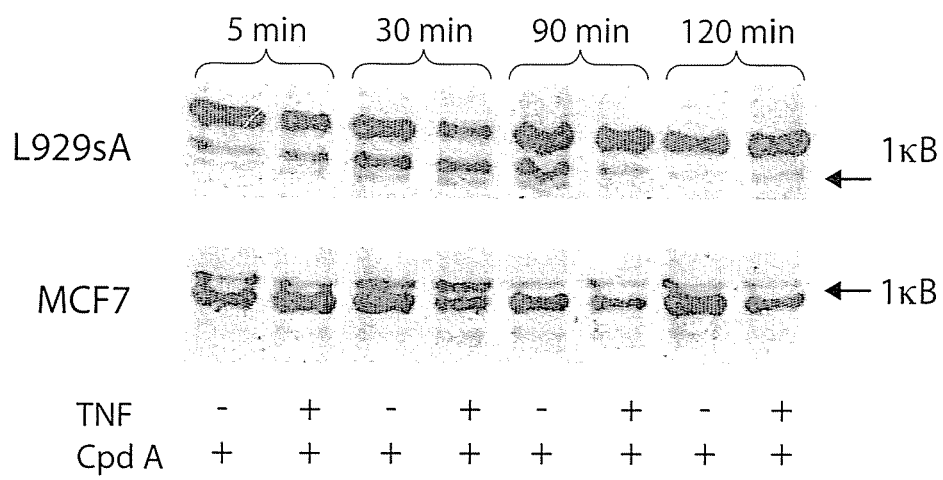
FIG. 8A shows delay in IkB-alpha degradation by CpdA in L929sA and MCF7 cells in accordance with certain embodiments of the invention.

FIG. 8A illustrates that inhibition of NFkB/DNA binding by CpdA and analogues coincides with an impaired degradation of IkB-a. This will result in sequestration of NFkB in the cytoplasm and impaired gene activation of anti-apoptotic genes. L929sA and MCF7 cells were pre-treated for two hours with CpdA (10 µM) and TNF-induced (2000 IU/ml) or not (as indicated in the bottom part of FIG. 8A). Cells were recovered at different time points for Western blot analysis to determine the IκB protein expression levels. Hereto, cells were pre-treated with 1 and 10 µM CpdA for 2 hours, followed by induction or not with 2000 IU/ml TNF for different periods of time (5, 30, 90 or 120 minutes). Cells were harvested and lysed in TOTEX buffer [20 mM HEPES/KOH pH 7.8, 0.35 M NaCl, 20% (v/v) glycerol, 1% (v/v) Nonidet P-40, 1 mM $MgCl_2$, 0.5 mM EDTA, 0.1 mM EGTA, 2 mM Pefabloc, 5 mM DTT, 1% aprotinin]. SDS-PAGE to separate proteins was performed using standard techniques. Equal amounts of total protein were mixed with 5× sample buffer (4% SDS, 10% β-mercaptoethanol, 20% glycerol in 0.125 M Tris, pH 6.8) containing bromophenol blue, boiled for 5 min, and then loaded onto a reducing 12% SDS-polyacrylamide gel, subjected to electrophoresis and transferred to a nitrocellulose membrane for 90 minutes in a refrigerated system at 150 mA, using a Tris glycine buffer system. Membranes were incubated overnight at 4° C. for blocking in TBS buffer (50 mM Tris-HCl pH 7.5, 150 mM NaCl) 0.05% Tween 20 containing 5% skim milk. After having been washed 3 times with 0.05% Tween 20 in TBS, the membrane was incubated for 1 hour at room temperature in TBS/5% milk/0.05% Tween 20 to which 1:1000 dilution of anti-IκB antibody (Santa Cruz Biotechnology) was added. After 2 hours incubation at room temperature, the membranes were washed three times with TBS/0.05% Tween 20 and incubated for 1 hour in TBS/0.05% Tween/5% milk containing 1:3000 dilution of secondary anti-rabbit Ig sheep antibody linked to HRP (Amersham). After the membranes were washed, specific proteins were detected using an enhanced chemiluminescence system (PerkinElmer). Proteins were visualised using Lumino-lmager™F1 and Lumi-Analyst 3.0 software (Mannheim Boehringer).

Figure 8B:
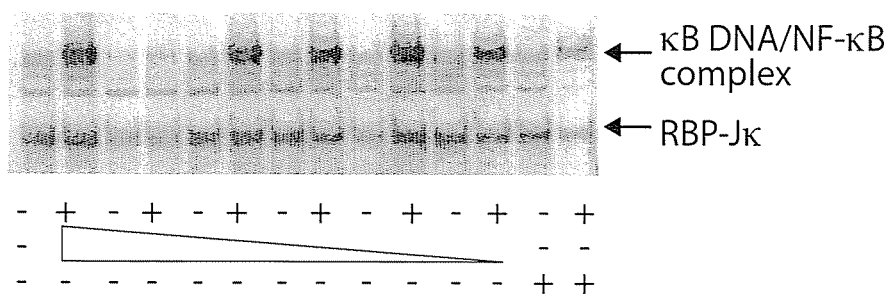
FIG. 8B shows the dose-dependent inhibition of NF-kB DNA binding by CpdA in lymphoma cell line Namalwa B in accordance with certain embodiments of the invention.

Similar effects were observed in the lymphoma cell line Namalwa B as demonstrated by FIG. 8B. FIG. 8B shows that CpdA inhibits NF-κB binding to κB DNA sequence. Namalwa B Cells were treated with CpdA (10, 0.1, 0.01, and 0.001 µM) and DEX (0.1 µM) followed by induction or non-induction with TNF (2000 IU/ml).

Example 354

Specific Gene Expression Profiling mRNA of MCF7 breast cancer cells left untreated or treated with CpdA was analyzed for variation in gene expression by means of RNase protection analysis and nylon array-filter hybridization (SuperArray filters i.e. cancer pathway finder and stress and toxicity pathway array). From these experiments it can be derived that the synephrine analogues show a unique gene expression profile with respect to target genes involved in apoptosis, cell cycle, metastasis, angiogenesis, stress responses, and the like. At the same time, the synephrine analogue-induced gene expression prophile is distinct from the gene expression response observed with classical glucorticoids. Furthermore, synephrine analogues induce a change in gene expression of NFkB-independent genes as well, which suggests that additional pathways besides the NFkB signaling cascade contribute in the anti-tumor activities of the synephrine analogues. Altogether, these data further support the use of the synephrine-derived class of dissociated glucorticoids as anti-tumor agents.

Figure 9:
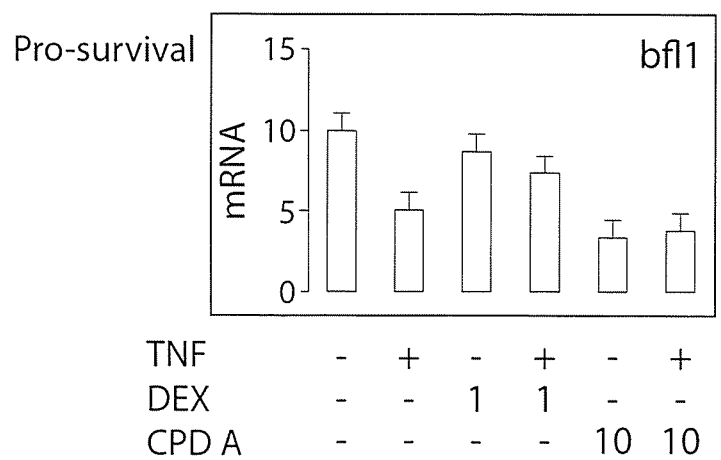
FIG. 9 shows the results of an RNAse protection analysis of the expression of an anti-apoptotoc gene after administration of Compound A (Cpd A) and/or dexamethasone (Dex).
Figure 10:
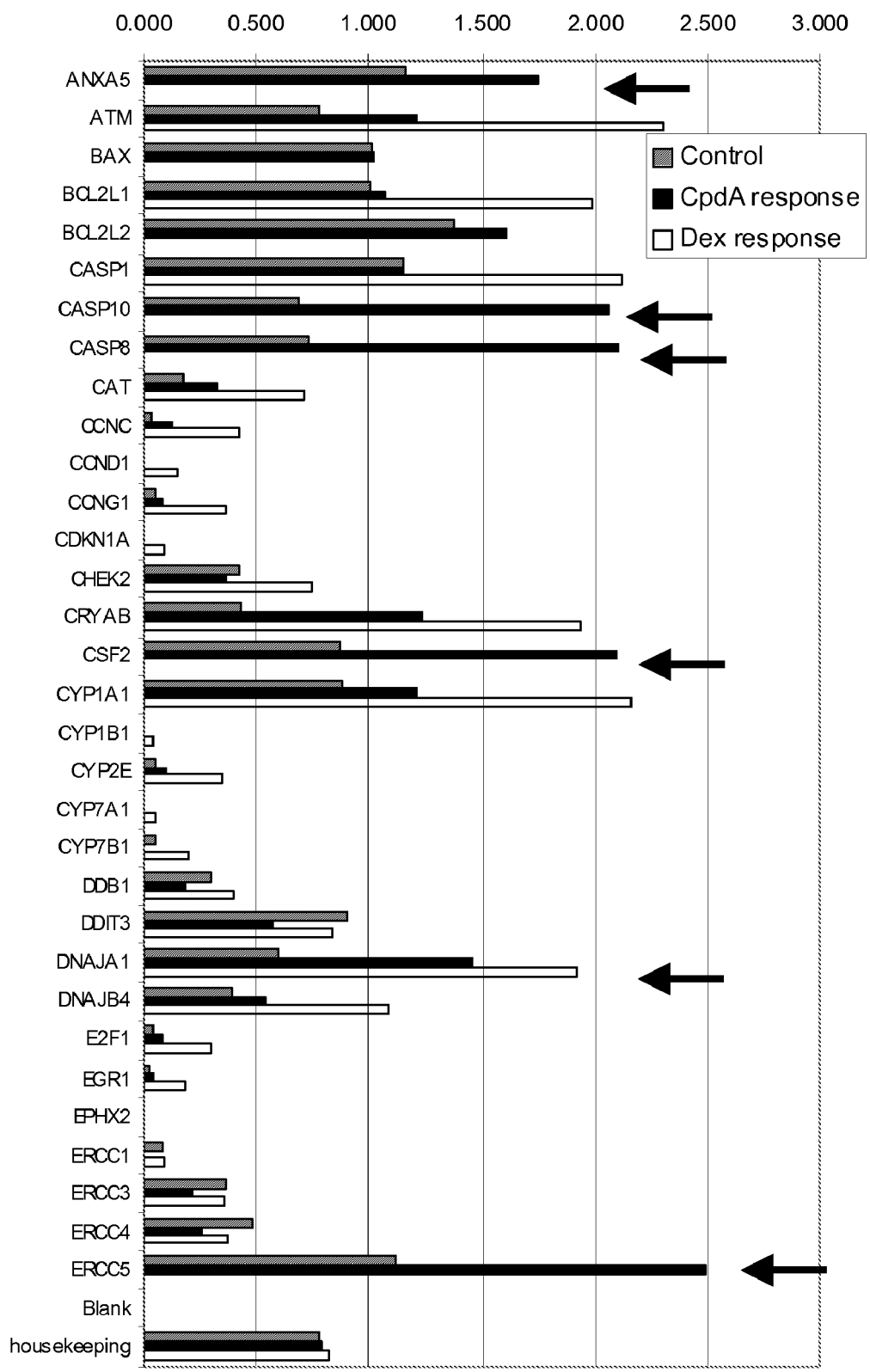
FIG. 10 shows CpdA effects on various apoptotic-related genes in MCF7 cells in accordance with certain embodiments of the invention.
Figure 11:
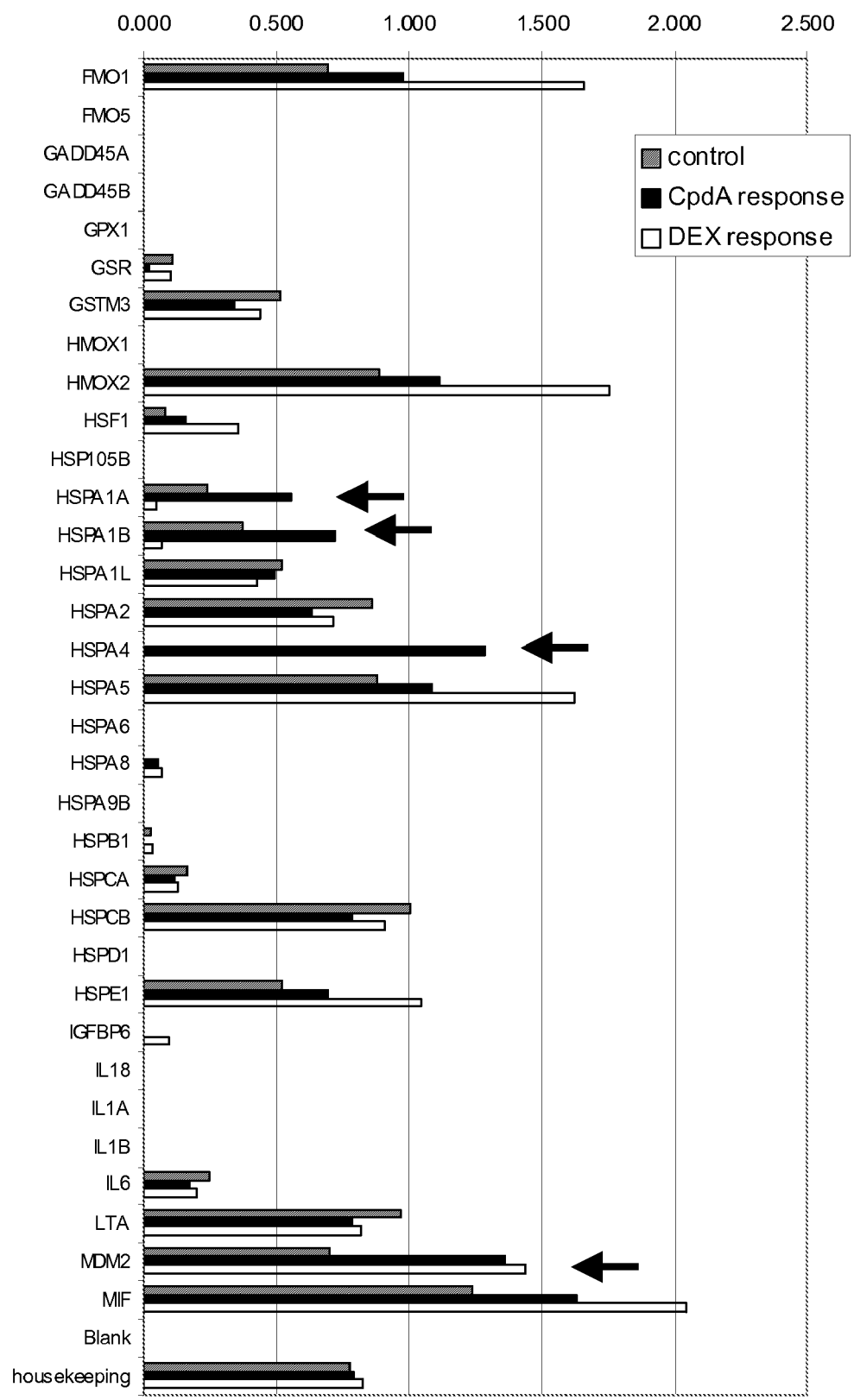
FIGS. 11 and 12 show that CpdA treatment modulates relevant stress toxicity genes in accordance with certain embodiments of the invention.
Figure 12:
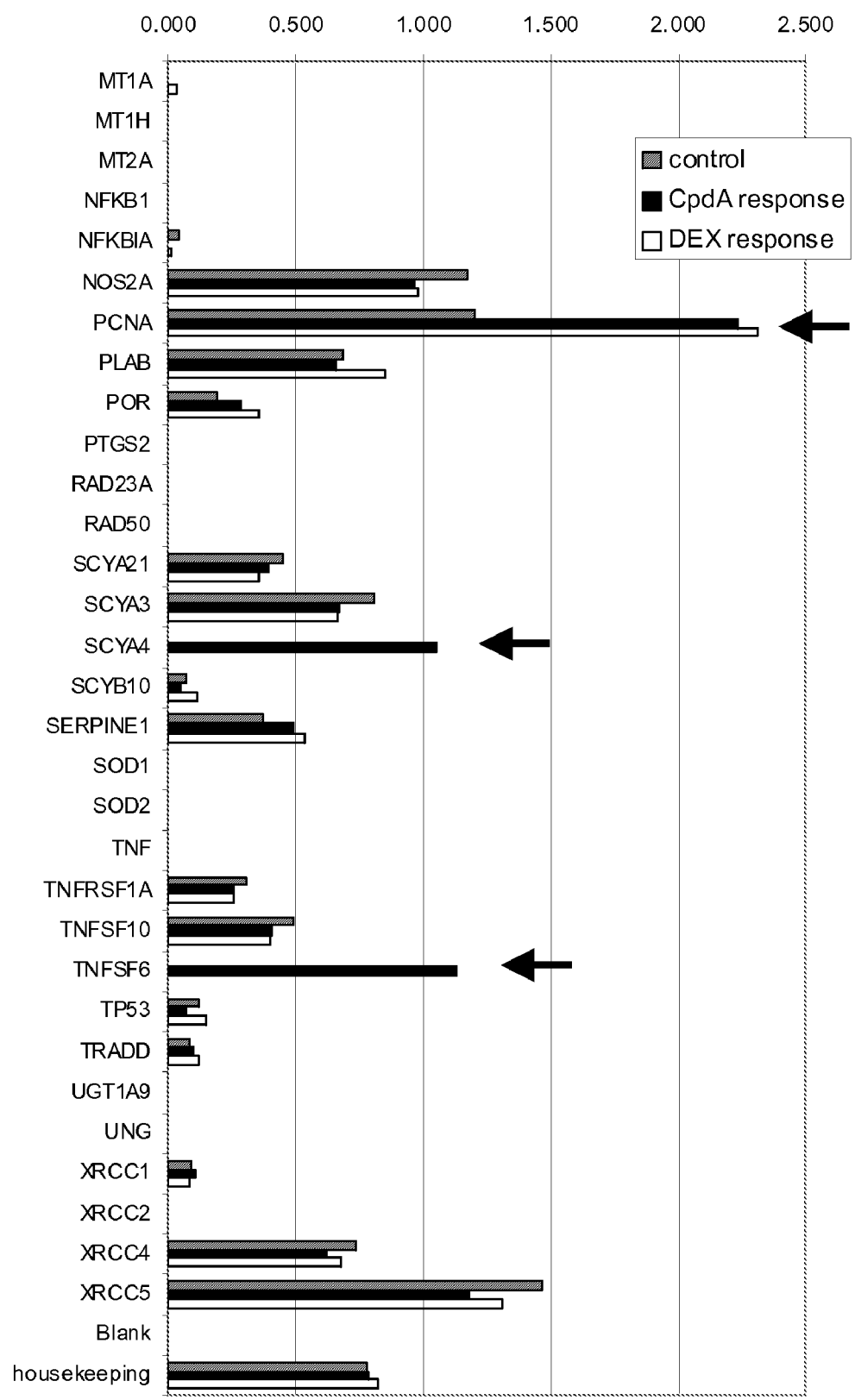

In a first specific gene expression experiment, RNAse protection analysis on the bfl1 gene, coding for BCL2-related protein A1 that has anti-apoptotic activity. FIG. 9 illustrates the results of the RNAse protection analysis. Cells were pre-treated with CpdA (10 µM) and DEX (1 µM) for 2 hours before TNF induction or non-induction for a total period of 8 hours. Total RNA was recovered (see hereunder for the total RNA extraction protocol) and an RNA protection Assay (hereinafter referred to as RPA) was performed. Transcripts were quantified by autoradiography followed by densiometry. In contrast to dexamethasone, CpdA inhibits transcription of the prosurvival gene A, i.e. bfl1 gene, which sensitizes tumor cells for apoptosis.

For the total RNA extraction, $10^5$ cell were homogenized in 1 ml of TRIzol Reagent (GIBCO BRL), incubated 5 minutes at room temperature; then added 200 µl chloroform, vortexed 15 seconds. Mix was incubated on ice for 5 minutes. Phase separation was done by centrifugation at 12000 rpm for 15 minutes at 4° C. Upper phase was recovered and mixed with equal volume (0.6 ml) isopropanol. RNA was kept at −20° C. for at least 1 hour. Samples were centrifuged at 12000 rpm for 15 minutes at 4° C. RNA pellets were washed twice with 70% ethanol in DEPC-water. Supernatant discarded respinned for one minute and aspirate residual ethanol. After drying, total RNA was resuspended in RNase free water and stored at −70° C. until use.

RNase Protection Assay (Pharmingen) was used for the detection and quantitation of A1/bfl mRNA species. MCF7 cells were seeded in 10-cm-diameter dishes at 5 $10^5$ cells/dish at day-1. Cells were pre-treated with 10 µM CpdA and 1 µM DEX for 2 hours and then TNF-induced at 2000 IU/ml for six hours. After induction, the cells were washed with ice-cold PBS, scraped off, and pelleted in 15 ml of PBS by centrifugation for 5 minutes at 2600 rpm at 4° C. Pellets were resuspended in 150 µl PBS and 50 µl RNase Later reagent (Ambion®). Total RNA was isolated using TRIzol Reagent according to the manufacturer's instructions (GIBCO BRL). RNA pellets were re-suspended in RNase-free $H_2O$ and stored at −70° C. until use. 5-10 µg of total RNA was used in the ribonuclease protection assay (RPA). The Human Apoptosis Multi-Probe Template Set hAPO-2 (PharMingen) was used to obtain radio-labelled antisense RNA probes for bfl 1, L32, and glyceraldehyde 3-phosphate dehydrogenase (GAPDH). In vitro transcription was carried out by incubation in a buffer containing 10 mM ATP, 10 mM CTP, 10 mM GTP, 250 mCia-[$^{32}$P] UTP (800 Ci/mmol, 10 mCi/mmol; AmershamPharmacia Biotech) and T7 RNA polymerase in 5× transcription buffer (PharMingen). The mixture was incubated at 37° C. for 60 minutes and then treated with DNase I at 37° C. for 30 minutes. The mixture was extracted with mixture of phenol and chloroform, and the RNA was precipitated with ethanol and collected by centrifugation at 4° C. The labelled antisense RNA probes were re-suspended in 50 µl hybridization buffer and diluted to 2.5×$10^5$ cpm/µl, and 2 µl was used per reaction. Total RNA samples were dried in a vacuum concentrator (Savant) and re-suspended in 8 µl hybridization buffer. RNA was annealed to the probe by incubating successively at 95° C. for 3 minutes and at 56° C. overnight in a total volume of 10 µl. RNase was added to each sample for removal of single-stranded RNA and RNase digestion was carried out at 30° C. for 45 minutes. The protected RNA duplexes were purified by phenol/chloroform extraction and ethanol precipitation. The pelleted RNA was re-suspended in 6 µl of gel loading buffer, incubated at 95° C. for 5 minutes, quickly quenched on ice and analyzed by electrophoresis on 6% polyacrylamide/8M urea gels. Visualization and quantitation of radioactive bands was carried out by a PhosphorImager and scanned using a bioimaging analyzer (Personal Molecular Imager® FX Bio-Rad). Densitometry analysis of autoradiograms was performed using Quantity One (Bio-Rad). Relative amounts of message were corrected for RNA loading by comparison with the L32 and glyceraldehyde-phosphate dehydrogenase band intensity for each sample and measure up to with the signal derived from untreated cells and expressed as arbitrary mRNA units.

In further experiments, nylon arrayfilter hybridization experiments were performed. cDNA array analyses were carried out according to the instructions of the manufacturer (SuperArray Simplicity GEArray™ KIT) on the cDNA arrays cancer pathway finder and stress and toxicity array. Total RNA, obtained by the protocol as described herein above, was used as a template for [$\alpha$-$^{33}$P]-cDNA probe synthesis using the following steps:

Annealing. 5 µg Total RNA, 2 µl GEAprimer Mix (buffer A, GEArray™) and RNase-free H$_2$O to a final volume of 10 µl were mixed into a sterile PCR tubes. Contents were mixed well by gentle pipetting and briefly centrifugation, subsequently mixture was placed in a thermal cycler (Perkin Elmer) at 70° C. for 10 minutes and chilled quickly on ice.

Labeling mix. Master labeling mix for each total RNA sample was prepared with the following reagents:
8 µl 5×GE labeling Buffer (Buffer B, GEArray™)
5 µl [$\alpha$-$^{33}$P]-dCTP (Amersham Pharmacial Biotech)
1 µl RNase inhibitor (Promega)
2 µl MMLV Reverse Transcriptase (Promega)
4 µl RNase-free H$_2$O Labeling was performed as follows. 20 µl of the pre-warmed labeling reagents were mixed with each annealing reaction and placed in a thermal cycler (PerkinElmer) at 42° C. for 50 minutes. Labeling reaction was stopped by adding 5 µl of 10× Stop Solution (Buffer C, GEArray™), and kept at −20° C. until further use.

A first array hybridization experiment was performed on Human Cancer Pathway Finder GEarray Q series. The array membranes were wetted with deionized water and then pre-hybridized with 2 ml of pre-heated GEAhyb Hybridization Solution containing heat-denatured sheared salmon sperm DNA (100 µg DNA/ml) at 68° C. for 2 hours with continuous agitation at 5-10 rpm/min. Pre-hybridization solution was discarded and a fresh ml of pre-hybridization solution containing the denatured [$\alpha$-$^{33}$P-cDNA probe was added for overnight hybridization with continuous agitation at 5-10 rpm/min.

Membranes were washed twice with 5 ml of pre-warmed wash solution 2×SSC, 1% SDS for 10 minutes at 68° C. with agitation at 30-40 rpm/minute. Subsequently, membranes were washed again with 5 ml of pre-warmed wash solution 0.1×SSC, 0.5% SDS for 20 min at 68° C. with agitation at 30-40 rpm/minute. Wet membranes were put in a hybridization bag and exposed with an intensifying screen for 5 days at room temperature. Visualization and quantitation of radioactive bands was carried out by a PhosphorImager and scanned using a bioimaging analyzer (Personal Molecular Imager® FX Bio-Rad). Densitometry analysis of autoradiograms was performed using Quantity One (Bio-Rad). Visualization and quantitation of radioactive signals was carried out by a PhosphorImager and scanned using a bioimaging analyzer (Personal Molecular Imager® FX Bio-Rad). Densitometry analysis of autoradiograms was performed using Quantity One (Bio-Rad). Hybridization signals were corrected for background hybridization signal and normalized for housekeeping gene expression. A complete list of genes tested for in the human cancer pathway array is given in Table 2.

The result of the array showed that $10^{-5}$ M CpdA treatment represses the following relevant cancer target genes involved in:

Cell cycle control and DNA damage repair: TP53
Apoptosis and cell senescence: TNFRSF12
Signal transduction—Transcription factors: MAP2K1, RAF
Adhesion: ITGA6, NCAM
Angiogenesis: PDGF
Invasion and metastasis MMP9, MTA1, TIMP1

TABLE 2

| Symbol | Description | Gene Name |
|---|---|---|
| AKT1 | V-akt murine thymoma viral oncogene homolog 1 | AKT/PKB |
| ANGPT1 | Angiopoietin 1 | AGP1/AGPT |
| ANGPT2 | Angiopoietin 2 | AGPT2/ANG2 |
| APAF1 | Apoptotic peptidase activating factor 1 | CED4 |
| ATM | Ataxia telangiectasia mutated (includes complementation groups A, C and D) | AT1/ATA |
| BAD | BCL2-antagonist of cell death | BBC2/BCL2L8 |
| BAX | BCL2-associated X protein | Bax zeta |
| BCL2 | B-cell CLL/lymphoma 2 | Bcl-2 |
| BCL2L1 | BCL2-like 1 | BCL-XL/S |
| BRCA1 | Breast cancer 1, early onset | BRCAI/BRCC1 |
| CASP8 | Caspase 8, apoptosis-related cysteine peptidase | CAP4/FLICE |
| CCNE1 | Cyclin E1 | CCNE |
| CDC25A | Cell division cycle 25 homolog A (*S. pombe*) | CDC25A2 |
| CDK2 | Cyclin-dependent kinase 2 | p33(CDK2) |
| CDK4 | Cyclin-dependent kinase 4 | CMM3/PSK-J3 |
| CDKN1A | Cyclin-dependent kinase inhibitor 1A (p21, Cip1) | CAP20/CDKN1 |
| CDKN2A | Cyclin-dependent kinase inhibitor 2A (melanoma, p16, inhibits CDK4) | ARF/CDK4I |
| CFLAR | CASP8 and FADD-like apoptosis regulator | CASH/CASP8AP1 |
| CHEK2 | CHK2 checkpoint homolog (*S. pombe*) | CDS1/CHK2 |
| COL18A1 | Collagen, type XVIII, alpha 1 | KNO |
| E2F1 | E2F transcription factor 1 | E2F-1/RBBP3 |

TABLE 2-continued

| Symbol | Description | Gene Name |
|---|---|---|
| ERBB2 | V-erb-b2 erythroblastic leukemia viral oncogene homolog 2, neuro/glioblastoma derived oncogene homolog (avian) | HER-2/HER-2 |
| ETS2 | V-Ets erythroblastosis virus E26 oncogene homolog 2 (avian) | C-Ets2 |
| FAS | Fas (TNF receptor superfamily, member 6) | ALPS1A/APO-1 |
| FGFR2 | Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | BEK/BFR-1 |
| FOS | V-fos FBJ murine osteosarcoma viral oncogene homolog | c-fos |
| GZMA | Granzyme A (granzyme 1, cytotoxic T-lymphocyte-associated serine esterase 3) | CTLA3/HFSP |
| HTATIP2 | HIV-1 Tat interactive protein 2, 30 kDa | CC3/TIP30 |
| IFNA1 | Interferon, alpha 1 | IFL/IFN |
| IFNB1 | Interferon, beta 1, fibroblast | IFB/IFF |
| IGF1 | Insulin-like growth factor 1 (somatomedin C) | IGFI |
| IL8 | Interleukin 8 | 3-10C/AMCF-I |
| ITGA1 | Integrin, alpha 1 | CD49a/VLA1 |
| ITGA2 | Integrin, alpha 2 (CD49B, alpha 2 subunit of VLA-2 receptor) | BR/CD49B |
| ITGA3 | Integrin, alpha 3 (antigen CD49C, alpha 3 subunit of VLA-3 receptor) | CD49C/GAP-B3 |
| ITGA4 | Integrin, alpha 4 (antigen CD49D, alpha 4 subunit of VLA-4 receptor) | CD49D/IA4 |
| ITGAV | Integrin, alpha V (vitronectin receptor, alpha polypeptide, antigen CD51) | CD51/MSK8 |
| ITGB1 | Integrin, beta 1 (fibronectin receptor, beta polypeptide, antigen CD29 includes MDF2, MSK12) | CD29/FNRB |
| ITGB3 | Integrin, beta 3 (platelet glycoprotein IIIa, antigen CD61) | CD61/GP3A |
| ITGB5 | Integrin, beta 5 | FLJ26658 |
| JUN | Jun oncogene | AP1/c-Jun |
| MAP2K1 | Mitogen-activated protein kinase kinase 1 | MAPKK1/MEK1 |
| MCAM | Melanoma cell adhesion molecule | CD146/MUC18 |
| MDM2 | Mdm2, transformed 3T3 cell double minute 2, p53 binding protein (mouse) | HDMX/hdm2 |
| MET | Met proto-oncogene (hepatocyte growth factor receptor) | HGFR/RCCP2 |
| MMP1 | Matrix metallopeptidase 1 (interstitial collagenase) | CLG/CLGN |
| MMP2 | Matrix metallopeptidase 2 (gelatinase A, 72 kDa gelatinase, 72 kDa type IV collagenase) | CLG4/CLG4A |
| MMP9 | Matrix metallopeptidase 9 (gelatinase B, 92 kDa gelatinase, 92 kDa type IV collagenase) | CLG4B/GELB |
| MTA1 | Metastasis associated 1 | Mta-1 |
| MTA2 | Metastasis associated 1 family, member 2 | DKFZp686F2281/MTA1L1 |
| MTSS1 | Metastasis suppressor 1 | MIM/MIMA |
| MYC | V-myc myelocytomatosis viral oncogene homolog (avian) | c-Myc |
| NFKB1 | Nuclear factor of kappa light polypeptide gene enhancer in B-cells 1 (p105) | DKFZp686C01211/EBP-1 |
| NFKBIA | Nuclear factor of kappa light polypeptide gene enhancer in B-cells inhibitor, alpha | IKBA/MAD-3 |
| NME1 | Non-metastatic cells 1, protein (NM23A) expressed in | AWD/GAAD |
| NME4 | Non-metastatic cells 4, protein expressed in | NM23H4/nm23-H4 |
| PDGFA | Platelet-derived growth factor alpha polypeptide | PDGF-A/PDGF1 |
| PDGFB | Platelet-derived growth factor beta polypeptide (simian sarcoma viral (v-sis) oncogene homolog) | PDGF2/SIS |
| PIK3R1 | Phosphoinositide-3-kinase, regulatory subunit 1 (p85 alpha) | GRB1/p85-ALPHA |
| PLAU | Plasminogen activator, urokinase | ATF/UPA |
| PLAUR | Plasminogen activator, urokinase receptor | CD87/UPAR |
| PNN | Pinin, desmosome associated protein | DRS/SDK3 |
| RAF1 | V-raf-1 murine leukemia viral oncogene homolog 1 | CRAF/Raf-1 |
| RB1 | Retinoblastoma 1 (including osteosarcoma) | OSRC/RB |
| S100A4 | S100 calcium binding protein A4 | 18A2/42A |
| SERPINB5 | Serpin peptidase inhibitor, clade B (ovalbumin), member 5 | PI5/maspin |
| SERPINE1 | Serpin peptidase inhibitor, clade E (nexin, plasminogen activator inhibitor type 1), member 1 | PAI/PAI-1 |
| SNCG | Synuclein, gamma (breast cancer-specific protein 1) | BCSG1/SR |
| SYK | Spleen tyrosine kinase | Syk |
| TEK | TEK tyrosine kinase, endothelial (venous malformations, multiple cutaneous and mucosal) | CD202B/TIE-2 |
| TERT | Telomerase reverse transcriptase | EST2/TCS1 |
| TGFB1 | Transforming growth factor, beta 1 | CED/DPD1 |
| TGFBR1 | Transforming growth factor, beta receptor I (activin A receptor type II-like kinase, 53 kDa) | AAT5/ACVRLK4 |
| THBS1 | Thrombospondin 1 | THBS/TSP |
| TIMP1 | TIMP metallopeptidase inhibitor 1 | CLGI/EPA |
| TIMP3 | TIMP metallopeptidase inhibitor 3 (Sorsby fundus dystrophy, pseudoinflammatory) | HSMRK222/K222 |

TABLE 2-continued

| Symbol | Description | Gene Name |
|---|---|---|
| TNF | Tumor necrosis factor (TNF superfamily, member 2) | DIF/TNF-alpha |
| TNFRSF10B | Tumor necrosis factor receptor superfamily, member 10b | CD262/DR5 |
| TNFRSF1A | Tumor necrosis factor receptor superfamily, member 1A | CD120a/FPF |
| TNFRSF25 | Tumor necrosis factor receptor superfamily, member 25 | APO-3/DDR3 |
| TP53 | Tumor protein p53 (Li-Fraumeni syndrome) | LFS1/TRP53 |
| TWIST1 | Twist homolog 1 (acrocephalosyndactyly 3; Saethre-Chotzen syndrome) (*Drosophila*) | ACS3/BPES2 |
| EPDR1 | Ependymin related protein 1 (zebrafish) | EPDR/MERP-1 |
| VEGFA | Vascular endothelial growth factor A | VEGF/VEGF-A |
| B2M | Beta-2-microglobulin | B2M |
| HPRT1 | Hypoxanthine phosphoribosyltransferase 1 (Lesch-Nyhan syndrome) | HGPRT/HPRT |
| RPL13A | Ribosomal protein L13a | RPL13A |
| GAPDH | Glyceraldehyde-3-phosphate dehydrogenase | G3PD/GAPD |
| ACTB | Actin, beta | PS1TP5BP1 |
| HGDC | Human Genomic DNA Contamination | HIGX1A |
| RTC | Reverse Transcription Control | RTC |
| RTC | Reverse Transcription Control | RTC |
| RTC | Reverse Transcription Control | RTC |
| PPC | Positive PCR Control | PPC |
| PPC | Positive PCR Control | PPC |
| PPC | Positive PCR Control | PPC |

A second array hybridization experiment was performed on Human Stress and Toxicity Pathway Finder GEarray Q series. The same protocol was followed as for the array hybridization experiment on the Human Cancer Pathway Finder described herein above. Results indicated that $10^{-5}$ M CpdA treatment modulates relevant stress toxicity target genes and can be summarized as follows:

increased gene response under CpdA treatment (similar to the response under treatment with $10^{-6}$ M DEX)
Oxidative or metabolic stress: CRYAB
Heat shock: DNAJA1
Proliferation and carcinogenesis: pcna
Growth arrest and senescence: mdm2
Different gene response under CpdA treatment when compared to DEX
CpdA but not DEX increases levels of
Heat shock: HSPA1A, HSPA1B, HSPA4 (=hsp70)
Inflammation: CSF2, SCYA4 (MIP1B)
Necrosis or apoptosis: ANXA5, casp10, casp8, ERCC5, TNFSF6 (FasL)
DEX but not CpdA increases levels of
Oxidative or metabolic stress: cyp1A1, FMO1, HMOX2
Necrosis or apoptosis: ATM, bcl2L1, casp1,
DEX but not CpdA decreases levels of
Heat shock: hspA1A, 1B FIGS. 7 to 9 illustrate the level of gene expression of the genes tested for in the stress and toxicity pathway array. A complete list of genes tested for in the stress and toxicity pathway array is given in the following table:

| Symbol | Gene name |
|---|---|
| ANXA5 | Annexin V |
| ATM | Ataxia telangiectasia mutated (includes complementation groups A, C and D) |
| BAX | BCL2-associated X protein |
| BCL2L1 | BCL2-like 1 |
| BCL2L2 | BCL2-like 2 |
| CASP1 | Caspase 1, apoptosis-related cystein |
| CASP10 | Caspase 10, apoptosis-related cystein |
| CASP8 | Caspase 8, apoptosis-related cystein |
| CAT | Catalase |
| CCNC | G1/S-SPECIFIC CYCLIN C |
| CCND1 | Cyclin D1 (also referred to as PRAD1 or BCL1) |
| CCNG1 | Cyclin G1 |
| CDKN1A | Cyclin-dependent kinase inhibitor 1A |
| CHEK2 | Protein kinase Chk2 |
| CRYAB | Alpha crystallin B |
| CSF2 | Colony stimulating factor 2 (also referred to as granulocyte-macrophage colony-stimulating factor, GMCSF) |
| CYP1A1 | Cytochrome P450, subfamily I (aromatic compound-inducible), polypeptide 1 |
| CYP1B1 | Cytochrome P450, subfamily I (dioxin-inducible), polypeptide 1 (glaucoma 3, primary infantile) |
| CYP2E | Cytochrome P450, subfamily IIE (ethanol-inducible) |
| CYP7A1 | Cytochrome P450, subfamily VIIA (cholesterol 7 alpha-monooxygenase), polypeptide 1 |
| CYP7B1 | Cytochrome P450, subfamily VIIB (oxysterol 7 alpha-hydroxylase), polypeptide 1 |
| DDB1 | damage-specific DNA binding protein 1 (217 kD) |
| DDIT3 | DNA-damage-inducible transcript 3 |
| DNAJA1 | DnaJ (Hsp40) homolog, subfamily A, member 1 |
| DNAJB4 | DnaJ (Hsp40) homolog, subfamily B, member 4 |
| E2F1 | E2F transcription factor 1 |
| EGR1 | Early growth response 1 |
| EPHX2 | epoxide hydrolase 2, cytoplasmic |
| ERCC1 | excision repair cross-complementing rodent repair deficiency, complementation group 1 |
| ERCC3 | excision repair cross-complementing rodent repair deficiency, complementation group 3 |
| ERCC4 | *Homo sapiens* excision repair protein ERCC4 |
| ERCC5 | excision repair cross-complementing rodent repair deficiency, complementation group 5 |
| FMO1 | Human flavin-containing monooxygenase (FMO1) |
| FMO5 | *Homo sapiens* flavin containing monooxygenase 5 (FMO5) |
| GADD45A | DNA-damage-inducible transcript 1 |
| GADD45B | growth arrest- and dna damage-inducible gene GADD45- BETA (also referred to as MYD118) |
| GPX1 | Glutathione peroxidase 1 |
| GSR | Glutathione reductase |
| GSTM3 | glutathione S-transferase M3 (brain) |
| HMOX1 | Heme oxygenase (decycling) 1 |
| HMOX2 | Heme oxygenase (decycling) 2 |
| HSF1 | Heat shock transcription factor 1 |
| HSP105B | Heat shock 105 kD |
| HSPA1A | Heat shock 70 kD protein 1A |
| HSPA1B | Heat shock 70 kD protein 1B |
| HSPA1L | Heat shock 70 kD protein- like 1 |

-continued

| Symbol | Gene name |
|---|---|
| HSPA2 | Heat shock 70 kD protein 2 |
| HSPA4 | Hum an heat shock protein 70 (hsp70) |
| HSPA5 | Grp78 (78 KD glucose regulated protein) |
| HSPA6 | Heat shock 70 kD protein 6 (HSP70B') |
| HSPA8 | Heat shock 70 kD protein 8 |
| HSPA9B | Heat shock 70 kD protein 9B (mortalin-2) |
| HSPB1 | Heat shock 27 KD protein |
| HSPCA | Hsp90 (Human mRNA for 90-kDa heat-shock protein) |
| HSPCB | Heat shock 90 kD protein 1, beta |
| HSPD1 | Heat shock 60 kD protein 1 (chaperonin) |
| HSPE1 | Heat shock 10 kD protein 1 (chaperonin 10) |
| IGFBP6 | IGFBP6 |
| IL18 | Interleukin 18 (interferon-gamma-inducing factor) |
| IL1A | Interleukin 1, alpha |
| IL1B | Interleukin 1, beta |
| IL6 | Interleukin 6 (interferon, beta 2) |
| LTA | Lym photoxin-alpha (TNF superfamily, member 1) |
| MDM2 | Mouse double minute 2, human homolog of; p53-binding protein |
| MIF | Macrophage migration inhibitory factor |
| MT1A | metallothionein 1A (functional) |
| MT1H | metallothionein 1H |
| MT2A | metallothionein 2A |
| NFKB1 | Nuclear factor of kappa light polypeptide gene enhancer in B-cells |
| NFKBIA | Nuclear factor of kappa light polypeptide gene enhancer in B-cells |
| NOS2A | Inducible nitric oxide synthase (iNOS) |
| PCNA | Proliferating cell nuclear antigen |
| PLAB | Prostate differentiation factor |
| POR | NADPH-cytochrom e p450 reductase |
| PTGS2 | Homo sapiens prostaglandin-endoperox-idesynthase 2 |
| RAD23A | UV excision repair protein RAD 23 |
| RAD50 | RAD50 (S. cerevisiae) homolog |
| SCYA21 | Small inducible cytokine subfam ily A (CysCys), member 21 |
| SCYA3 | Small inducible cytokine A3 (homologous to mouse Mip-1a) |
| SCYA4 | Small inducible cytokine A4 (homologous to mouse Mip-1b) |
| SCYB10 | Gamma-interferon inducibie early response gene |
| SERPINE1 | Plasminogen activator inhibitor, type I |
| SOD1 | Cu/Zn superoxide dismutase |
| SOD2 | Human mRNA for manganese superoxide dismutase |
| TNF | Tumor necrosis factor (TNF super family, member 2) |
| TNFRSF1A | Tumor necrosis factor receptor super family, member 1A |
| TNFSF10 | Tumor necrosis factor (ligand) super-family, member 10 |
| TNFSF6 | Ligand for Fas |
| TP53 | Tumor protein p53 (Li-Fraumeni syndrome) |
| TRADD | Homo sapiens TNF receptor -1 associated protein |
| UGT1A9 | Homo sapiens UDP glycosyltransferase 1 family, polypeptide A9 |
| UNG | Human cDNA for uracil-DNA glycosylase |
| XRCC1 | Human DNA-repair protein (XRCC1) |
| XRCC2 | Homo sapiens mRNA for RAD51-like protein (XRCC2) |
| XRCC4 | XRCC4 X-ray repair complementing defec-tive repair in Chinese |
| XRCC5 | Human Ku (p707p80) subunit |
| PUC18 | PUC18 Plasm id DNA |
| Blank | Blank |
| GAPD | Glyceraldehyde-3-phosphate dehydrogenase |
| PPIA | Homo sapiens peptidylprolyl isomerase A (cyclophilin A) (PPIA) |
| RPL13A | Ribosomalprotein L13a |
| ACTB | Beta Actin |

Example 355

Annexin V/Propidiumiodide (PI) Assay

1. To show that the reduced viability of the multiple myeloma cell lines, that we observed in the MTT assays in example 1 herein above, is the result of the induction of apoptosis by the synephrine analogs of the present invention, we perform the Annexin V/PI staining (similar to the MTT test on B-CLL cells in example 1).

Procedure:

Human multiple myeloma cell lines L363, U266, MM1.S and MMR.1 are cultured in RPMI 1640 with Glutamax-I, supplemented with 10% FCS, 100 U/ml penicillin and 100 µg/ml streptomycin. Cells are counted and resuspended in fresh medium at a concentration of $1 \times 10^6$/ml. Next, 1 ml of cell suspension is transferred to 5 ml culture tubes in the presence of test compounds (DEX, CpdA, CpdA analogues: $10^{-7}$ to $10^{-4}$ M) or vehicle (EtOH) and incubated for 24 or 48 hours at 37° C.

Double-staining of the cells with PI and annexin V is performed according to the instructions of the Annexin V kit (BD Biosciences).

Double-stained cells are analyzed by flow cytometry.

Figure 13:
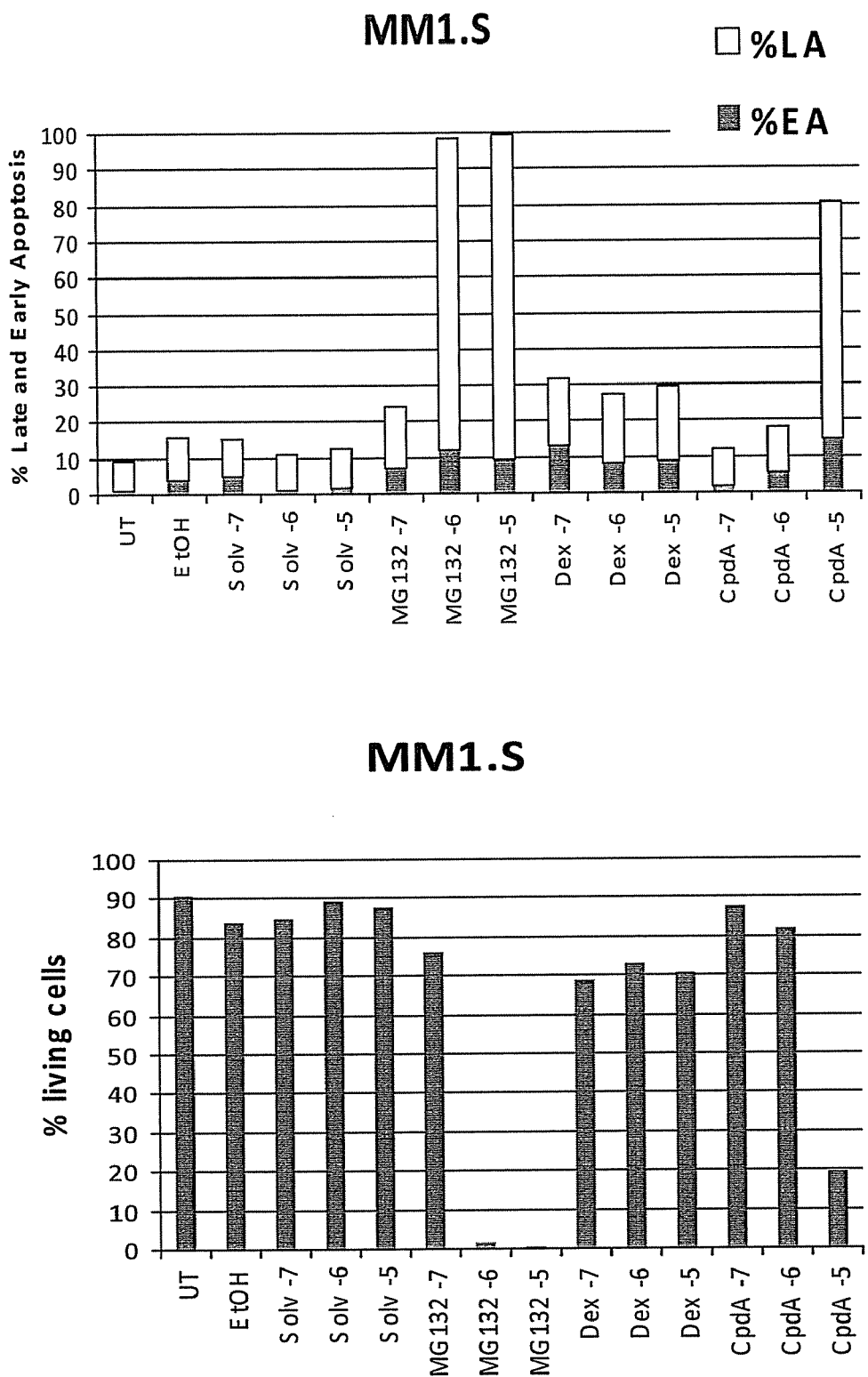
FIG. 13 shows the effect on apoptisis (Annexin V/PI staining) to address apoptosis.
LA: late apoptosis, EA: early apoptosis, UT: untreated, Solv: solvent controls, MG132: a proteasome inhibitor and positive control mediating apoptosis, Dex: Dexamethasone, a synthetic glucocorticoid. Affixes-7, -6 and -5 correspond to 10-7M, 10-6M and 10-5M, respectively.

FIG. 13 shows that in the sensitive assay for monitoring apoptosis, synephrine derivatives such as CpdA are able to mediate apoptosis in the MM1.S cell lines at 10-5 M, to a much higher extent than Dex, a strong agonist of the Glucocorticoid Receptor. As expected, the positive control MG132 also mediates apoptosis. Graphs are represented as the ratio of early apoptotic cells versus late apoptotic cells (a) or as total % of living cells (b).

Example 356

Analysis of Anti-Apoptotic Protein Expression

To confirm that the synephrine analogs of the present invention induce apoptosis in multiple myeloma cells, we investigate the expression of genes implicated in cell proliferation (cyclin D1) and survival (cIAP-2, XIAP, survivin, Bcl-2, Bcl-xL and TRAF2). The expression of these anti-apoptotic genes is studied by western blotting.

Procedure:

Human multiple myeloma cell lines L363, U266, MM1.S and MMR.1 are cultured in RPMI 1640 with Glutamax-I, supplemented with 10% FCS, 100 U/ml penicillin and 100 µg/ml streptomycin. Cells are counted and resuspended in fresh medium at a concentration of $1 \times 10^6$/ml. Next, 2 ml of cell suspension is transferred to 5 ml culture tubes in the presence of test compounds (DEX, CpdA, CpdA analogues: $10^{-5}$ M) or vehicle (EtOH) and incubated for 24 hours at 37° C.

Cells are washed with cold PBS and pellets are lysed in 50 µl of Laemmli sample buffer.

Cell extracts are separated on SDS-PAGE gels.

After transfer from the proteins to nitrocellulose membranes by western blotting, membranes are incubated with specific primary antibodies to cyclin D1, cIAP-2, XIAP, survivin, Bcl-2, Bcl-xL or TRAF2.

Incubation of the blots with a secondary antibody, that is coupled to horseradish peroxidase and that recognizes the primary antibody species IgG, allows detection of the immunoreactive proteins by chemiluminescent detection.

Example 357

Effect on Ex-Vivo Human Multiple Myeloma Cell Survival

To show that synephrine analogs of the present invention also induce apoptosis in primary human multiple myeloma cells, we perform Annexin V/PI assays (as described in example 351) on CD138$^+$-enriched cells (=plasma cells) from bone marrow aspirates of patients with multiple myeloma.

Example 358

Effect on In Vivo Multiple Myeloma Progression

To show that CpdA induces multiple myeloma cell apoptosis in vivo, we show the antitumor activity of the selected synephrine analogues with the most potent apoptosis-inducing action in the above-described experiments in the 5T33MM mouse multiple myeloma model.
Procedure:
Three groups of 10 mice are given intravenous injections of the 5T33MM multiple myeloma cells. One group of 10 naïve mice is included as negative control.
Group 1 is treated with CpdA or analogue (dose 1, injected intraperitoneally), group 2 is treated with CpdA or analogue (dose 2, injected intraperitoneally) and group 3 is treated with vehicle (PBS, injected intraperitoneally).
To assess tumor burden, at week 3, when the vehicle controls show signs of morbidity, the mice are sacrificed and the following parameters are evaluated:
1) Bone marrow is isolated and tumor load is determined by FACS staining with 5T33MM anti-idiotype-specific antibodies.
2) Blood samples are obtained to determine serum paraprotein concentrations.
3) Liver and spleen are removed and weighed.

Example 359

Confirmation of the Pro-Apoptotic Action of the Synephrine Analogs of the Present Invention on Primary CLL Cells Ex Vivo To show that the selected synephrine analogues also induce apoptosis in primary chronic lymphocytic leukemia cells (ex vivo material from patients), we perform Annexin V/PI assays (as described in example 351) on B-enriched CLL cells from blood isolates of CLL patients
Procedure:
Blood samples are obtained from B-CLL patients after informed consent according to institutional guidelines. CLL lymphocytes were isolated using Lymphoprep (Nycomed Pharma, Denmark) and resuspended at a final concentration of 10–30×106 cells/ml in RPMI 1640, supplemented with 10% heat-inactivated fetal bovine serum (FBS) (Greiner Bio-one, Wemmel, Belgium), 100 IU/ml penicillin, 100 µg/ml streptomycin, and 0.56 µg/mL fungizone (Gibco BRL, Merelbeke, Belgium). For flow cytometric analysis (FACS) of cell death, B-CLL cells were washed three times with ice-cold PBS and 10×105 cells were stained with annexin V (AnnV)-FITC (Bender MedSystems Diagnostics, Vienna, Austria) and propidium iodide (PI) (Sigma). The percentage of AnnV-positive B-CLL cells in the lymphocyte gate were measured by FACS and results were expressed as % apoptotic cells, i.e. sum of early apoptotic (AnnV+, PI−), and late apoptotic/dead cells (AnnV+, PI+). The percent of living cells was normalized to 100% living cells incubated in control medium with 0.1% EtOH. All measurements are made in duplicate and averaged.

Dose response apoptosis curves are established of the various synephrine analogs of the present invention in different patient samples to compare IC50 values in patients with a different clinical background (prior/after chemotherapy, drug resistant versus sensitive, mutated versus unmutated Ig, ZAP70 positive/negative status). IC50 values will be correlated with expression of genes implicated in cell proliferation (cyclin D1) and survival (cIAP-2, XIAP, survivin, Bcl-2, Bcl-xL) or apoptosis (e.g. p53, Bim, PUMA). The expression of these genes is studied by QPCR and western blotting. In addition caspase3 and PARP cleavage will be evaluated as apoptosis markers

Example 360

Confirmation of the Pro-Apoptotic Action of the Synephrine Analogs of the Present Invention on Tumor Cell Models (Solid Tumors)

To show that the selected synephrine analogs also induce apoptosis in solid cancer cell models:
Procedure:
Following tumor cell models are evaluated for cytostatic or cytotoxic responses of the synephrine analogs:
prostate cancer cells: LNCaP, DU145
breast cancer cells: MCF7, MDAMB231
melanoma cells: B16BL6, SK MEL 37, SK-28, 624mel and 1363mel
neuroblastoma cells: IMR32
The following experiments are realised:
Dose response curves of CpdA and analogues in MTT assay, fluorimetric cytotoxicity assays or FACS
Determine apoptotic gene expression signature upon cellular treatment with CpdA/analogues versus Dex treatment: more particularly, we measure gene expression of pro/antiapoptotic genes, cell cycle genes, angiogenesis, DNA repair, as specified in more detail below (preliminar data available). Gene expression data of genes of interest are verified at the protein level by Western analysis. Target genes to be evaluated will be selected from the list given in example 356.

Example 361

Confirmation of the Pro-Apoptotic Action of the Synephrine Analogs of the Present Invention in Solid Tumor Models In-Vivo In vivo melanoma model
Cells of B16BL6 melanoma, PG19 melanoma and Lewis Lung Carcinoma are kept in culture in DMEM supplemented with fetal calf serum, antibiotics and L-glutamine. Cells are harvested, washed three times in LPS-free PBS, and brought to a density of 6×10$^6$/ml (B16BL6) or 20×10$^6$/ml (PG19, EL4 and LLC). 100 µl of the cell suspension is injected subcutaneously into shaven, right hind limbs of the mice. When the tumors reach a size of 50-70 mm$^2$, daily treatment is started with dexamethasone (DEX), hydrocortisone (HYDRO), compound A (CpdA) or its analogues (intraperitoneally (i.p.) or in drinking water). DEX, HYDRO are diluted in PBS; CpdA is diluted in 20% ethanol. The smaller and larger diameters of the tumor are measured daily with an electronic caliper. Tumor size index (TSI) is defined in mm² as (a)×(b), (a) being the longest diameter of the tumor and (b) the diameter perpendicular to (a). Daily intraperitoneous administration of 100 µg DEX inhibits tumor growth significantly. Administration of DEX in the drinking water (100 mg/l) also slows down tumor growth. Each mouse receives daily either PBS or a specific dose of DEX, ranging from 5 µg to 200 µg. All doses show some effect on tumor growth, but the highest doses are the most effective. A dose of 50 µg DEX markedly inhibits tumor growth as measured by tumor size index and reduces tumor weight by the end of treatment. After eight days of treatment with 200 µg DEX, mean weight of tumors was 0.59+/−0.04 g, whereas PBS-treated tumors had a mean weight of 1.51+/−0.13 g (***p=0.0001). Toxicity and efficacy of CpdA and analogues will be evaluated.

Breast cancer xenograft model

Apoptosis-inducing activities of syneprhine analogues in breast cancer (MDA-MB 435) cells xenografted in athymic nude mice is determined by 9 mTc-Annexin V scintigraphy, PET-scan and histological staining (Dechsupa).

Example 362

Use of Syneprhine Derivatives in the Treatment of Osteoporosis

Isolation and culture of cells—FLS cells (fibroblast-like synoviocytes) were obtained from patients with active rheumatoid arthritis (RA), according to the revised criteria of the American College of Rheumatology. FLS were obtained by enzymatic digestion from synovial tissue, and cultured in Dulbecco Modified Eagle's Medium (DMEM) supplemented with 10% fetal calf serum (FCS), 100 units/ml penicillin and 0.1 mg/ml streptomycin. Experiments were performed using FLS with a passage number ranging from 4 to maximally 8. The study was approved by the local ethics committee and informed consent was obtained from all patients.

Cytokines and reagents—Recombinant murine TNF was produced in our laboratory Dexamethasone was purchased from Sigma. CpdA was synthesized as described previously. Anti-GR(H-300) and anti-p42/p44 (extracellular-signal-regulated kinase, ERK) were purchased from Santa Cruz Biotechnology and from Cell Signalling respectively. The Human Inflammation Antibody Array III was purchased from RayBiotech.

DBA/1 mice—Male 8- to 12-wk-old DBA/1 mice were purchased from Janvier and housed following institutional guidelines. All animal procedures were approved by the institutional animal care and ethics committee. Mice were randomized and were, during a period of 8 days, treated daily with PBS (200 µl), DEX (20 µg dissolved in 200 µl PBS) or CpdA (300 µg dissolved in 200 µl PBS) after which serum was collected. They were sacrificed and livers were isolated.

Glucocorticoid-Induced Osteoporosis

Q-PCR—FLS were seeded in 6 well plates and serum-starved 24 hours prior to induction. Cells were induced with solvent, DEX (1 µM), CpdA (10 µM) and TNF (2000 units/ml) as depicted in the figure. Total RNA was isolated by means of the RNeasy mini kit (Qiagen), according to the manufacturer's instructions. The mRNA was reverse transcribed with the verso cDNA kit (ABgene). The obtained cDNA was amplified in a quantitative PCR reaction containing the iQ Custom SYBR Green Supermix from Biorad. Gene expression of the housekeeping gene hypoxanthine-guanine phosphoribosyltransferase (HPRT) was used for normalization.

ELISA—FLS were seeded in 6 well plates and serum-starved 24 hours prior to induction. Cells were induced with solvent, DEX (1 µM), CpdA (10 µM) and TNF (2000 units/ml) as depicted in the figure. The medium of the cells was used to perform ELISA. The human IL-6 and IL-8 cytoset were purchased from BioSource International, Inc. For the detection of TRAP5b in DBA/1 mice serum we used the Mouse TRAP Assay, purchased from Immunodiagnostic systems limited. The osteocalcin EIA kit was purchased from Biomedical Technologies, Inc. All assays were performed according to the manufacturer's instructions.

Resistance

Western Blot analysis—FLS were seeded in six-well plates and grown to subconfluence before induction. Cells were induced with solvent, DEX (1 µM), CpdA (10 µM) and TNF (2000 units/ml) as depicted in the figure. Total protein was extracted and equal amounts of protein, were loaded onto a reducing SDS polyacrylamide gel, subjected to electrophoresis, and subsequently transferred to a nitrocellulose membrane. Detection of p42/p44 (ERK) was used as a loading control.

Q-PCR—After the appropriate inductions, as indicated in the figure, RNA was isolated from the FLS by means of the RNeasy mini kit (Qiagen) and according to the manufacturer's instructions. The mRNA was reverse transcribed with the verso cDNA kit (ABgene). For isolation of total RNA from murine livers, the tissue specimens were preserved in RNAlater (Ambion). Total RNA was extracted with the RNeasy mini kit (Qiagen) and subjected to DNase treatment (RNase-free DNase set, Qiagen) according to the manufacturer's instructions. cDNA from total RNA was synthesized as described before. The obtained cDNA was amplified by a quantitative PCR reaction with iQ Custom SYBR Green Supermix (Biorad). Gene expression of the housekeeping gene hypoxanthine-guanine phosphoribosyltransferase (HPRT) was used for normalization.

Results:

Glucocorticoid-Induced Osteoporosis (GIO)

Figure 14:
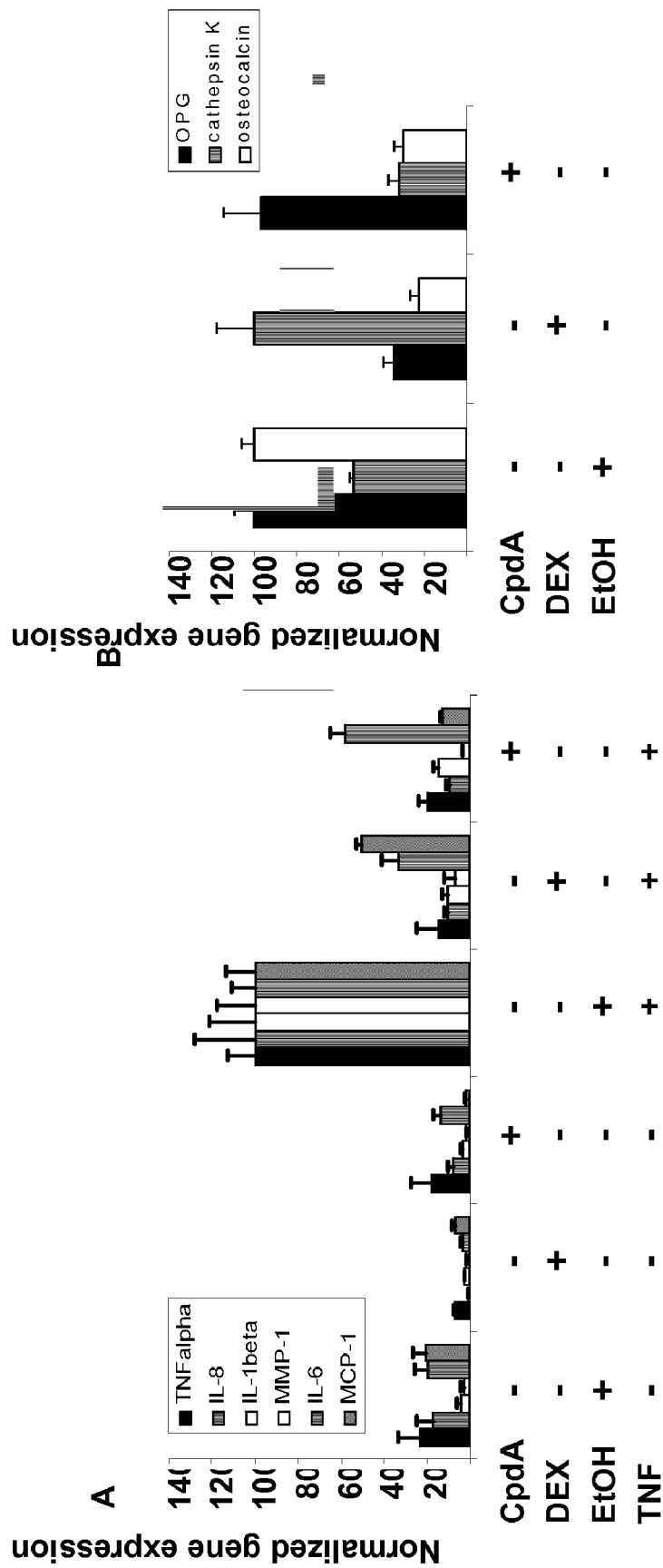
FIG. 14 shows the expression of bone related markers upon treatment of MG63 b osteosarcoma cells with compounds of the invention.

The gene regulatory effects of CpdA in the osteosarcoma cell-line MG63b are shown in FIG. 14A. Herein, MG63b were treated with DEX (1 µM), CpdA (10 µM) or solvent (EtOH), after which TNF (2000 U/ml) was added for 6 hours. In FIG. 14B MG63b were treated with DEX (1 µM), CpdA (10 µM) or solvent (EtOH) for 24 hours. Total RNA was isolated from the induced cells and subjected to reverse transcriptase PCR. Expression of the pro-inflammatory mediators TNFα, MCP-1, IL-8, IL-6, IL-1b and MMP-1 and of the osteoporosis markers OPG and cathepsink was monitored by means of Q-PCR analysis. Gene expression of HPRT was used for normalization.

Figure 15:
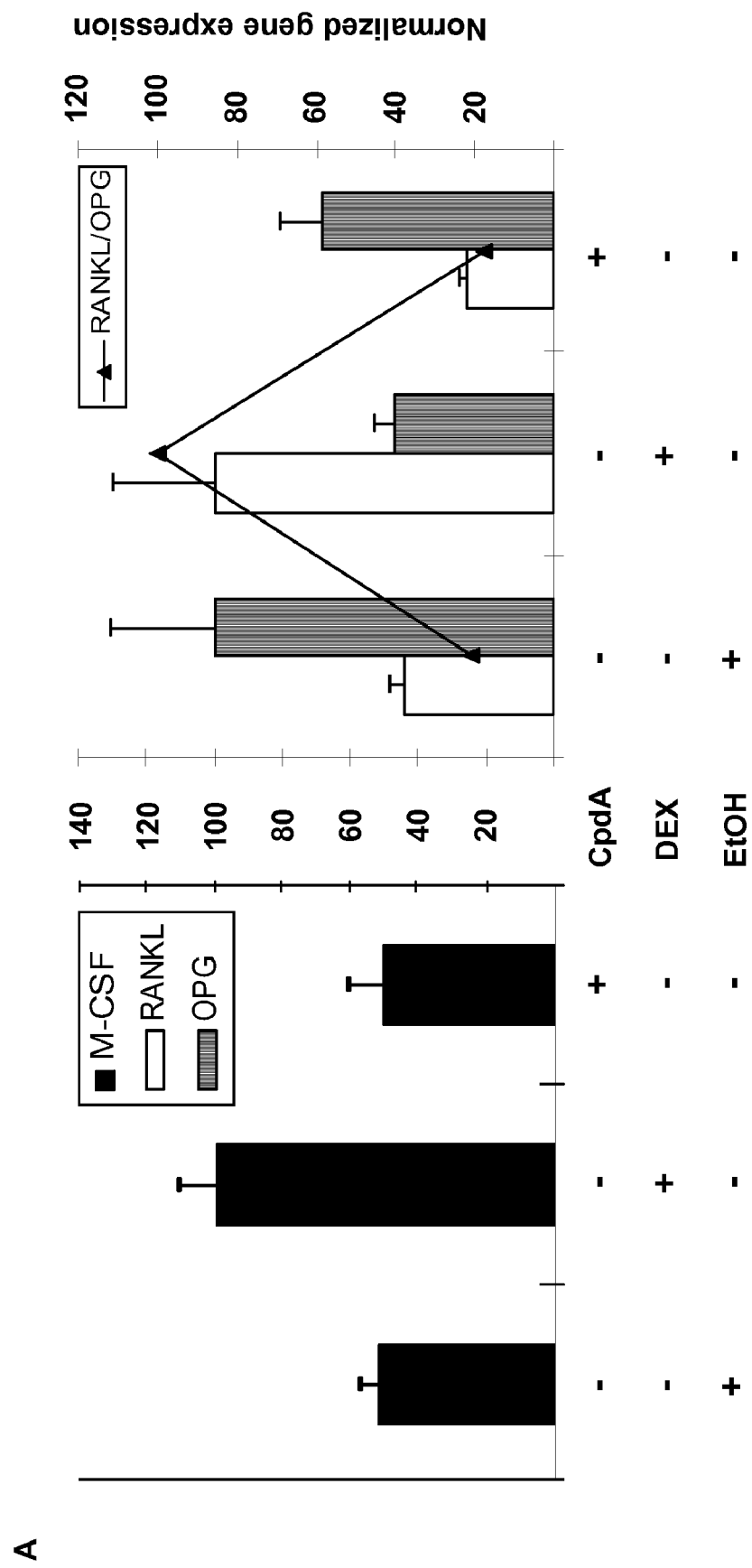
FIGS. 15 and 16 show the expression of bone related markers upon treatment of Saos-2 cells with compounds of the invention.
Figure 16:
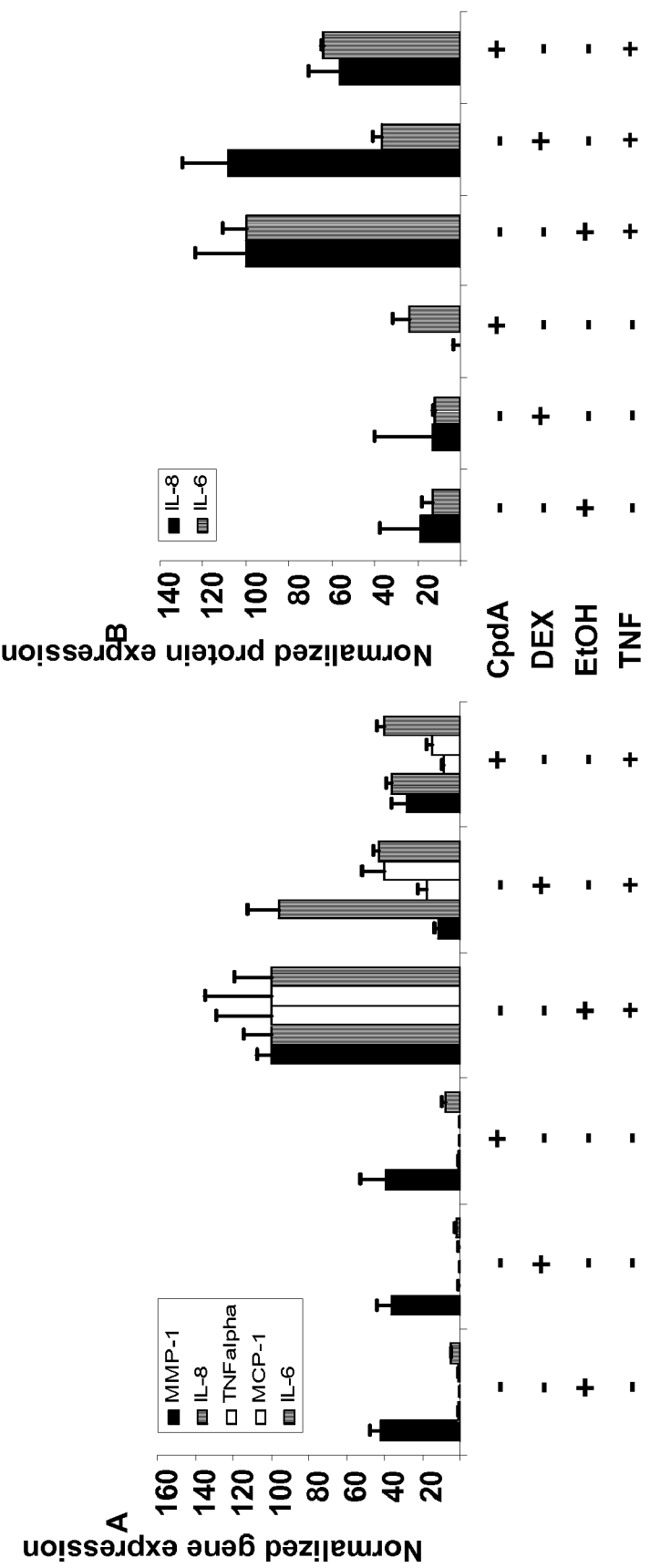

The gene regulatory effects of CpdA in the osteosarcoma cell-line Saos-2. are shown in FIGS. 16 A and B. Saos-2 were treated with DEX (1 µM), CpdA (10 µM) or solvent (EtOH), after which TNF (2000 U/ml) was added for 6 hours (FIG. 16A). Total RNA was isolated from the induced cells and subjected to reverse transcriptase PCR. Expression of the pro-inflammatory mediators TNFα, MCP-1, IL-8, IL-6 and MMP-1 was monitored by means of Q-PCR analysis. Gene expression of HPRT was used for normalization. After the appropriate inductions, the medium of the cells was collected and subjected to an ELISA assay for the detection of IL-6 and IL-8 protein (FIG. 16). Saos-2 were treated with DEX (1 µM), CpdA (10 µM) or solvent (EtOH) for 24 hours, after which total RNA was isolated and subjected to reverse transcriptase PCR. Expression of the osteoporosis markers M-CSF, RANKL (solvent versus DEX: p<0.05; solvent versus CpdA: p>0.05) and OPG (solvent versus DEX: p<0.05; solvent versus CpdA: p>0.05) was monitored by means of Q-PCR analysis (FIG. 15). Gene expression of HPRT was used for normalization. Statistical significance was determined by one way anova.

Figure 17:
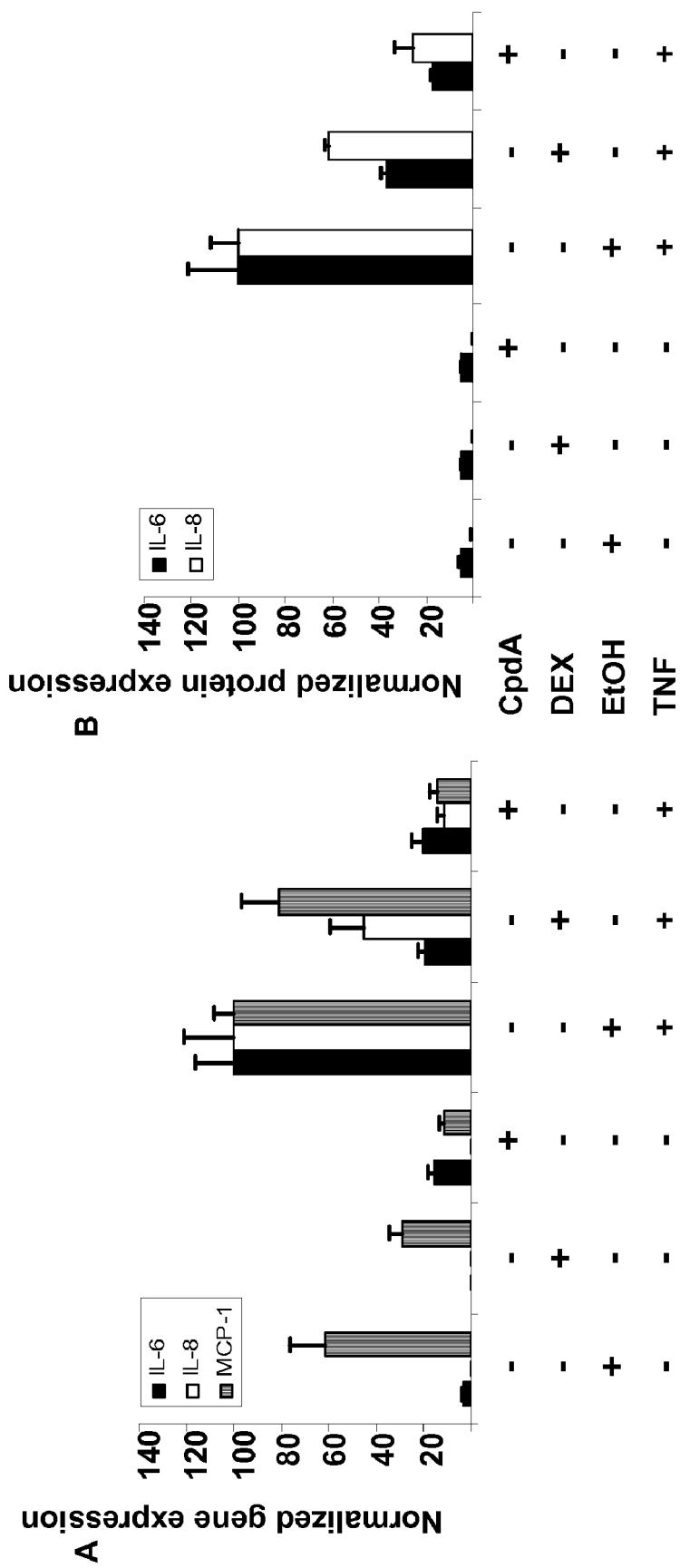
FIG. 17 shows the expression of inflammation markers in FLS cells upon treatment with compound of the invention.
Figure 18:
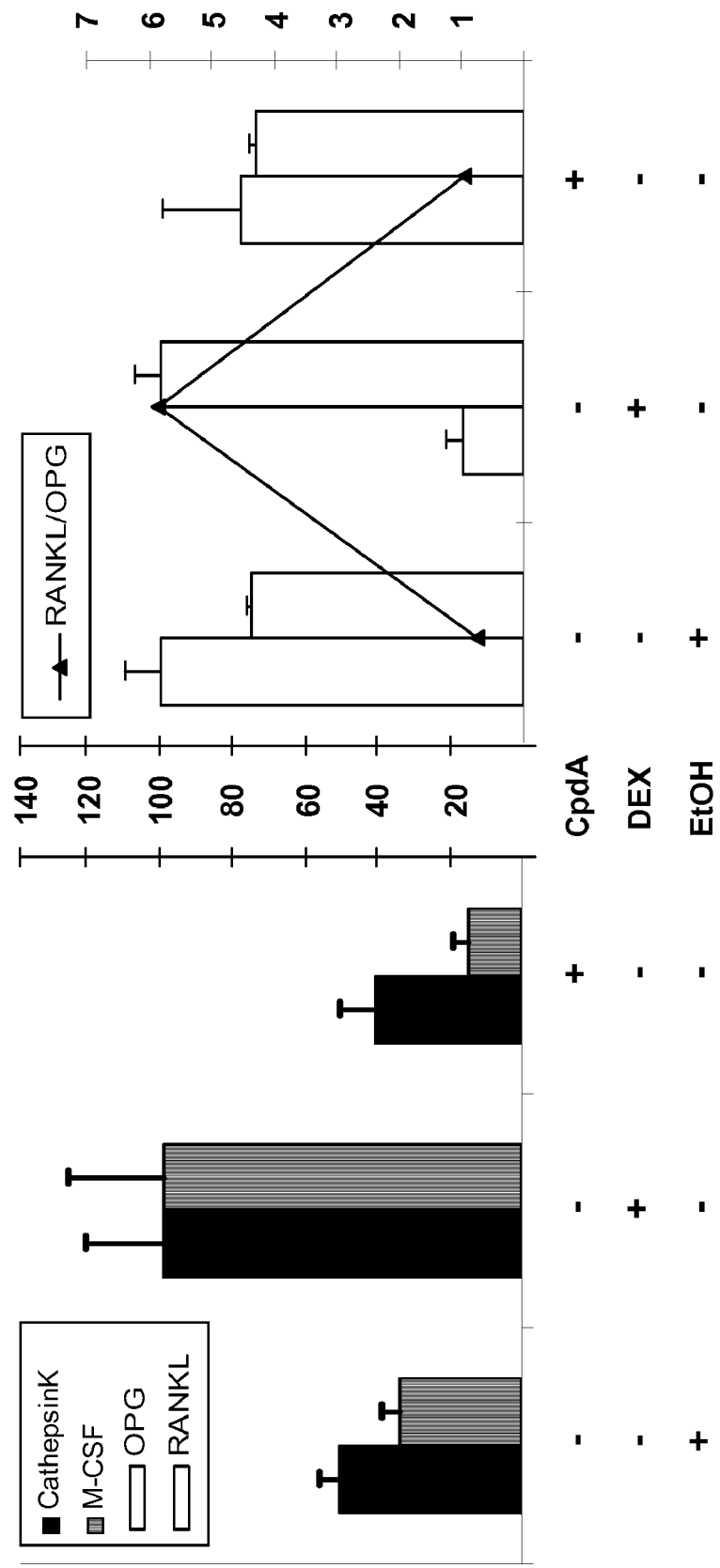
FIG. 18 show the expression of bone related markers upon treatment of FLS cells with compounds of the invention.

The gene regulatory effects of CpdA in primary FLS isolated from the inflamed synovium of RA patients are shown in FIGS. 17 and 18. FLS were treated with DEX (1 μM), CpdA (10 μM) or solvent (EtOH), after which TNF (2000 U/ml) was added for 6 hours. Total RNA was isolated from the induced cells and subjected to reverse transcriptase PCR. Expression of the pro-inflammatory mediators MCP-1, IL-8 and IL-6 was monitored by means of Q-PCR analysis (FIG. 17 A). Gene expression of HPRT was used for normalization. After the appropriate inductions, the medium of the cells was collected and subjected to an ELISA assay for the detection of IL-6 and IL-8 protein (FIG. 17B). FLS were treated with DEX (1 μM), CpdA (10 μM) or solvent (EtOH) for 24 hours, after which total RNA was isolated and subjected to reverse transcriptase PCR. Expression of the osteoporosis markers Cathepsin K, M-CSF, RANKL (solvent versus DEX: p<0.01; solvent versus CpdA: p>0.05) and OPG (solvent versus DEX: p<0.01; solvent versus CpdA: p>0.05) was monitored by means of Q-PCR analysis (FIG. 18). Gene expression of HPRT was used for normalization. Statistical significance was determined by one way anova.

Figure 21:
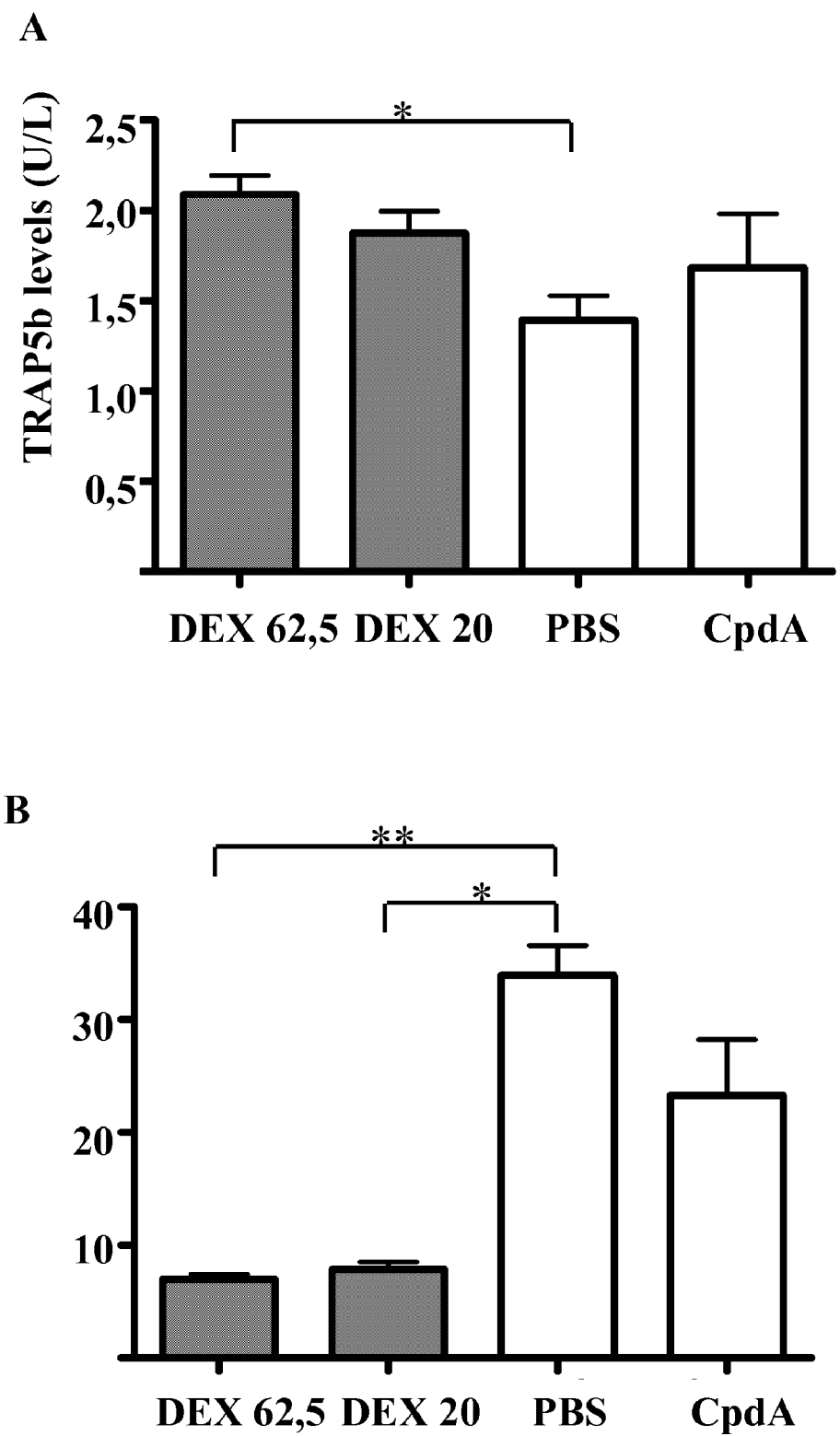
FIG. 21 shows the effect of CdpA on osteoclast and osteoblast markers in DBA/1 mice after Glucocorticoid Induced Osteoporosis

The effect of Compound A on osteoblast and osteoclast markers is shown in FIG. 21. After 8 days of treatment serum samples were taken from the PBS, DEX (20 μg), DEX (62.5 μg) or CpdA (300 μg) treated DBA/1 mice and subjected to ELISA for the detection of TRAP5B (FIG. 21A) and osteocalcin (FIG. 21B). Statistical significance was determined with a Kruskal-Wallis test.

The above data demonstrated the anti-inflammatory effect of CpdA in the osteosarcoma cell lines MG63b and Saos-2 and in the primary FLS isolated from the inflamed synovium of RA patients. Furthermore, we analyzed the expression of different osteoporosis markers in the different cells. First we determined the effect of DEX and CpdA on the expression of matrix degrading enzymes, such as matrix metalloproteinase (MMP-1) and cathepsins (cathepsin K), which expression pattern is known to be relevant for diagnosis and monitoring osteochondral disorders such as osteoporosis. Subsequently, we determined the effect of CpdA and DEX on the osteoclast differentiation markers monocyte colony stimulating factor (M-CSF) and receptor activator of NF-kappaB ligand (RANKL). Glucocorticoids stimulate the expression of M-CSF and RANKL, thereby stimulating monocytes/macrophages to differentiate into tartrate-resistant acid phosphatase (TRAP) positive multinucleated cells, namely osteoclasts. The amount of free RANKL is further determined by the levels of osteoprotegerin (OPG). OPG acts as a decoy receptor of RANKL, thereby preventing the interaction between RANKL and its cognate receptor RANK. Consequently, down-regulation of OPG by GCs shifts the RANKL/OPG balance to promote osteoclast differentiation and activation. Although GC-induced osteoporosis (GIO) can be considered a multifactoral pathogenesis, it is assumed that increased bone resorption worsened by inhibition of new bone formation mainly contributes to the GC-mediated decrease in bone mineral density (BMD). The transrepressive effect of GCs on the expression of osteocalcin (OC), a specific marker of osteoblast function, is thus adding to the deleterious effects of these drugs on the bone.

Figure 22:
FIG. 22 shows the resistance homologous down regulation of GR in GLS cells of DBA/1 mice.
Figure 22:
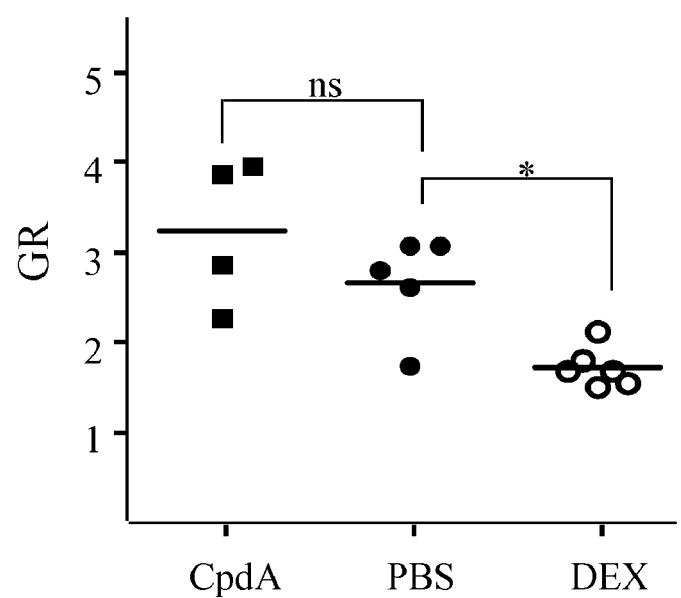

As a consequence, our results clearly indicate that CpdA displays an improved side-effect profile in comparison with DEX with regard to glucocorticoid-induced osteoporosis (GIO). Our data clearly indicate that CpdA, in contrast to DEX, does not stimulate the expression of cathepsin K in MG63b and FLS. Furthermore, CpdA does not stimulate the expression of the osteoclast differentiation markers M-CSF and RANKL in Saos-2 and FLS. Additionally, CpdA does not down-regulate the expression of OPG in MG63b, Saos-2 and FLS. As a consequence, CpdA does not alter the RANKL/OPG ratio. These data are reflected in DBA/1 mice. Our data show that daily treatment of the mice with CpdA does not alter the amount of active osteoclasts (TRAP5b). It is only after an 8 day treatment with 62.5 μg DEX that an increase of TRAP5b in mouse serum could be observed. Furthermore, we show that CpdA does not significantly alter the osteocalcin levels in mouse serum, which is in sharp contrast to DEX. The homologous down-regulation of GR in FLS and DBA/1 mice in shown in FIG. 22. FLS were treated with DEX (1 μM), CpdA (10 μM) or solvent (EtOH) for 3, 6, 9 or 24 hours as indicated in FIG. 22A. Western blot analysis was performed on total protein extracts with an anti-GR(H-300) antibody. The detection of ERK was used as a loading control. After 8 days of treatment liver samples were taken from the PBS, DEX (20 μg) or CpdA (300 μg) treated DBA/1 mice (FIG. 22B). Q-PCR was performed for the detection of GR in the different samples. Statistical significance was determined with a Mann-Whitney Test.

Figure 19:
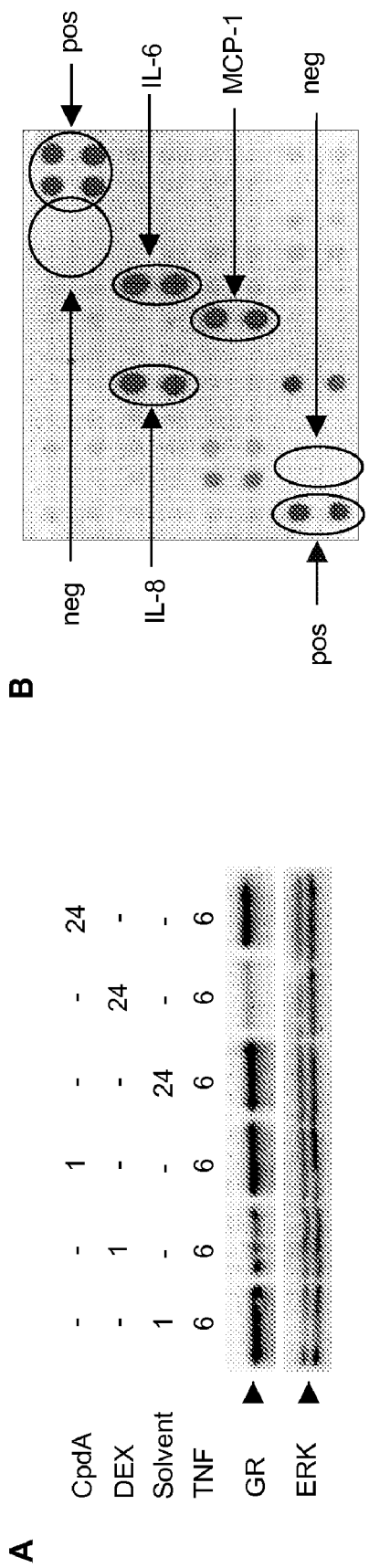
FIG. 19 shows the anti inflammatory effects of the resistance homologous downregulation of GR in FLS cells.
Figure 19:
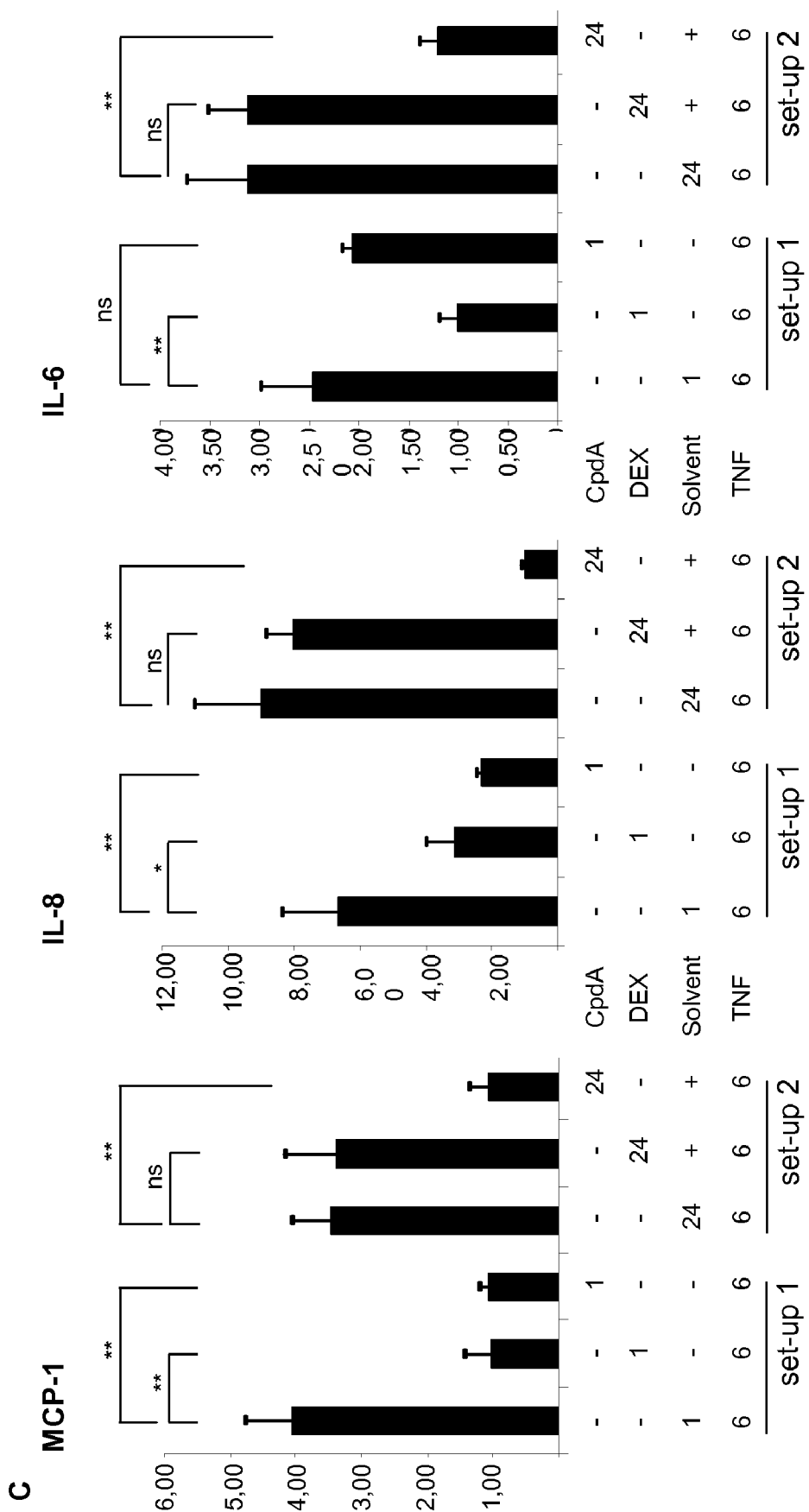
Figure 20:
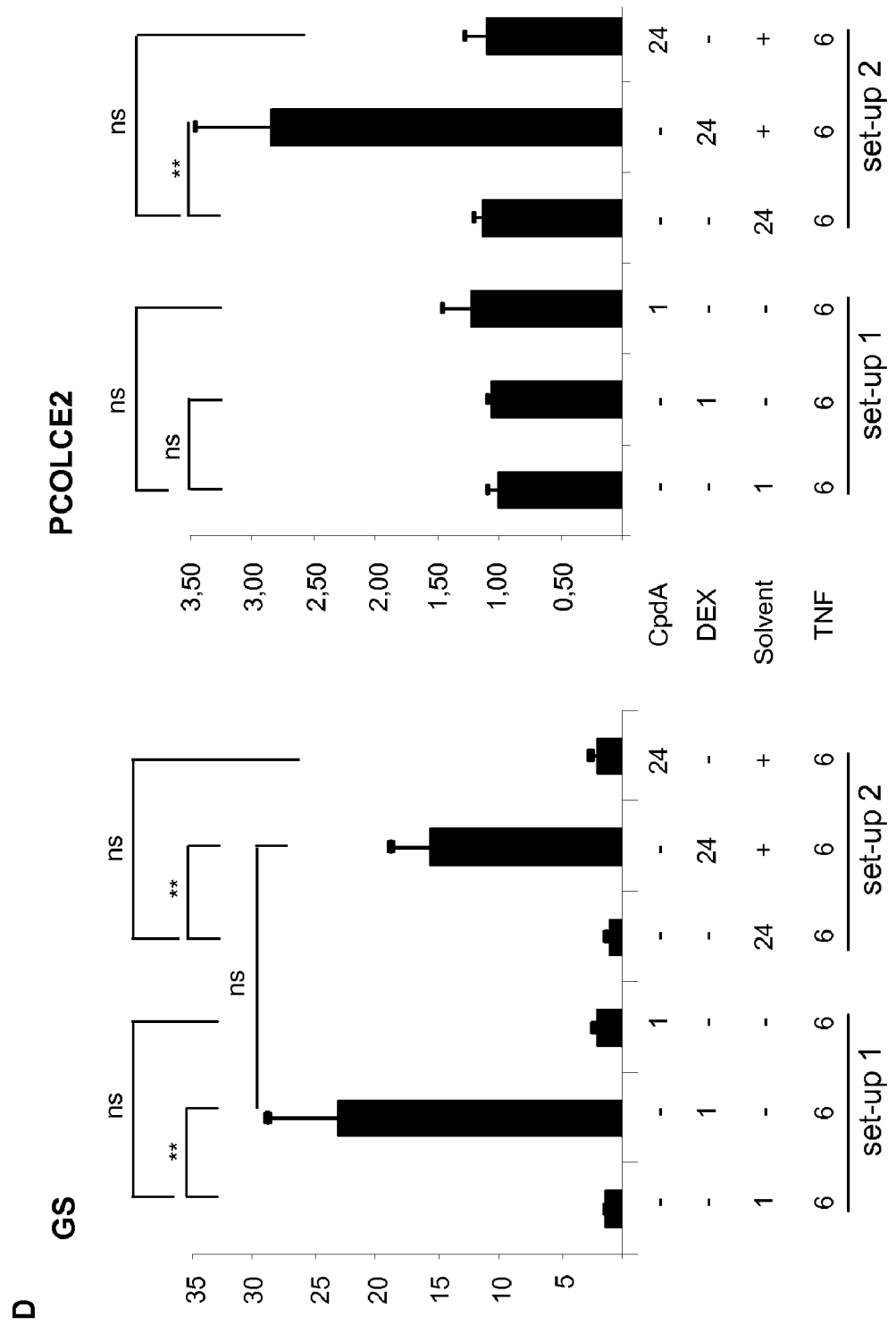
FIG. 20 shows that resistance homologous downregulation of GR in FLS cells does not affect GRE-driven gene expression.

The effects of homologous down-regulation on the regulation of gene expression in FLS are shown in FIGS. 19 and 20. FLS were pre-treated with solvent, DEX (1 μM) or CpdA (10 μM) for 1 hour (set-up 1) or 24 hours (set-up 2), as indicated in the figures. Afterwards, TNF (2000 units/ml) was added for 6 h. Western blot analysis was performed on total extracts with an anti-GR(H-300) antibody (FIG. 19A). Detection of ERK was used as a loading control. The Human Inflammation Array was incubated with medium of cultured FLS and developed following the manufacturer's instruction (FIG. 19B). Total RNA was isolated from the induced FLS and subjected to reverse transcriptase PCR. Expression of the pro-inflammatory mediators MCP-1, IL-8 and IL-6 (FIG. 19C), as well as of the GRE-driven PCOLCE2 and GS (FIG. 20) was monitored by means of Q-PCR analysis. Gene expression of HPRT was used for normalization. Statistical significance was determined by one way anova.

These data show that in contrast to DEX, CpdA does not evoke a ligand-induced down-regulation of the glucocorticoid receptor (GR) in fibroblast-like synoviocytes (FLS) isolated from the inflamed synovium of rheumatoid arthritis (RA) patients. Since it has been proposed that the cellular sensitivity to GC is directly proportional to the receptor concentration, the mechanism of homologous down-regulation appears to drastically affect the cellular sensitivity of primary human RA-FLS to GC therapy. Our data indeed indicate that prolonged treatment (24 hours) of FLS with DEX drastically hampers the anti-inflammatory effects of DEX, as indicated by the abolishment of pro-inflammatory cytokine (MCP-1, IL-8 and IL-6) repression by DEX in set-up 2. Such an effect can not be observed with CpdA. Our data illustrate that even after prolonged treatment of FLS with CpdA, the GR levels are unaffected and as a consequence, CpdA is still able to repress the TNF-induced expression of MCP-1, IL-8 and IL-6 in experimental set-up 2. Furthermore, we show that after prolonged treatment with DEX (under conditions that the glucocorticoid receptor levels are low), DEX is still able to induce the transactivation function of the receptor. Notwithstanding some exceptions, a body of evidence supports that the transrepression function of the receptor is mainly responsible for the anti-inflammatory effects, while its transactivation function is held mostly responsible for some of the metabolic side effects. Therefore, it is not surprising that some patients who develop resistance to the therapeutic effects of GC, still display the unwanted effects associated with prolonged GC treatment. It is thus very interesting to note that CpdA does not evoke the transactivation function of GR in the primary FLS, yet displays its anti-inflammatory effects even after prolonged treatment, thereby circumventing ligand-induced resistance.

All publications and patent applications mentioned in this specification are herein incorporated by reference to the same extent as if each independent publication or patent application was specifically and individually indicated to be incorporated by reference.

Other embodiments are within the scope of the claims.

What is claimed is:

1. A compound represented by the structural formula (I):

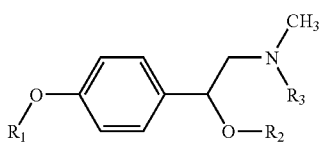

wherein:
$R_1$ is —C(=O)—$R_4$ or —S(=O)$_2$—$R_4$,
$R_2$ is —C(=O)—$R_6$,
$R_3$ is hydrogen, —C(=O)—$R_7$, —C(=O)—$OR_7$ or aryl-$C_{1-7}$ alkyl;
$R_4$ is selected from the group consisting of $R_5$, —$OR_5$, —$NHR_5$ and —$SR_5$,
$R_5$ is selected from the group consisting of hydrogen, $C_{1-10}$ alkyl, $C_{3-10}$ cycloalkyl, $C_{2-10}$ alkenyl, $C_{2-10}$ alkynyl, aryl, aryl-$C_{1-7}$ alkyl, and saturated, partly unsaturated or aromatic heterocyclic groups, wherein each of said alkyl groups may be substituted with one or more substituents independently selected from the group consisting of amino, hydroxyl, sulfhydryl and methoxy,
$R_6$ is selected from the group consisting of $C_{2-10}$ alkyl, $C_{3-10}$ cycloalkyl, $C_{2-10}$ alkenyl, $C_{2-10}$ alkynyl, aryl, arylalkyl, and saturated, partly unsaturated or aromatic heterocyclic groups, wherein each of said alkyl groups may be substituted with one or more substituents independently selected from the group consisting of amino, hydroxyl, sulfhydryl and methoxy,
$R_7$ is selected from the group consisting of $C_{1-10}$ alkyl, $C_{2-10}$ alkenyl, aryl and aryl-$C_{1-10}$ alkyl, wherein each of said alkyl groups may be substituted with one or more substituents independently selected from the group consisting of amino, hydroxyl, sulfhydryl and methoxy, and wherein each of said $C_{2-10}$ alkenyl or aryl groups may be substituted with one or more substituents independently selected from the group consisting of halogen, alkyl, alkoxy, nitro, cyano and hydroxy,
a stereoisomer thereof, or a salt thereof.

2. A compound according to claim 1, wherein $R_1$ is —C(=O)—$R_4$, and $R_4$ is $R_5$.

3. A compound according to claim 1, wherein $R_1$ is —C(=O)—$R_4$, and $R_4$ is $R_5$, and $R_1$ is the same as $R_2$.

4. A compound according to claim 1, wherein $R_1$ is selected from the group consisting of benzoyl, p-toluoyl, 1-naphthalenecarbonyl, 2-naphthalenecarbonyl, 4-morpholinocarbonyl, 1-piperidinocarbonyl, 1-imidazolidinocarbonyl, 1-pyrrolidinocarbonyl, 2-thiazolecarbonyl, 1-methyl-1H-pyrrole-2-carbonyl, 2-furanecarbonyl, 3-furanecarbonyl, 3-pyridinecarbonyl, 4-pyridinecarbonyl, 2-thiophenecarbonyl, cyclobutanecarbonyl, cyclopentane-carbonyl, cyclohexanecarbonyl, 1-adamantanecarbonyl, pipecolinyl and 2-norbornanecarbonyl.

5. A compound according to claim 1, wherein $R_1$ is selected from the group consisting of formyl, propanoyl, butanoyl and pentanoyl.

6. A compound according to claim 1, wherein $R_3$ is the same as $R_2$.

7. A compound according to claim 1, wherein $R_3$ is selected from the group consisting of arylcarbonyl, alkyloxycarbonyl and arylalkyloxycarbonyl.

8. A compound according to claim 1, wherein $R_3$ is tert-butoxycarbonyl.

9. A compound according to claim 1, wherein $R_6$ is imidazolyl or triazolyl.

10. A method for preparing a compound according to claim 1, comprising the steps of:
(a) reacting synephrine with an amino-protecting reagent to form an amino-protected synephrine,
(b) reacting said amino-protected synephrine with a chloride selected from the group consisting of carboxylic acid chlorides, carbamic acid chlorides, chloroformates, thiocarboxylic acid chlorides, imidic acid chlorides and sulfonic acid chlorides to produce a 4-[2-(N-protected-methylamino)-1-hydroxyethyl]phenyl ester, and
(c) reacting said 4-[2-(N-protected-methylamino)-1-hydroxyethyl]phenyl ester with an activated carbonyl compound selected from the group consisting of carboxylic acid chlorides, carbamic acid chlorides, chloroformates, thiocarboxylic acid chlorides, imidic acid chlorides, 1,1'-carbonyldiimidazole, 1,1'-thiocarbonyldiimidazole and 1,1'-carbonylditriazole.

11. A method according to claim 10, wherein step (a) comprises reacting synephrine with an amino-protected thiazolidine-2-thione.

12. A method according to claim 11, wherein the amino-protected thiazolidine-2-thione used in step (a) is tert-butoxycarbonyl-thiazolidine-2-thione and said amino protected synephrine is a tert-butoxycarbonyl-protected synephrine.

13. A method according to claim 10, wherein said activated carbonyl compound in step (b) is a carboxylic acid chloride.

14. A method according to claim 10, further comprising the step (d) of selectively de-protecting the amino group of the compound resulting from step (c), without affecting any of groups $R_1$ and $R_2$.

15. A pharmaceutical composition comprising a therapeutic effective amount of a compound according to claim 1, and optionally one or more pharmaceutically acceptable carriers, and optionally further comprising a therapeutic amount of one or more anti-inflammatory drugs.

16. A compound according to claim 1, wherein $R_3$ is hydrogen, $R_1$ is C(=O)—$R_4$, and $R_4$ is methyl.

17. 4-[1-(acetyloxy)-2-(methylamino)ethyl]phenyl acetate hydrochloride.

18. A compound selected from the group consisting of:
1-[4-(benzoyloxy)phenyl]-2-[(tert-butoxycarbonyl)-methylamino]ethyl-1H-imidazole-1-carboxylate,
1-[4-(isobutanoyloxy)phenyl]-2-[(tert-butoxycarbonyl)-methylamino]ethyl-1H-imidazole-1-carboxylate,
1-[4-(hexanoyloxy)phenyl]-2-[(tert-butoxycarbonyl)-methylamino]ethyl-1H-imidazole-1-carboxylate, and
1-[4-(naphthoyloxy)phenyl]-2-[(tert-butoxy-carbonyl)-methylamino]ethyl-1H-imidazole-1-carboxylate.

19. A compound selected from the group consisting of:
4-{2-[(tert-butoxycarbonyl)(methyl)amino]-1-hydroxyethyl}phenyl isobutyrate;

4-{2-[(tert-butoxycarbonyl)(methyl)amino]-1-hydroxyethyl}phenyl hexanoate; and

4-{2-[(tert-butoxycarbonyl)(methyl)-amino]-1-hydroxyethyl}phenyl 1-naphthoate.

20. A pharmaceutical composition comprising a therapeutic effective amount of a compound according to claim 16, and optionally one or more pharmaceutically acceptable carriers, and optionally further comprising a therapeutic amount of one or more anti-inflammatory drugs.

21. A pharmaceutical composition comprising a therapeutic effective amount of a compound according to claim 17, and optionally one or more pharmaceutically acceptable carriers, and optionally further comprising a therapeutic amount of one or more anti-inflammatory drugs.

22. A pharmaceutical composition comprising a therapeutic effective amount of a compound according to claim 18, and optionally one or more pharmaceutically acceptable carriers, and optionally further comprising a therapeutic amount of one or more anti-inflammatory drugs.

23. A pharmaceutical composition comprising a therapeutic effective amount of a compound according to claim 19, and optionally one or more pharmaceutically acceptable carriers, and optionally further comprising a therapeutic amount of one or more anti-inflammatory drugs.

* * * * *